US012717231B2

(12) United States Patent
Aqad et al.

(10) Patent No.: US 12,717,231 B2
(45) Date of Patent: Aug. 25, 2026

(54) PHOTOACTIVE COMPOUNDS, PHOTORESIST COMPOSITIONS INCLUDING THE SAME, AND PATTERN FORMATION METHODS

(71) Applicant: ROHM AND HAAS ELECTRONIC MATERIALS LLC, Marlborough, MA (US)

(72) Inventors: Emad Aqad, Northborough, MA (US); Jong Keun Park, Shrewsbury, MA (US); Yinjie Cen, Shrewsbury, MA (US); Choong-Bong Lee, Westborough, MA (US)

(73) Assignee: DUPONT ELECTRONIC MATERIALS INTERNATIONAL, LLC, Marlborough, MA (US)

( * ) Notice: Subject to any disclaimer, the term of this patent is extended or adjusted under 35 U.S.C. 154(b) by 624 days.

(21) Appl. No.: 17/710,126

(22) Filed: Mar. 31, 2022

(65) Prior Publication Data

US 2023/0314934 A1 Oct. 5, 2023

(51) Int. Cl.

| | |
|---|---|
| ***C07C 57/42*** | (2006.01) |
| ***C07C 255/19*** | (2006.01) |
| ***C07C 381/12*** | (2006.01) |
| ***G03F 7/004*** | (2006.01) |
| *G03F 7/038* | (2006.01) |
| *G03F 7/039* | (2006.01) |

(52) U.S. Cl.

CPC ............ *G03F 7/0045* (2013.01); *C07C 57/42* (2013.01); *C07C 255/19* (2013.01); *C07C 381/12* (2013.01); *G03F 7/004* (2013.01); *G03F 7/0382* (2013.01); *G03F 7/0397* (2013.01)

(58) Field of Classification Search

None

See application file for complete search history.

(56) References Cited

U.S. PATENT DOCUMENTS

| | | | |
|---|---|---|---|
| 4,189,323 | A | 2/1980 | Buhr |
| 4,193,935 | A | 3/1980 | Cannon |
| 6,136,500 | A | 10/2000 | Kobayashi et al. |
| 6,485,883 | B2 | 11/2002 | Kodama et al. |
| 8,431,325 | B2 | 4/2013 | Hashimoto et al. |
| 8,936,000 | B2 | 1/2015 | Nonaka |
| 10,824,073 | B2 * | 11/2020 | Nishikori .......... C08F 220/1818 |
| 2015/0355544 | A1 | 12/2015 | Fukushima et al. |
| 2017/0075217 | A1 * | 3/2017 | Hatakeyama ......... C07C 219/02 |
| 2019/0113844 | A1 | 4/2019 | Hatakeyama et al. |
| 2019/0155155 | A1 * | 5/2019 | Hatakeyama ......... G03F 7/0392 |
| 2019/0361342 | A1 | 11/2019 | Maehashi et al. |
| 2021/0200089 | A1 | 7/2021 | Yamazaki et al. |
| 2021/0200092 | A1 | 7/2021 | Su et al. |
| 2022/0043343 | A1 * | 2/2022 | Hatakeyama ........... C07C 63/06 |
| 2022/0299875 | A1 * | 9/2022 | Maruyama ............ G03F 7/0392 |
| 2024/0377742 | A1 * | 11/2024 | Maruyama ............ G03F 7/0392 |

FOREIGN PATENT DOCUMENTS

| | | | |
|---|---|---|---|
| JP | H01209712 | A | 8/1989 |
| JP | H0246714 | A | 2/1990 |
| JP | H03267941 | A | 11/1991 |
| JP | 2015232598 | A | 12/2015 |

(Continued)

OTHER PUBLICATIONS

Wei et al., Promotion of the photoacid generation performance of sulfonium salts by inhibiting the isomerization of conjugated systems utilizing a cyclization strategy, Journal of Polymer Science, 60, 8, 1371-1382 (Year: 2021).*

Crank et al., "Towards a Second Generation of Ionic Liquid Matrices (ILMs) for MALDI-MS of Peptides, Proteins, and Carbohydrates," Journal of the American Society for Mass Spectrometry, 2009, vol. 20, No. 10, p. 1790-1800.

Registry (STN) [online], [Search date] Jun. 3, 2024, Feb. 4, 2015, May 12, 2009, CAS Registration No. 1644555-19-0, CAS Registration No. 1145778-68-2.

Tolstaya et al., "Synthesis of Cyclic Iodonium Salts Containing an Asymmetric Carbon Atom," Chemistry of Heterocyclic Compounds (New York) (Translation of Khimiya Geterotsiklicheskikh Soedinenii), 2000, Volume Date 1999, vol. 35, No. 8, p. 978-983.

*Primary Examiner* — Mark F. Huff
*Assistant Examiner* — Richard David Champion
(74) *Attorney, Agent, or Firm* — CANTOR COLBURN LLP

(57) ABSTRACT

A photoactive compound of formula (1a) or (1b):

(1a)

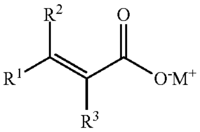

(1b)

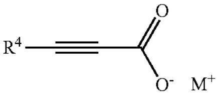

wherein $R^1$ is substituted or unsubstituted $C_{1-30}$ alkyl, substituted or unsubstituted $C_{3-30}$ cycloalkyl, substituted or unsubstituted $C_{3-30}$ heterocycloalkyl, substituted or unsubstituted $C_{6-30}$ aryl, or substituted or unsubstituted $C_{3-30}$ heteroaryl comprising an aromatic ring heteroatom chosen from nitrogen, oxygen, or a combination thereof; $R^2$ and $R^3$ are as provided herein; $R^4$ is substituted or unsubstituted $C_{1-30}$ alkyl, substituted or unsubstituted $C_{3-30}$ cycloalkyl, substituted or unsubstituted $C_{3-30}$ heterocycloalkyl, substituted or unsubstituted $C_{6-30}$ aryl, or substituted or unsubstituted $C_{3-30}$ heteroaryl; and $M^+$ is an organic cation.

15 Claims, No Drawings

(56) References Cited

FOREIGN PATENT DOCUMENTS

| | | | |
|---|---|---|---|
| JP | 2019207301 | A | 12/2019 |
| JP | 2021099385 | A | 7/2021 |
| JP | 2022091720 | A | 6/2022 |
| WO | 2021182394 | A1 | 9/2021 |

* cited by examiner

PHOTOACTIVE COMPOUNDS, PHOTORESIST COMPOSITIONS INCLUDING THE SAME, AND PATTERN FORMATION METHODS

FIELD

The present invention relates to photoactive compounds for photoresist compositions and to pattern formation methods using such photoresist compositions. The invention finds applicability in lithographic applications in the semiconductor manufacturing industry.

BACKGROUND

Photoresist materials are photosensitive compositions typically used for transferring an image to one or more underlying layers such as a metal, a semiconductor, or a dielectric layer disposed on a substrate. To increase the integration density of semiconductor devices and to allow for the formation of structures having dimensions in the nanometer range, photoresists and photolithography processing tools having high-resolution capabilities have been developed.

Chemically amplified photoresists are conventionally used for high-resolution processing. Such resists typically employ a polymer having acid-labile groups, a photoacid generator and an acid quenching material. Pattern-wise exposure to activating radiation through a photomask causes the acid generator to form an acid which, during post-exposure baking, causes cleavage of the acid-labile groups in exposed regions of the polymer. Acid quenching materials are often added to the photoresist composition for controlling the diffusion of the acid to unexposed region to improve the contrast. The result of the lithographic process is the creation of difference in solubility characteristics between exposed and unexposed regions of the resist in a developer solution. In a positive tone development (PTD) process, exposed regions of the photoresist layer become soluble in the developer and are removed from the substrate surface, whereas unexposed regions, which are insoluble in the developer, remain after development to form a positive image. The resulting relief image permits selective processing of the substrate.

Non-photoactive acid quenching materials that are commonly used in chemically amplified resist include linear aliphatic amines, cyclic aliphatic amines, aromatic amines, linear and cyclic amides, and derivatives thereof. Another type of commonly used acid quenching material class is photoactive quenchers, known as photodecomposable quencher or photodegradable quencher. Photoactive quenchers have also been used in chemically amplified resist compositions. A photodecomposable quencher is typically a salt comprising a photoactive onium cation and an anion, wherein the anion is the conjugated base of weak acid. The salt functions as a base or acid quencher before exposure. Upon exposure, the anion part of the photodegradable quencher becomes protonated and therefore becomes more acidic. Therefore, upon irradiation of chemically amplified resist that comprises photodecomposable quencher, the concentration of the acid quencher in the exposed area decreased dramatically. On the other hand, the intact photodecomposable quencher in the unexposed area may trap acid molecules that diffuse from the exposed area during lithographic processing, thereby improving lithographic performance.

Photoresist compositions including photodecomposable quenchers and their use have been described in the art. However, for many other applications, the need exists for new photoresists that can provide highly resolved line-space features with superior line edge roughness (LWR) and wider depth of focus (DOF).

SUMMARY

Provided is a photoactive compound of formula (1a) or (1b):

(1a)

(1b)

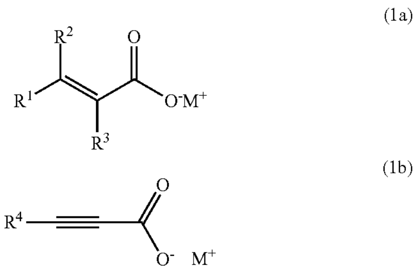

wherein $R^1$ is substituted or unsubstituted $C_{1-30}$ alkyl, substituted or unsubstituted $C_{3-30}$ cycloalkyl, substituted or unsubstituted $C_{3-30}$ heterocycloalkyl, substituted or unsubstituted $C_{6-30}$ aryl, or substituted or unsubstituted $C_{3-30}$ heteroaryl comprising an aromatic ring heteroatom chosen from nitrogen, oxygen, or a combination thereof; $R^2$ is hydrogen, halogen, substituted or unsubstituted $C_{1-30}$ alkyl, substituted or unsubstituted $C_{1-30}$ heteroalkyl, substituted or unsubstituted $C_{3-30}$ cycloalkyl, substituted or unsubstituted $C_{3-30}$ heterocycloalkyl, substituted or unsubstituted $C_{2-30}$ alkenyl, substituted or unsubstituted $C_{2-30}$ alkynyl, substituted or unsubstituted $C_1$-$C_{30}$ alkoxy group, substituted or unsubstituted $C_1$-$C_{30}$ alkylthio group, substituted or unsubstituted $C_3$-$C_{10}$ cycloalkenyl group, substituted or unsubstituted $C_3$-$C_{10}$ heterocycloalkenyl group, substituted or unsubstituted $C_{6-30}$ aryl, substituted or unsubstituted $C_{7-30}$ arylalkyl, substituted or unsubstituted $C_{7-30}$ alkylaryl, or substituted or unsubstituted $C_6$-$C_{30}$ aryloxy group; $R^3$ is hydrogen or a non-hydrogen substituent; $R^4$ is substituted or unsubstituted $C_{1-30}$ alkyl, substituted or unsubstituted $C_{3-30}$ cycloalkyl, substituted or unsubstituted $C_{3-30}$ heterocycloalkyl, substituted or unsubstituted $C_{6-30}$ aryl, or substituted or unsubstituted $C_{3-30}$ heteroaryl; each of $R^2$, $R^3$, and $R^4$ optionally further comprises one or more divalent linking group as part of their structure, wherein each of the one or more divalent linking groups is independently substituted or unsubstituted; $R^2$ and $R^3$ together optionally form a ring that optionally further comprises one or more divalent linking groups as part of its structure, wherein each of the one or more divalent linking groups is substituted or unsubstituted, and wherein the ring is substituted or unsubstituted; and $M^+$ is an organic cation.

Another aspect provides a photoresist composition comprising the photoactive compound and a solvent.

Still another aspect provides a method for forming a pattern comprising (a) forming a photoresist layer from a photoresist composition; (b) pattern-wise exposing the photoresist layer to activating radiation; and (c) developing the exposed photoresist layer to provide a resist relief image.

DETAILED DESCRIPTION

Reference will now be made in detail to exemplary embodiments, examples of which are illustrated in the present description. In this regard, the present exemplary embodiments may have different forms and should not be construed as being limited to the descriptions set forth herein. Accordingly, the exemplary embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

As used herein, the terms "a," "an," and "the" do not denote a limitation of quantity and are to be construed to cover both the singular and the plural, unless otherwise indicated herein or clearly contradicted by context. "Or" means "and/or" unless clearly indicated otherwise. The modifier "about" used in connection with a quantity is inclusive of the stated value and has the meaning dictated by the context (e.g., includes the degree of error associated with measurement of the particular quantity). All ranges disclosed herein are inclusive of the endpoints, and the endpoints are independently combinable with each other. The suffix "(s)" is intended to include both the singular and the plural of the term that it modifies, thereby including at least one of that term. "Optional" or "optionally" means that the subsequently described event or circumstance can or cannot occur, and that the description includes instances where the event occurs and instances where it does not. The terms "first," "second," and the like, herein do not denote an order, quantity, or importance, but rather are used to distinguish one element from another. When an element is referred to as being "on" another element, it may be directly in contact with the other element or intervening elements may be present therebetween. In contrast, when an element is referred to as being "directly on" another element, there are no intervening elements present. It is to be understood that the described components, elements, limitations, and/or features of aspects may be combined in any suitable manner in the various aspects.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "actinic rays" or "radiation" means, for example, a bright line spectrum of a mercury lamp, far ultraviolet rays represented by an excimer laser, extreme ultraviolet rays (EUV light), X-rays, particle rays such as electron beams and ion beams, or the like. In addition, in the present invention, "light" means actinic rays or radiation.

The argon fluoride laser (ArF laser) is a particular type of excimer laser, which is sometimes referred to as an exciplex laser. "Excimer" is short for "excited dimer," while "exciplex" is short for "excited complex." An excimer laser uses a mixture of a noble gas (argon, krypton, or xenon) and a halogen gas (fluorine or chlorine), which under suitable conditions of electrical stimulation and high pressure, emits coherent stimulated radiation (laser light) in the ultraviolet range.

Furthermore, "exposure" in the present specification includes, unless otherwise specified, not only exposure by a mercury lamp, far ultraviolet rays represented by an excimer laser, X-rays, extreme ultraviolet rays (EUV light), or the like, but also writing by particle rays such as electron beams and ion beams.

As used herein, the term "hydrocarbon" refers to an organic compound or group having at least one carbon atom and at least one hydrogen atom; "alkyl" refers to a straight or branched chain saturated hydrocarbon group having the specified number of carbon atoms and having a valence of one; "alkylene" refers to an alkyl group having a valence of two; "hydroxyalkyl" refers to an alkyl group substituted with at least one hydroxyl group (—OH); "alkoxy" refers to "alkyl-O—"; "carboxyl" and "carboxylic acid group" refer to a group having the formula "—C(═O)—OH"; "cycloalkyl" refers to a monovalent group having one or more saturated rings in which all ring members are carbon; "cycloalkylene" refers to a cycloalkyl group having a valence of two; "alkenyl" refers to a straight or branched chain, monovalent hydrocarbon group having at least one carbon-carbon double bond; "alkenoxy" refers to "alkenyl-O—"; "alkenylene" refers to an alkenyl group having a valence of two; "cycloalkenyl" refers to a non-aromatic cyclic divalent hydrocarbon group having at least three carbon atoms, with at least one carbon-carbon double bond; "alkynyl" refers to a monovalent hydrocarbon group having at least one carbon-carbon triple bond; the term "aromatic group" refers to a monocyclic or polycyclic ring system that satisfies the Huckel Rule and includes carbon atoms in the ring, and optionally may include one or more heteroatoms selected from N, O, and S instead of a carbon atom in the ring; "aryl" refers to a monovalent aromatic monocyclic or polycyclic ring system where every ring member is carbon, and may include a group with an aromatic ring fused to at least one cycloalkyl or heterocycloalkyl ring; "arylene" refers to an aryl group having a valence of two; "alkylaryl" refers to an aryl group that has been substituted with an alkyl group; "arylalkyl" refers to an alkyl group that has been substituted with an aryl group; "aryloxy" refers to "aryl-O—"; and "arylthio" refers to "aryl-S—".

The prefix "hetero" means that the compound or group includes at least one member that is a heteroatom (e.g., 1, 2, 3, or 4 or more heteroatom(s)) instead of a carbon atom, wherein the heteroatom(s) is each independently N, O, S, Si, or P; "heteroatom-containing group" refers to a substituent group that includes at least one heteroatom; "heteroalkyl" refers to an alkyl group having at least one heteroatom instead of carbon; "heterocycloalkyl" refers to a cycloalkyl group having at least one heteroatom as ring member instead of carbon; "heterocycloalkylene" refers to a heterocycloalkyl group having a valence of two.

The term "heteroaryl" means an aromatic 4-8 membered monocyclic, 8-12 membered bicyclic, or 11-14 membered tricyclic ring systems having 1-4 heteroatoms (if monocyclic), 1-6 heteroatoms (if bicyclic), or 1-9 heteroatoms (if tricyclic) that are each independently selected from N, O, S, Si, or P (e.g., carbon atoms and 1-3, 1-6, or 1-9 heteroatoms of N, O, or S, if monocyclic, bicyclic, or tricyclic, respectively). Examples of heteroaryl groups include pyridyl, furyl (furyl or furanyl), imidazolyl, benzimidazolyl, pyrimidinyl, thiophenyl or thienyl, quinolinyl, indolyl, thiazolyl, and the like.

Each of the foregoing substituent groups optionally may be substituted unless expressly provided otherwise. The term "optionally substituted" refers to being substituted or unsubstituted. "Substituted" means that at least one hydrogen atom of the chemical structure is replaced with another terminal substituent group that is typically monovalent, provided that the designated atom's normal valence is not exceeded. When the substituent is oxo (i.e., =O), then two geminal hydrogen atoms on the carbon atom are replaced with the terminal oxo group. Combinations of substituents or variables are permissible. Exemplary substituent groups that may be present on a "substituted" position include, but are not limited to, nitro (—$NO_2$), cyano (—CN), hydroxyl (—OH), oxo (=O), amino (—$NH_2$), mono- or di-($C_{1-6}$) alkylamino, alkanoyl (such as a $C_{2-6}$ alkanoyl group such as acyl), formyl (—C(=O)H), carboxylic acid or an alkali metal or ammonium salt thereof; esters (including acrylates, methacrylates, and lactones) such as $C_{2-6}$ alkyl esters (—C(=O)O-alkyl or —OC(=O)-alkyl) and $C_{7-13}$ aryl esters (—C(=O)O-aryl or —OC(=O)-aryl), amido (—C(=O)$NR_2$ wherein R is hydrogen or $C_{1-6}$ alkyl), carboxamido (—$CH_2C$(=O)$NR_2$ wherein R is hydrogen or $C_{1-6}$ alkyl), halogen, thiol (—SH), $C_{1-6}$ alkylthio (—S-alkyl), thiocyano (—SCN), $C_{1-6}$ alkyl, $C_{2-6}$ alkenyl, $C_{2-6}$ alkynyl, $C_{1-6}$ haloalkyl, $C_{1-9}$ alkoxy, $C_{1-6}$ haloalkoxy, $C_{3-12}$ cycloalkyl, $C_{5-13}$ cycloalkenyl, $C_{2-18}$ heterocycloalkenyl, $C_{6-12}$ aryl having at least one aromatic ring (e.g., phenyl, biphenyl, naphthyl, or the like, each ring either substituted or unsubstituted aromatic), $C_{7-19}$ arylalkyl having 1 to 3 separate or fused rings and from 6 to 18 ring carbon atoms, arylalkoxy having 1 to 3 separate or fused rings and from 6 to 18 ring carbon atoms, $C_{7-12}$ alkylaryl, $C_{3-12}$ heterocycloalkyl, $C_{3-12}$ heteroaryl, $C_{1-6}$ alkyl sulfonyl (—S(=O)$_2$-alkyl), $C_{6-12}$ arylsulfonyl (—S(=O)$_2$-aryl), or tosyl ($CH_3C_6H_4SO_2$—). When a group is substituted, the indicated number of carbon atoms is the total number of carbon atoms in the group, excluding those of any substituents. For example, the group —$CH_2CH_2CN$ is a cyano-substituted $C_2$ alkyl group.

The term "halogen" means a monovalent substituent that is fluorine (fluoro), chlorine (chloro), bromine (bromo), or iodine (iodo). The prefix "halo" means a group including one or more of a fluoro, chloro, bromo, or iodo substituent instead of a hydrogen atom. A combination of halo groups (e.g., bromo and fluoro), or only fluoro groups may be present. For example, the term "haloalkyl" refers to an alkyl group substituted with one or more halogens. As used herein, "substituted $C_{1-8}$ haloalkyl" refers to a $C_{1-8}$ alkyl group substituted with at least one halogen, and is further substituted with one or more other substituent groups that are not halogens. It is to be understood that substitution of a group with a halogen atom is not to be considered a heteroatom-containing group, because a halogen atom does not replace a carbon atom.

As used herein, an "acid-labile group" refers to a group in which a bond is cleaved by the catalytic action of an acid, optionally and typically with thermal treatment, resulting in formation of a polar group, such as a carboxylic acid or alcohol group, being formed on the polymer, and optionally and typically with a moiety connected to the cleaved bond becoming disconnected from the polymer. In other systems, a non-polymeric compound may include an acid-labile group that may be cleaved by the catalytic action of an acid, resulting in formation of a polar group, such as a carboxylic acid or alcohol group on a cleaved portion of the non-polymeric compound. Such acid is typically a photo-generated acid with bond cleavage occurring during post-exposure baking; however, embodiments are not limited thereto, and, for example, such acid may be thermally generated. Suitable acid-labile groups include, for example: tertiary alkyl ester groups, secondary or tertiary aryl ester groups, secondary or tertiary ester groups having a combination of alkyl and aryl groups, tertiary alkoxy groups, acetal groups, or ketal groups. Acid-labile groups are also commonly referred to in the art as "acid-cleavable groups," "acid-cleavable protecting groups," "acid-labile protecting groups," "acid-leaving groups," "acid-decomposable groups," and "acid-sensitive groups."

As used herein, when a definition is not otherwise provided, a "divalent linking group" refers to a divalent group including one or more of —O—, —S—, —Te—, —Se—, —C(O)—, —N($R^a$)—, —S(O)—, —S(O)$_2$—, —C(S)—, —C(Te)—, —C(Se)—, substituted or unsubstituted $C_{1-30}$ alkylene, substituted or unsubstituted $C_{3-30}$ cycloalkylene, substituted or unsubstituted $C_{3-30}$ heterocycloalkylene, substituted or unsubstituted $C_{6-30}$ arylene, substituted or unsubstituted $C_{3-30}$ heteroarylene, or a combination thereof, wherein $R^a$ is hydrogen, substituted or unsubstituted $C_{1-20}$ alkyl, substituted or unsubstituted $C_{1-20}$ heteroalkyl, substituted or unsubstituted $C_{6-30}$ aryl, or substituted or unsubstituted $C_{3-30}$ heteroaryl. Typically, the divalent linking group includes one or more of —O—, —S—, —C(O)—, —N($R^a$)—, —S(O)—, —S(O)$_2$—, substituted or unsubstituted $C_{1-30}$ alkylene, substituted or unsubstituted $C_{3-30}$ cycloalkylene, substituted or unsubstituted $C_{3-30}$ heterocycloalkylene, substituted or unsubstituted $C_{6-30}$ arylene, substituted or unsubstituted $C_{3-30}$ heteroarylene, or a combination thereof, wherein $R^a$ is hydrogen, substituted or unsubstituted $C_{1-20}$ alkyl, substituted or unsubstituted $C_{1-20}$ heteroalkyl, substituted or unsubstituted $C_{6-30}$ aryl, or substituted or unsubstituted $C_{3-30}$ heteroaryl. More typically, the divalent linking group includes at least one of —O—, —C(O)—, —C(O)O—, —N($R^a$)—, —C(O)N($R^a$)—, substituted or unsubstituted $C_{1-10}$ alkylene, substituted or unsubstituted $C_{3-10}$ cycloalkylene, substituted or unsubstituted $C_{3-10}$ heterocycloalkylene, substituted or unsubstituted $C_{6-10}$ arylene, substituted or unsubstituted $C_{3-10}$ heteroarylene, or a combination thereof, wherein $R^a$ is hydrogen, substituted or unsubstituted $C_{1-10}$ alkyl, substituted or unsubstituted $C_{1-10}$ heteroalkyl, substituted or unsubstituted $C_{6-10}$ aryl, or substituted or unsubstituted $C_{3-10}$ heteroaryl.

The present invention relates to photoactive compounds, for example photodecomposable quencher (PDQ) compounds. In particular, the inventive photoactive compounds are salts comprising a α,β-unsaturated carboxylate that can be used in photoresist compositions to achieve improved roughness of the printed features and wider DOF.

The photoactive of compounds are of formula (1a) or (1b):

(1a)

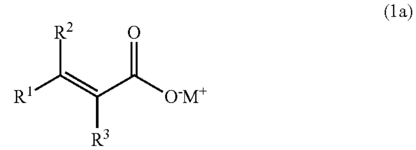

(1b)

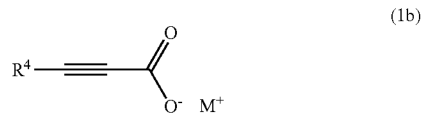

In formula (1a), $R^1$ is substituted or unsubstituted $C_{1-30}$ alkyl, substituted or unsubstituted $C_{3-30}$ cycloalkyl, substituted or unsubstituted $C_{3-30}$ heterocycloalkyl, substituted or unsubstituted $C_{6-30}$ aryl, or substituted or unsubstituted $C_{3-30}$ heteroaryl comprising an aromatic ring heteroatom chosen from nitrogen, oxygen, or a combination thereof. Preferably, $R^1$ may be substituted or unsubstituted $C_{3-20}$ cycloalkyl, substituted or unsubstituted $C_{3-20}$ heterocycloalkyl, substituted or unsubstituted $C_{6-20}$ aryl, or substituted or unsubstituted $C_{3-20}$ heteroaryl comprising an aromatic ring heteroatom chosen from nitrogen or oxygen, and typically $R^1$ may be substituted or unsubstituted $C_{6-20}$ aryl, or substituted or unsubstituted $C_{3-20}$ heteroaryl comprising an aromatic ring heteroatom chosen from nitrogen or oxygen, wherein the substituted $C_{6-20}$ aryl and the substituted $C_{3-20}$ heteroaryl each independently may be substituted with at least one of a halogen, a hydroxyl group, substituted or unsubstituted $C_{1-10}$ alkyl, substituted or unsubstituted $C_6$-$C_{20}$ aryl, substituted or unsubstituted $C_6$-$C_{20}$ aryloxy, substituted or unsubstituted $C_3$-$C_{20}$ heteroaryl, or a group of formula —C(O)OR$^8$, wherein $R^8$ may be substituted or unsubstituted $C_{1-10}$ alkyl, substituted or unsubstituted $C_{3-10}$ cycloalkyl, substituted or unsubstituted $C_{6-10}$ aryl, or substituted or unsubstituted $C_{3-10}$ heteroaryl.

In formula (1a), $R^2$ is hydrogen, halogen, substituted or unsubstituted $C_{1-30}$ alkyl, substituted or unsubstituted $C_{1-30}$ heteroalkyl, substituted or unsubstituted $C_{3-30}$ cycloalkyl, substituted or unsubstituted $C_{3-30}$ heterocycloalkyl, substituted or unsubstituted $C_{2-30}$ alkenyl, substituted or unsubstituted $C_{2-30}$ alkynyl, substituted or unsubstituted $C_1$-$C_{30}$ alkoxy group, substituted or unsubstituted $C_1$-$C_{30}$ alkylthio group, substituted or unsubstituted $C_3$-$C_{10}$ cycloalkenyl group, substituted or unsubstituted $C_3$-$C_{10}$ heterocycloalkenyl group, substituted or unsubstituted $C_{6-30}$ aryl, substituted or unsubstituted $C_{7-30}$ arylalkyl, substituted or unsubstituted $C_{7-30}$ alkylaryl, or substituted or unsubstituted $C_6$-$C_{30}$ aryloxy group. Preferably, $R^2$ may be hydrogen, halogen, or substituted or unsubstituted $C_{1-10}$ alkyl, and typically $R^2$ may be hydrogen.

In formula (1a), each of $R^2$ and $R^3$ optionally further comprises one or more divalent linking groups as part of their structure, wherein each of the one or more divalent linking groups is independently substituted or unsubstituted.

In formula (1a), $R^2$ and $R^3$ together optionally form a ring that optionally further comprises one or more divalent linking groups as part of its structure, wherein each of the one or more divalent linking groups is substituted or unsubstituted, and wherein the ring is substituted or unsubstituted.

In formula (1a), $R^3$ is hydrogen or a non-hydrogen substituent. For example, $R^3$ may be hydrogen or a substituted or unsubstituted $C_{1-20}$ organic group. In some embodiments, $R^3$ may be a $C_{1-20}$ organic group that further comprises —C(O)—, —C(O)O—, —C(O)N($R^5$)—, or a combination thereof, wherein $R^5$ is hydrogen, substituted or unsubstituted $C_{1-10}$ alkyl, substituted or unsubstituted $C_{1-10}$ heteroalkyl, substituted or unsubstituted $C_{6-10}$ aryl, or substituted or unsubstituted $C_{3-10}$ heteroaryl. In other embodiments, $R^3$ may be a halogen atom, a cyano group, or substituted or unsubstituted $C_{1-5}$ haloalkyl. In some aspects, $R^3$ is not hydrogen or a halogen when $R^1$ is the substituted or unsubstituted $C_{6-30}$ aryl.

In formula (1b), $R^4$ is substituted or unsubstituted $C_{1-30}$ alkyl, substituted or unsubstituted $C_{3-30}$ cycloalkyl, substituted or unsubstituted $C_{3-30}$ heterocycloalkyl, substituted or unsubstituted $C_{6-30}$ aryl, or substituted or unsubstituted $C_{3-30}$ heteroaryl. Preferably, $R^4$ may be substituted or unsubstituted $C_{3-20}$ cycloalkyl, substituted or unsubstituted $C_{3-20}$ heterocycloalkyl, substituted or unsubstituted $C_{6-20}$ aryl, or substituted or unsubstituted $C_{3-20}$ heteroaryl. For example, $R^4$ may be substituted or unsubstituted $C_{6-18}$ aryl, or substituted or unsubstituted $C_{3-18}$ heteroaryl, wherein the substituted $C_{6-18}$ aryl and the substituted $C_{3-18}$ heteroaryl are each substituted with at least one of halogen, amino (—$NH_2$), mono- or di-($C_{1-6}$)alkylamino, substituted or unsubstituted $C_{1-6}$ alkyl, substituted or unsubstituted $C_{1-6}$ haloalkyl, substituted or unsubstituted $C_{1-9}$ alkoxy, substituted or unsubstituted $C_{2-6}$ alkenyl, substituted or unsubstituted $C_{6-12}$ aryl, substituted or unsubstituted $C_{3-12}$ heteroaryl, or a combination thereof. $R^4$ optionally further includes one or more divalent linking groups as part of its structure, wherein each of the one or more divalent linking groups is independently substituted or unsubstituted.

In formulae (1a) and (1b), $M^+$ is an organic cation. For example, $M^+$ may be a sulfonium cation or an iodonium cation. In some embodiments, $M^+$ may be a sulfonium cation of formula (2a) or an iodonium cation of formula (2b):

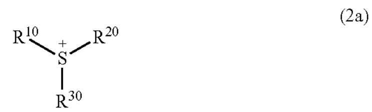

(2a)

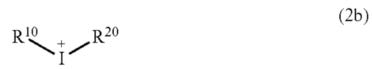

(2b)

In formulae (2a) and (2b), $R^{10}$, $R^{20}$, and $R^{30}$ each independently may be substituted or unsubstituted $C_{1-20}$ alkyl, substituted or unsubstituted $C_{3-20}$ cycloalkyl, substituted or unsubstituted $C_{2-20}$ alkenyl, substituted or unsubstituted $C_{6-30}$ aryl, substituted or unsubstituted $C_{6-30}$ iodoaryl, substituted or unsubstituted $C_{3-30}$ heteroaryl, substituted or unsubstituted $C_{7-20}$ arylalkyl, or substituted or unsubstituted $C_{4-20}$ heteroarylalkyl. Each of $R^{10}$, $R^{20}$, and $R^{30}$ may be either separate or connected to another group of $R^{10}$, $R^{20}$, or $R^{30}$ via a single bond or a divalent linking group to form a ring. Each of $R^{10}$, $R^{20}$, and $R^{30}$ optionally may include as part of its structure a divalent linking group. Each of $R^{10}$, $R^{20}$, and $R^{30}$ independently may optionally comprise an acid-labile group chosen, for example, from tertiary alkyl ester groups, secondary or tertiary aryl ester groups, secondary or tertiary ester groups having a combination of alkyl and aryl groups, tertiary alkoxy groups, acetal groups, or ketal groups. Suitable divalent linking groups for connection of $R^{10}$, $R^{20}$, and/or $R^{30}$ groups include, for example, —O—, —S—, —Te—, —Se—, —C(O)—, —C(S)—, —C(Te)—, or —C(Se)—, substituted or unsubstituted $C_{1-5}$ alkylene, or a combination thereof.

Exemplary sulfonium cations of formula (2a) include the following:

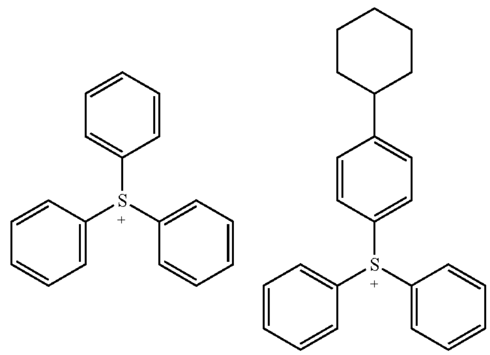

-continued
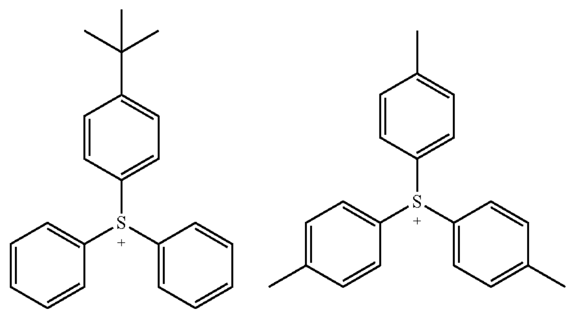
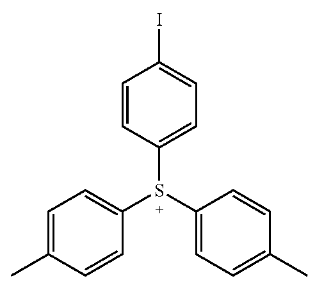
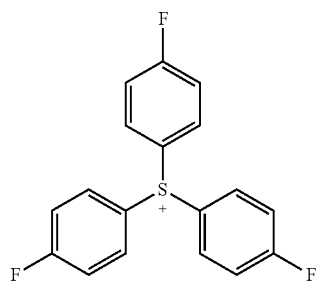
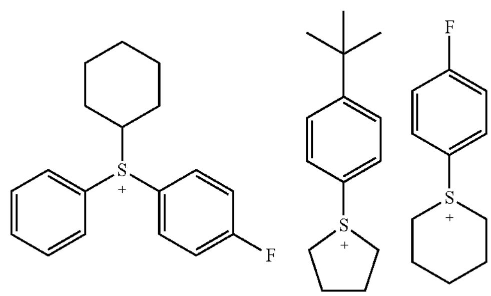
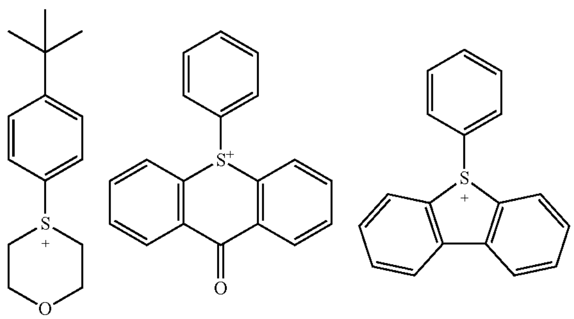
-continued
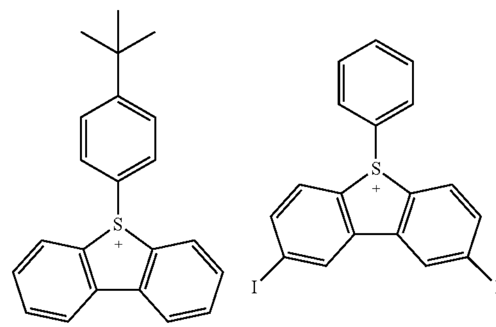
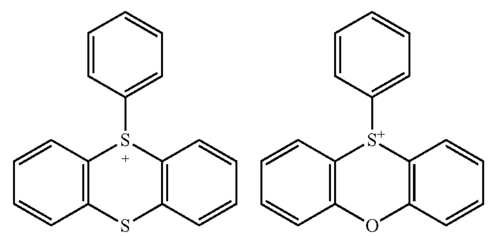
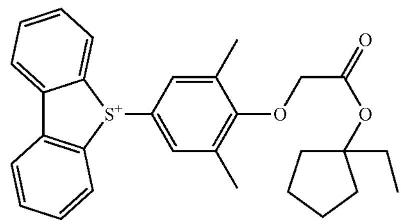
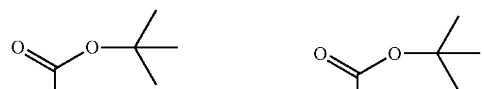
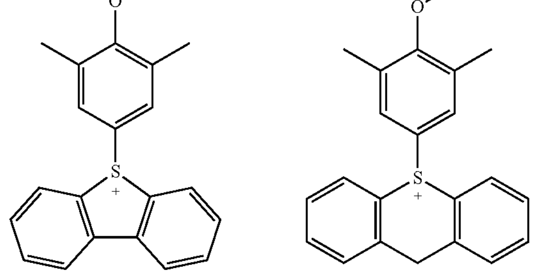
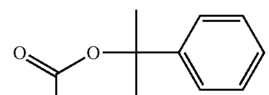
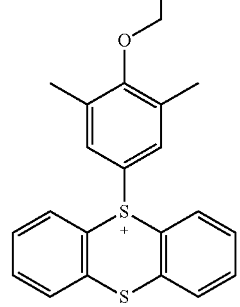

-continued
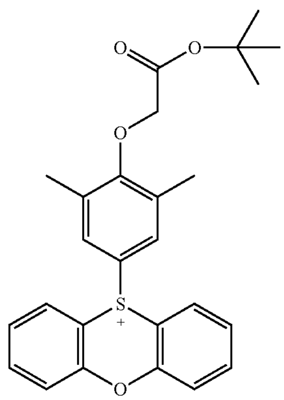
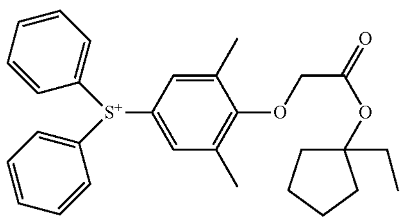
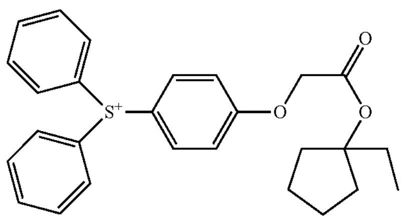
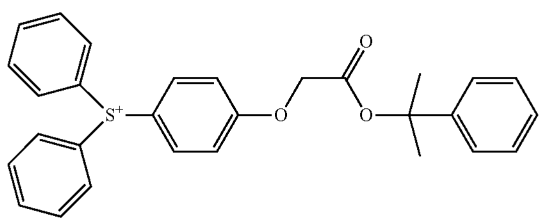
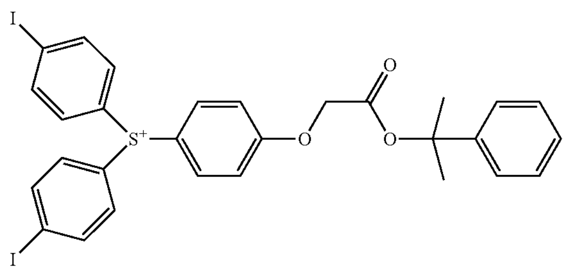
-continued
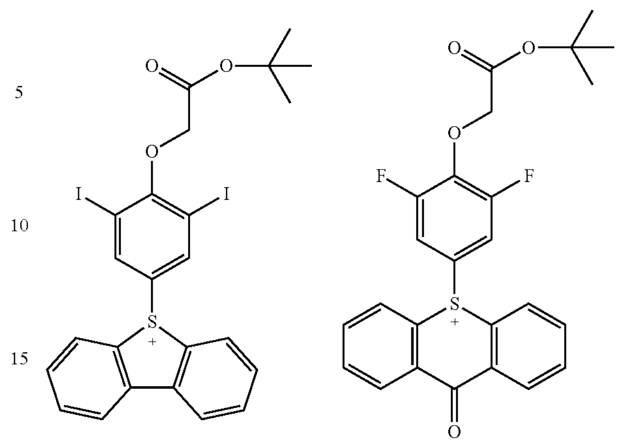
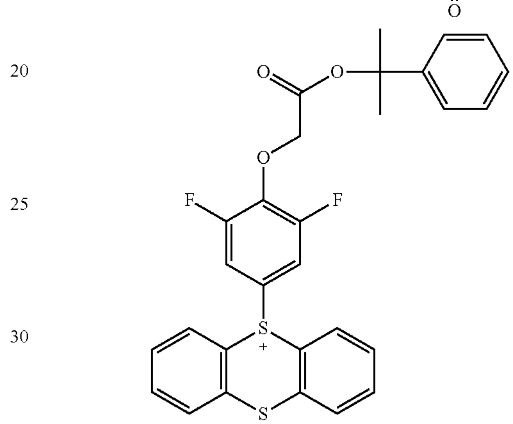
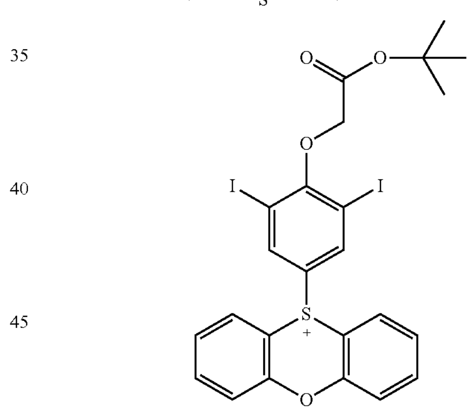
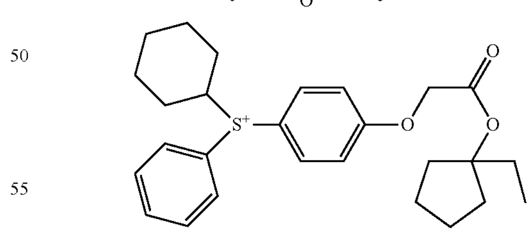
Exemplary iodonium cations of formula (2b) include the following:
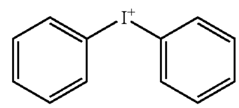

-continued

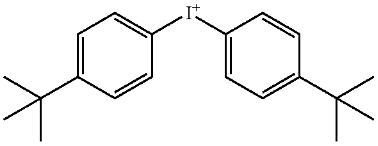

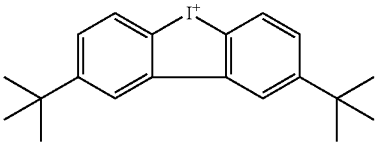

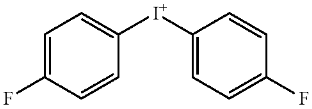

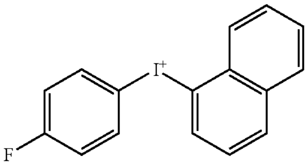

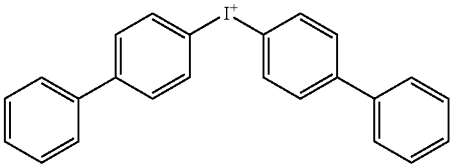

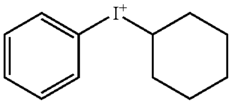

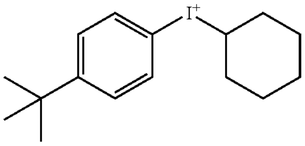

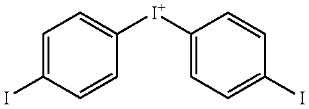

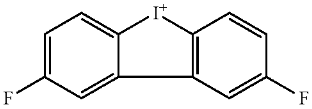

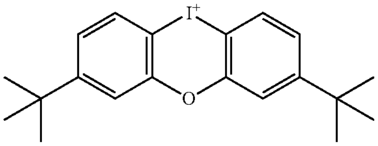

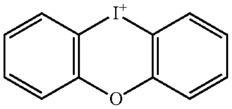

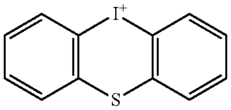

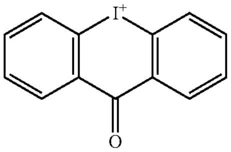

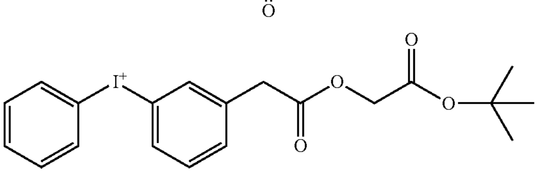

-continued

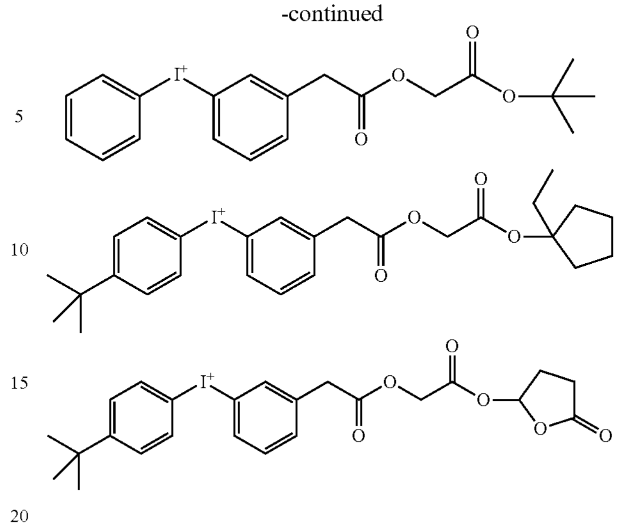

In some aspects, the photoactive compound of formula (1a) may be represented by formula (3a):

(3a)

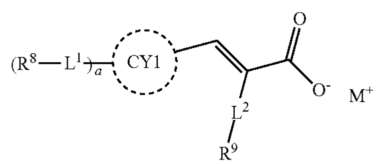

In formula (3a), ring CY1 may be a $C_{3-30}$ carbocyclic group or a $C_{3-30}$ heterocyclic group. Preferably, ring CY1 is $C_{3-8}$ cycloalkyl, $C_{6-14}$ aryl, or $C_{3-12}$ heteroaryl comprising an aromatic ring heteroatom chosen from nitrogen, oxygen, or a combination thereof.

In formula (3a), each $L^1$ independently may be a single bond or a divalent linking group.

In formula (3a), each $R^8$ independently may be hydroxyl, —F, —I, —$CF_3$, substituted or unsubstituted $C_{1-10}$ alkyl, substituted or unsubstituted $C_{3-20}$ cycloalkyl, substituted or unsubstituted $C_{3-20}$ heterocycloalkyl, substituted or unsubstituted $C_{6-10}$ aryl, or substituted or unsubstituted $C_{3-10}$ heteroaryl.

In formula (3a), a is an integer from 0 to 10. Preferably, a is an integer from 0 to 5, and typically a is an integer from 0 to 3.

In formula (3a), $L^2$ is a single bond, —C(O)—, —C(O)O—, or —C(O)N($R^{5a}$)—, wherein $R^{5a}$ is hydrogen, substituted or unsubstituted $C_{1-10}$ alkyl, substituted or unsubstituted $C_{1-10}$ heteroalkyl, substituted or unsubstituted $C_{6-10}$ aryl, or substituted or unsubstituted $C_{3-10}$ heteroaryl.

In formula (3a), $R^9$ may be hydrogen, cyano, hydroxyl, —F, —I, —$CF_3$, substituted or unsubstituted $C_{1-10}$ alkyl, substituted or unsubstituted $C_{3-20}$ cycloalkyl, substituted or unsubstituted $C_{3-20}$ heterocycloalkyl, substituted or unsubstituted $C_{6-10}$ aryl, or substituted or unsubstituted $C_{3-10}$ heteroaryl. In some embodiments, when $R^9$ is the substituted $C_{1-10}$ alkyl, substituted $C_{3-20}$ cycloalkyl, substituted $C_{3-20}$ heterocycloalkyl, substituted $C_{6-10}$ aryl, or substituted $C_{3-10}$ heteroaryl, at least one substituent of the substituted $R^9$ group may be hydroxy, —I, or a combination thereof.

In formula (3a), $M^+$ is the same as defined in formula (1a).

In some aspects, the photoactive compound of formula (1b) may be represented by formula (3b):

(3b)

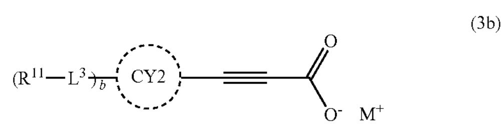

In formula (3b), ring CY2 may be a $C_{3-30}$ carbocyclic group or a $C_{3-30}$ heterocyclic group. Preferably, ring CY2 is $C_{3-8}$ cycloalkyl, $C_{6-14}$ aryl, or $C_{3-12}$ heteroaryl comprising an aromatic ring heteroatom chosen from nitrogen, oxygen, or a combination thereof.

In formula (3b), b is an integer from 0 to 10. Preferably, b is an integer from 0 to 5, and typically b is an integer from 0 to 3.

In formula (3b), $L^3$ is a single bond, —C(O)—, —C(O)O—, or —C(O)N($R^b$)—, wherein $R^{5b}$ is hydrogen, substituted or unsubstituted $C_{1-10}$ alkyl, substituted or unsubstituted $C_{1-10}$ heteroalkyl, substituted or unsubstituted $C_{6-10}$ aryl, or substituted or unsubstituted $C_{3-10}$ heteroaryl.

In formula (3b), $R^{11}$ may be hydrogen, cyano, hydroxyl, —F, —I, —$CF_3$, substituted or unsubstituted $C_{1-10}$ alkyl, substituted or unsubstituted $C_{3-20}$ cycloalkyl, substituted or unsubstituted $C_{3-20}$ heterocycloalkyl, substituted or unsubstituted $C_{6-10}$ aryl, or substituted or unsubstituted $C_{3-10}$ heteroaryl. In some embodiments, when $R^9$ is the substituted $C_{1-10}$ alkyl, substituted $C_{3-20}$ cycloalkyl, substituted $C_{3-20}$ heterocycloalkyl, substituted $C_{6-10}$ aryl, or substituted $C_{3-10}$ heteroaryl, at least one substituent of the substituted $R^9$ group may be hydroxy, —I, or a combination thereof.

In formula (3b), $M^+$ is the same as defined in formula (1b).

Non-limiting examples of the anion portion of the photoactive compounds of formula (1a) may include one or more of the following compounds:

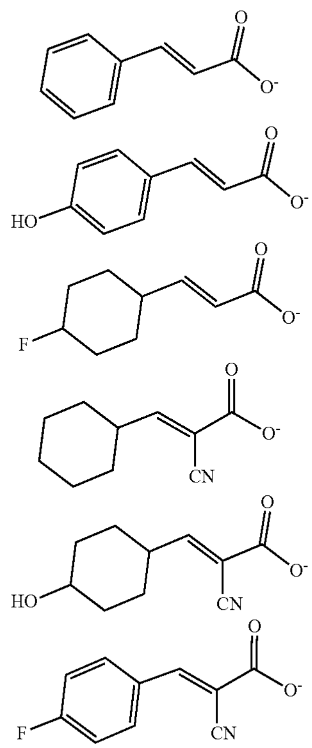

-continued

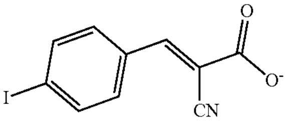

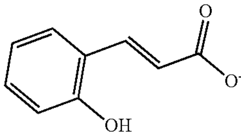

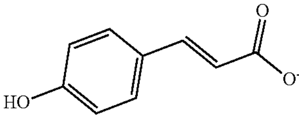

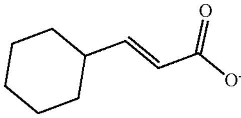

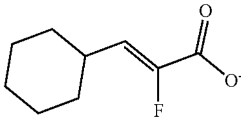

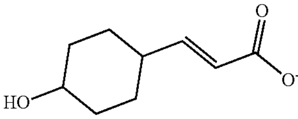

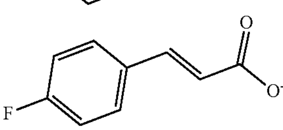

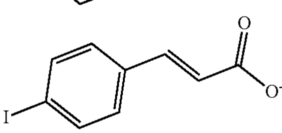

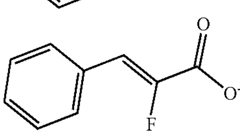

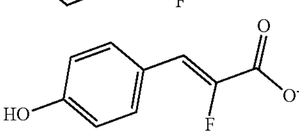

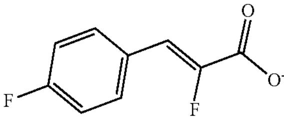

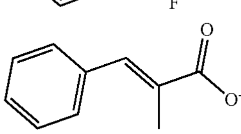

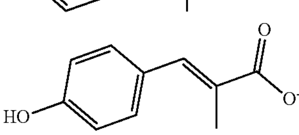

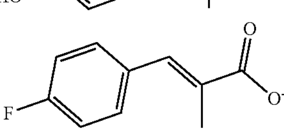

-continued
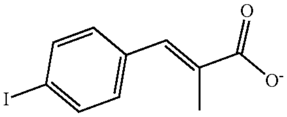
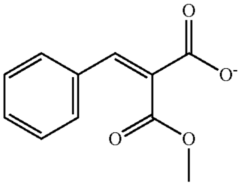
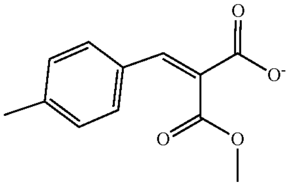
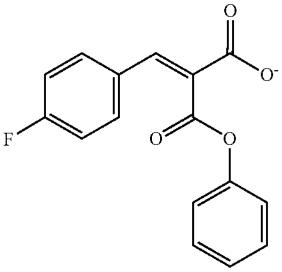
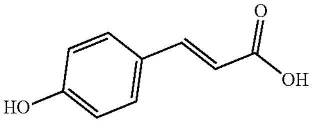
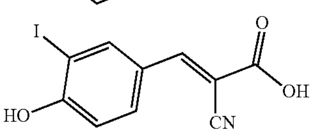
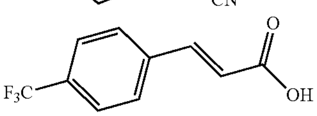
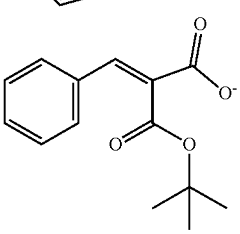
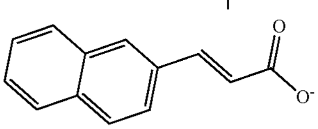
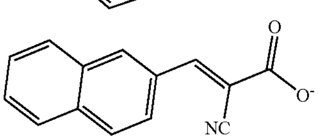
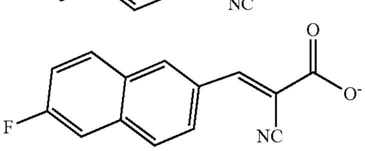
-continued
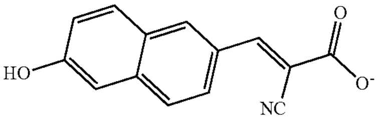
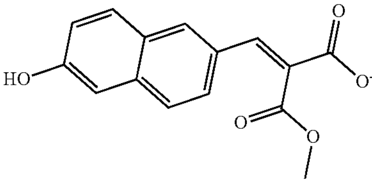
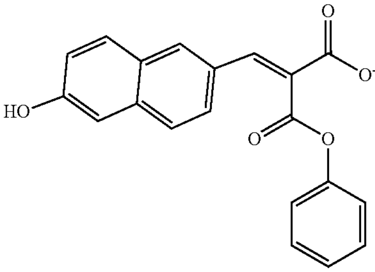
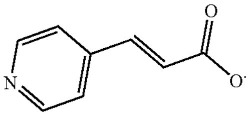
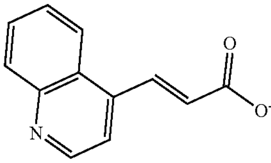
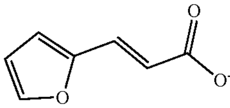
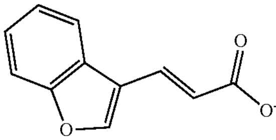
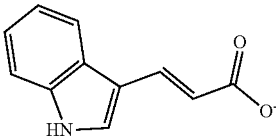
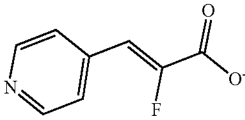
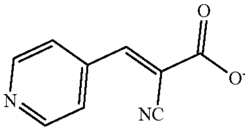
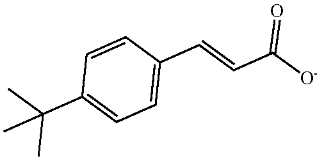
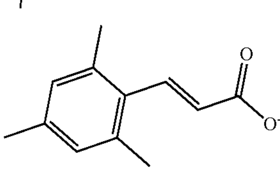
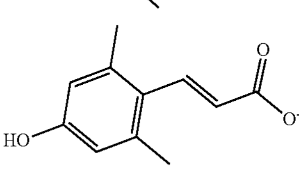

-continued
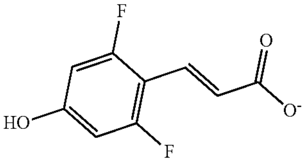
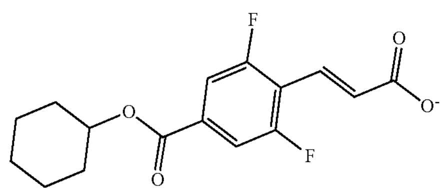
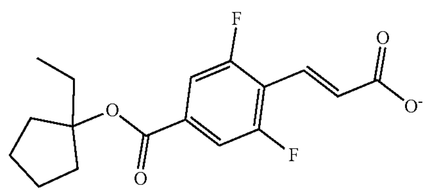
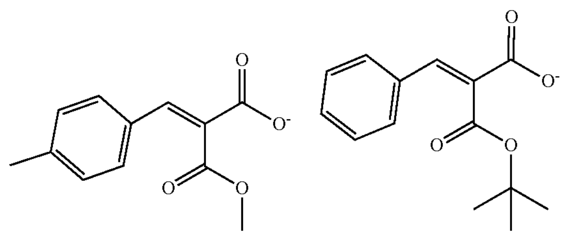
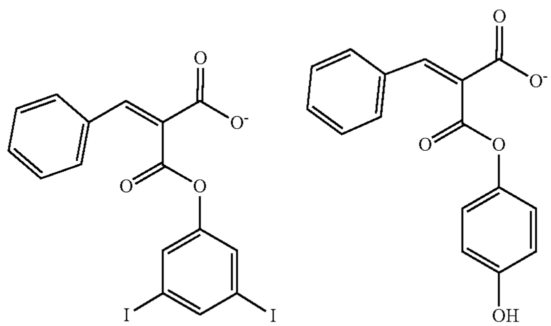
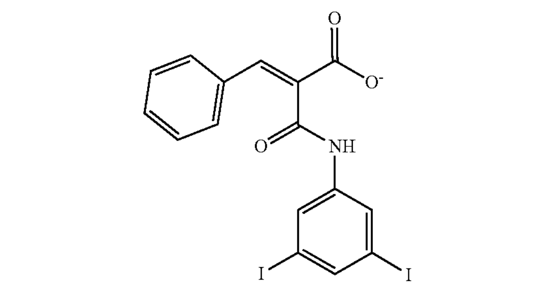
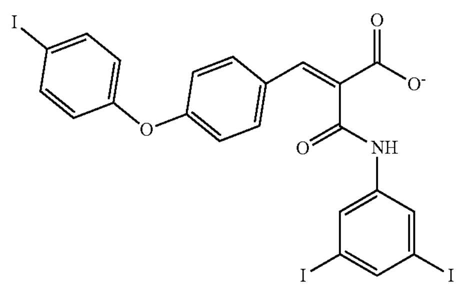
-continued
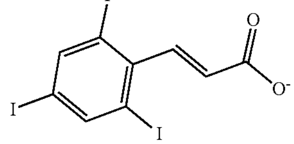
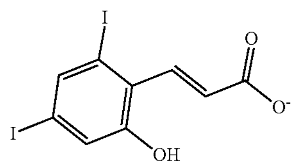
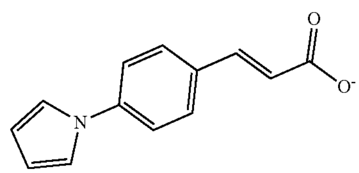
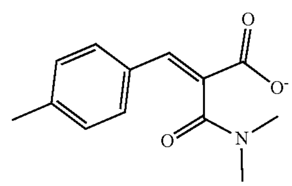
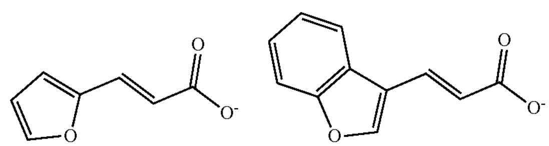
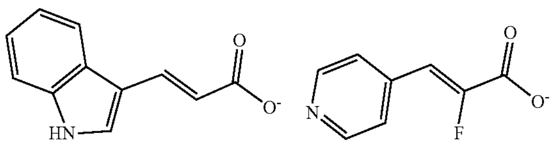
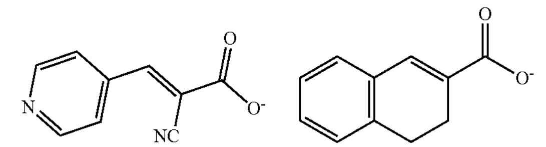
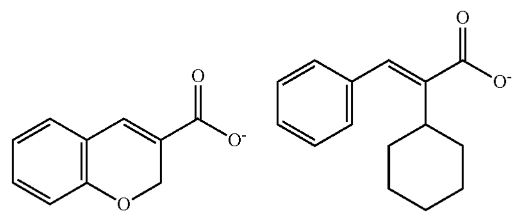
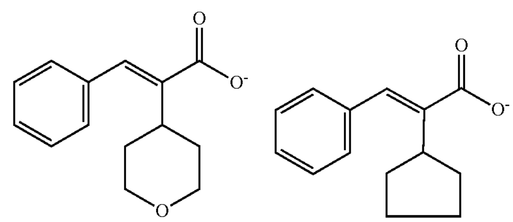
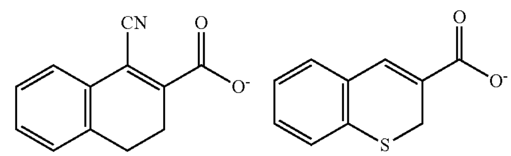

-continued
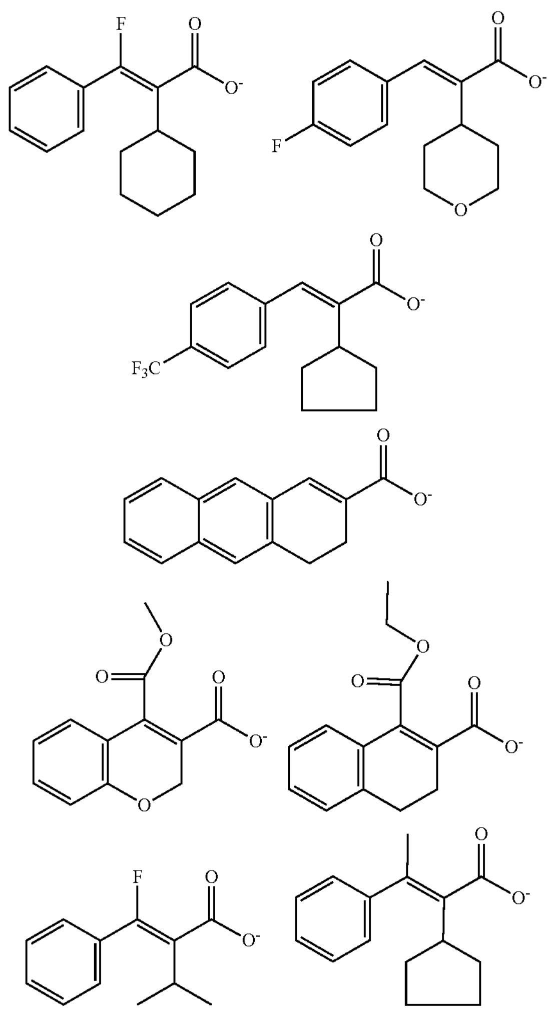
Non-limiting examples of the anion portion of the photoactive compounds of formula (1b) may include one or more of the following compounds:
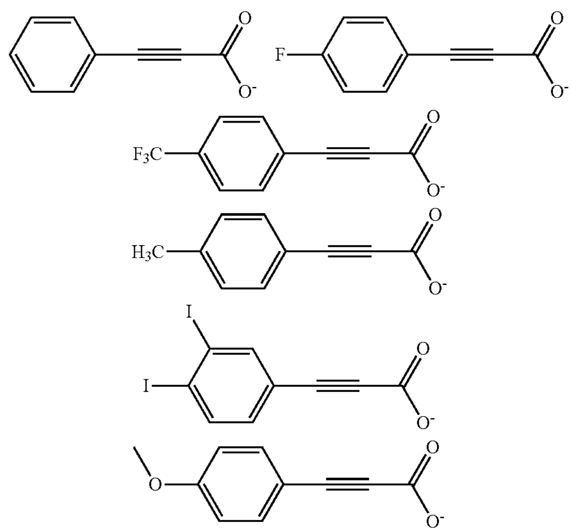
-continued
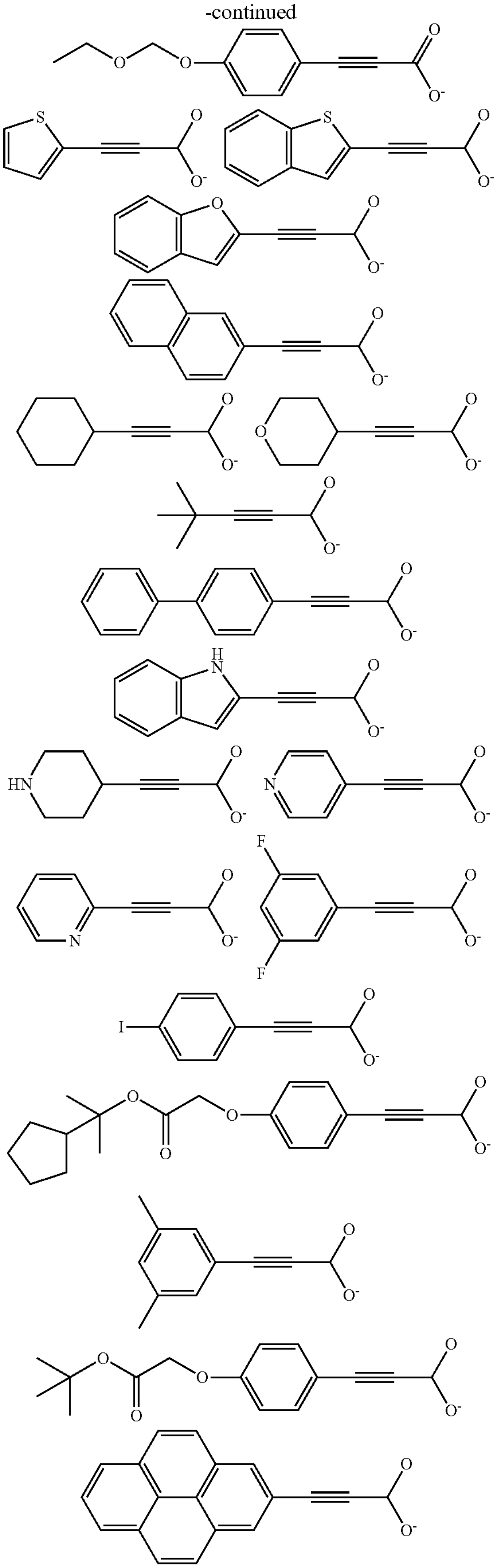

-continued

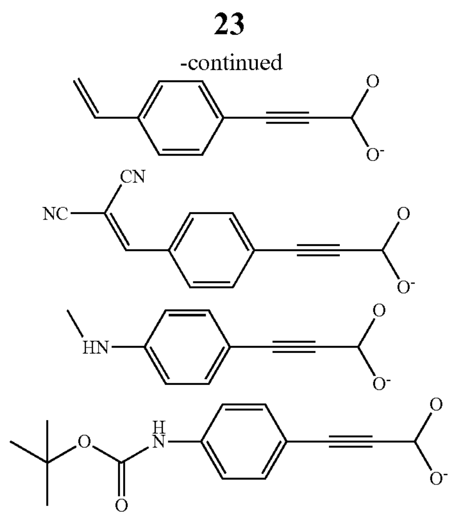

The present invention further relates to photoresist compositions that include the photoactive compound and a solvent, and may contain additional, optional components. Typically, the photoresist composition will further include a polymer, a photoacid generator (PAG), or a combination thereof.

According to an aspect, the photoresist composition further includes a material that switches solubility in a base or in an organic solvent under action of acid, wherein the material is different from the photoactive compound. For example, the material may be a polymer or a molecular glass.

The polymer may include one or more repeating units. The repeating units may be, for example, one or more units for purposes of adjusting properties of the photoresist composition, such as etch rate and solubility. Exemplary repeating units may include those derived from one or more of (meth)acrylate, vinyl aromatic, vinyl ether, vinyl ketone, and/or vinyl ester monomers.

In some embodiments, the polymer may include a repeating unit including an acid-labile group. For example, the repeating unit including the acid-labile group may be derived from one or more monomers of formulae (4), (5), or (6):

(4)

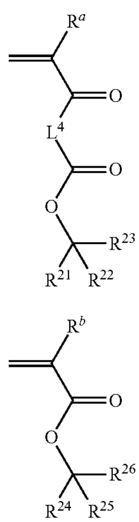

(5)

-continued (6)

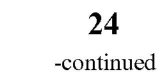

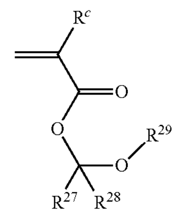

(7)

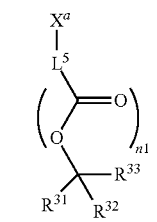

(8)

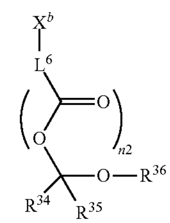

In formulae (4), (5), and (6), $R^a$ to $R^e$ may each independently be hydrogen, fluorine, cyano, or substituted or unsubstituted $C_{1-10}$ alkyl. Preferably, $R^a$ to $R^e$ may each independently be hydrogen, fluorine, or substituted or unsubstituted $C_{1-5}$ alkyl, typically methyl.

In formula (4), $L^4$ is a divalent linking group. For example, $L^4$ may include 1 to 10 carbon atoms and at least one heteroatom. In a typical example, $L^4$ may be $—OCH_2—$, $—OCH_2CH_2O—$, or $—N(R^{5c})—$, wherein $R^{5c}$ is hydrogen or $C_{1-6}$ alkyl.

In formulae (4) and (5), $R^{21}$ to $R^{26}$ are each independently hydrogen, substituted or unsubstituted $C_{1-20}$ alkyl, substituted or unsubstituted $C_{3-20}$ cycloalkyl, substituted or unsubstituted $C_{3-20}$ heterocycloalkyl, substituted or unsubstituted $C_{2-20}$ alkenyl, substituted or unsubstituted $C_{3-20}$ cycloalkenyl, substituted or unsubstituted $C_{3-20}$ heterocycloalkenyl, substituted or unsubstituted $C_{6-20}$ aryl, or substituted or unsubstituted $C_{3-20}$ heteroaryl, provided that no more than one of $R^{21}$ to $R^{23}$ may be hydrogen, and no more than one of $R^{24}$ to $R^{26}$ may be hydrogen, and provided that if one of $R^{21}$ to $R^{23}$ is hydrogen, then at least one of the others from $R^{21}$ to $R^{23}$ is substituted or unsubstituted $C_{6-20}$ aryl or substituted or unsubstituted $C_{3-20}$ heteroaryl, and if one of $R^{24}$ to $R^{26}$ is hydrogen, then at least one of the others from $R^{24}$ to $R^{26}$ is substituted or unsubstituted $C_{6-20}$ aryl or substituted or unsubstituted $C_{3-20}$ heteroaryl. Preferably, $R^{21}$ to $R^{26}$ are each independently substituted or unsubstituted $C_{1-6}$ alkyl or substituted or unsubstituted $C_{3-10}$ cycloalkyl. Each of $R^{21}$ to $R^{26}$ may optionally further comprise a divalent linking group as part of their structure.

In formula (4), any two of $R^{21}$ to $R^{23}$ together optionally may form a ring via a single bond or a divalent linking group, wherein the ring may be substituted or unsubstituted. In formula (5), any two of $R^{24}$ to $R^{26}$ together optionally may form a ring via a single bond or a divalent linking group, wherein the ring may be substituted or unsubstituted.

For example, any one or more of $R^{21}$ to $R^{26}$ may be independently a group of the formula $—CH_2C(=O)$ $CH_{(3-n)}Y_n$, where each Y is independently substituted or unsubstituted $C_{2-10}$ heterocycloalkyl and n is 1 or 2. For example, each Y may be independently substituted or unsubstituted $C_{2-10}$ heterocycloalkyl including a group of the formula —$O(C^{a1})(C^{a2})O$—, wherein $C^{a1}$ and $C^{a2}$ are each independently hydrogen or substituted or unsubstituted alkyl, and where $C^{a1}$ and $C^{a2}$ together optionally form a ring.

In formulae (6) and (8), $R^{27}$, $R^{28}$, $R^{34}$, and $R^{35}$ each independently may be hydrogen, substituted or unsubstituted $C_{1-20}$ alkyl, substituted or unsubstituted $C_{3-20}$ cycloalkyl, substituted or unsubstituted $C_{3-20}$ heterocycloalkyl, substituted or unsubstituted $C_{6-20}$ aryl, or substituted or unsubstituted $C_{3-20}$ heteroaryl; and $R^{16}$ and $R^{22}$ are each independently substituted or unsubstituted $C_{1-20}$ alkyl, substituted or unsubstituted $C_{3-20}$ cycloalkyl, or substituted or unsubstituted $C_{3-20}$ heterocycloalkyl. Preferably, $R^{27}$, $R^{28}$, $R^{34}$, and $R^{35}$ each independently may be hydrogen, substituted or unsubstituted $C_{1-20}$ alkyl, substituted or unsubstituted $C_{3-20}$ cycloalkyl, or substituted or unsubstituted $C_{3-20}$ heterocycloalkyl. Each of $R^2$, $R^{28}$, $R^{34}$, and $R^{351}$ may optionally further comprise a divalent linking group as part of their structure.

In formula (7), $R^{31}$ to $R^{33}$ may be each independently be substituted or unsubstituted $C_{1-20}$ alkyl, substituted or unsubstituted $C_{3-20}$ cycloalkyl, substituted or unsubstituted $C_{3-20}$ heterocycloalkyl, substituted or unsubstituted $C_{6-20}$ aryl, or substituted or unsubstituted $C_{3-20}$ heteroaryl, provided that no more than one of $R^{31}$ to $R^{33}$ may be hydrogen and provided that if one of $R^{31}$ to $R^{33}$ is hydrogen, then at least one of the others from $R^{31}$ to $R^{33}$ is substituted or unsubstituted $C_{6-20}$ aryl or substituted or unsubstituted $C_{3-20}$ heteroaryl. Each of $R^{31}$ to $R^{33}$ may optionally further comprise a divalent linking group as part of their structure.

In formula (7), any two of $R^{31}$ to $R^{33}$ together optionally form a ring, which may further include a divalent linking group as part of its structure, wherein the ring group may be substituted or unsubstituted.

In formulae (7) and (8), $X^a$ and $X^b$ are each independently a polymerizable group comprising an ethylenically unsaturated double bond, such as substituted or unsubstituted $C_{2-20}$ alkenyl or substituted or unsubstituted norbornyl, preferably (meth)acrylate or $C_2$ alkenyl.

In formulae (7) and (8), $L^5$ and $L^6$ are each independently a single bond or a divalent linking group, provided that $L^5$ is not a single bond when $X^a$ is $C_2$ alkenyl and that $L^6$ is not a single bond when $X^b$ is $C_2$ alkenyl. Preferably, $L^5$ and $L^6$ are each independently substituted or unsubstituted $C_{6-30}$ arylene or substituted or unsubstituted $C_{6-30}$ cycloalkylene. In formulae (7) and (8), n1 is 0 or 1 and n2 is 0 or 1. It is to be understood that when n1 is 0, the $L^5$ group is connected directly to the oxygen atom. It is to be understood that when n2 is 0, the $L^6$ group is connected directly to the oxygen atom.

In formula (8), any two of $R^{34}$ to $R^{36}$ together optionally may form a ring, which may further include a divalent linking group as part of its structure, wherein the ring group may be substituted or unsubstituted.

In some aspects, each of $R^{21}$ to $R^{29}$ and $R^{31}$ to $R^{36}$ optionally may further include as part of their structure one or more divalent linking groups selected from —O—, —C(O)—, —C(O)O—, —S—, —$S(O)_2$—, —N(R')—, or —C(O)N(R')—, wherein R' may be hydrogen, substituted or unsubstituted $C_{1-20}$ alkyl, substituted or unsubstituted $C_{3-20}$ cycloalkyl, or substituted or unsubstituted $C_{3-20}$ heterocycloalkyl.

In some aspects, in a repeating unit comprising an acid-labile group, the acid-labile group may be a tertiary alkyl ester. For example, a repeating unit comprising a tertiary alkyl ester group may be derived from one or more monomers of formulae (4), (5), or (7), wherein none of $R^{21}$ to $R^{26}$ or $R^{34}$ to $R^{36}$ is hydrogen, and n1 is 1.

Exemplary monomers of formula (4) include one or more of the following:

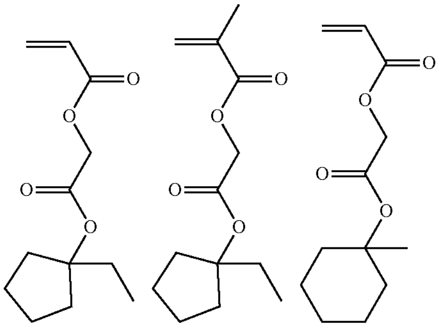

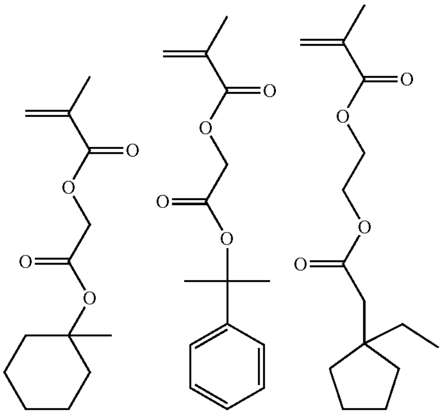

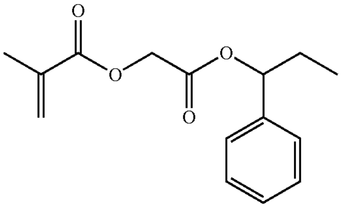

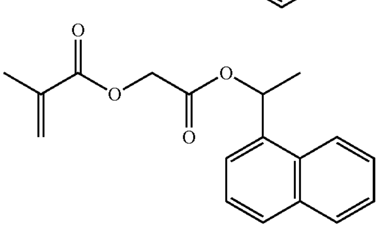

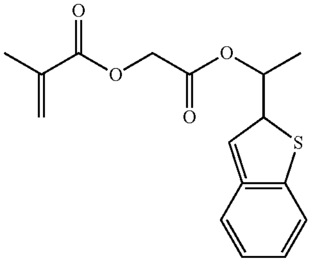

Exemplary monomers of formula (5) include one or more of the following:

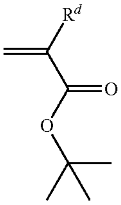 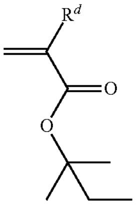 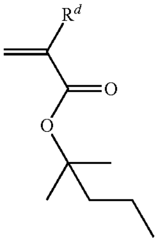
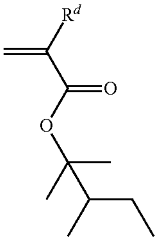 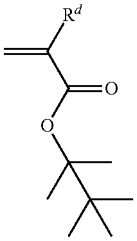 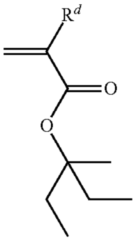
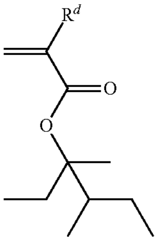 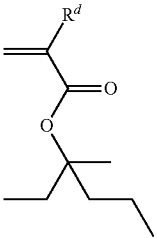 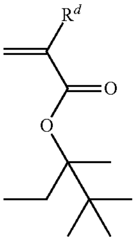
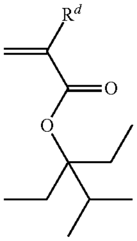 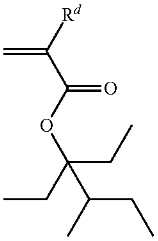 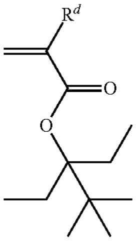
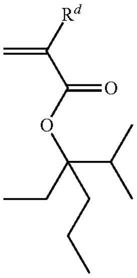 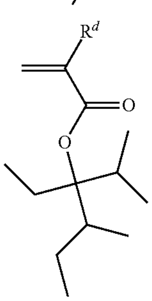 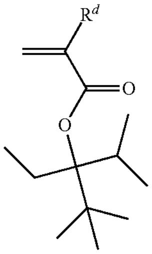
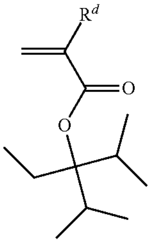 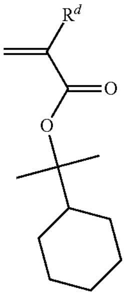 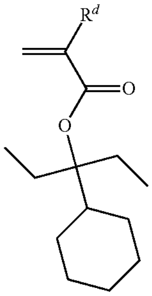
-continued
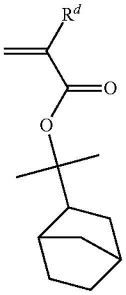 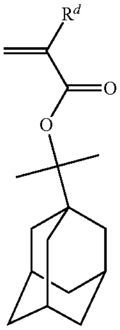 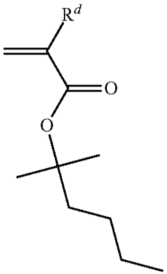
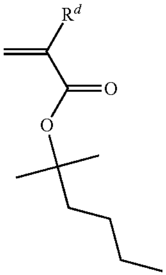 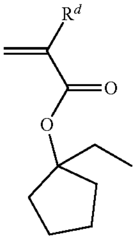 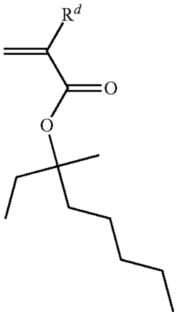
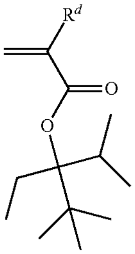 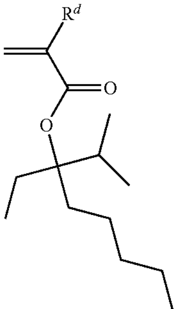 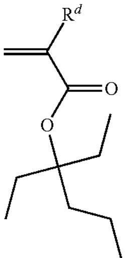
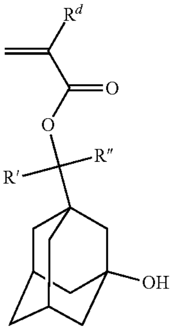 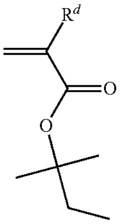 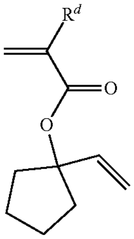
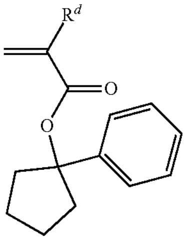 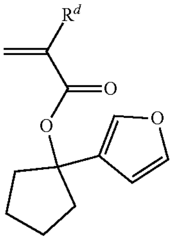 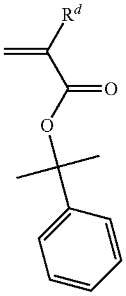

-continued

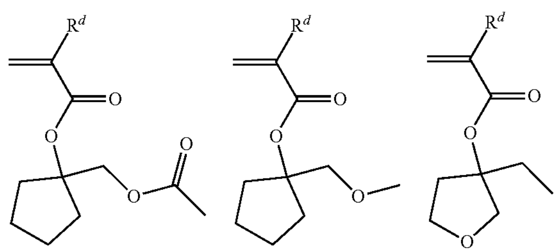

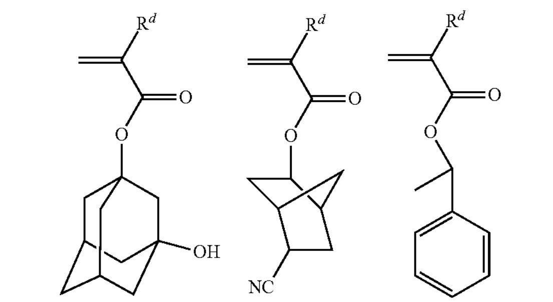

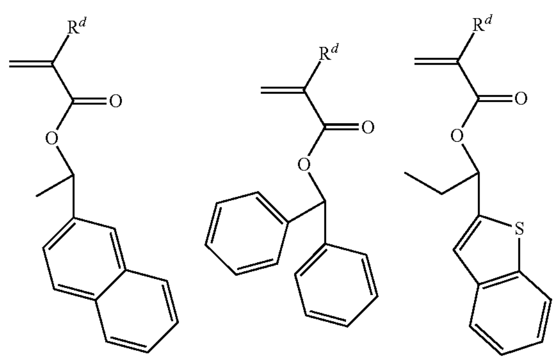

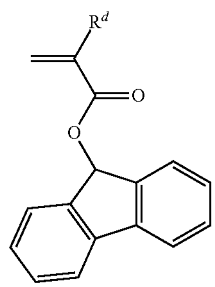

wherein $R^d$ is as defined herein for $R^b$ in formula (3); and R' and R" are each independently substituted or unsubstituted $C_{1-20}$ alkyl, substituted or unsubstituted $C_{3-20}$ cycloalkyl, substituted or unsubstituted $C_{3-20}$ heterocycloalkyl, substituted or unsubstituted $C_{2-20}$ alkenyl, substituted or unsubstituted $C_{3-20}$ cycloalkenyl, substituted or unsubstituted $C_{3-20}$ heterocycloalkenyl, substituted or unsubstituted $C_{6-20}$ aryl, or substituted or unsubstituted $C_{3-20}$ heteroaryl.

Exemplary monomers of formula (6) include one or more of the following:

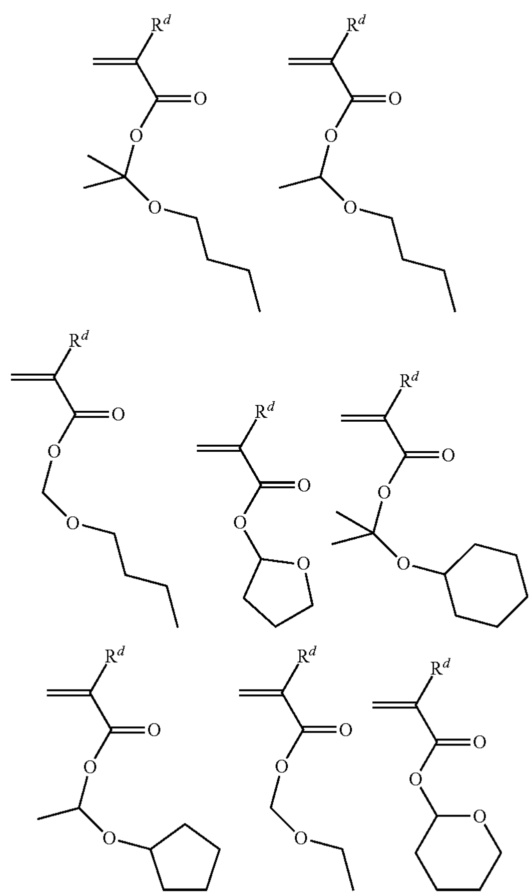

wherein $R^d$ is as defined above for $R^c$.

Exemplary monomers of formula (7) include one or more of the following:

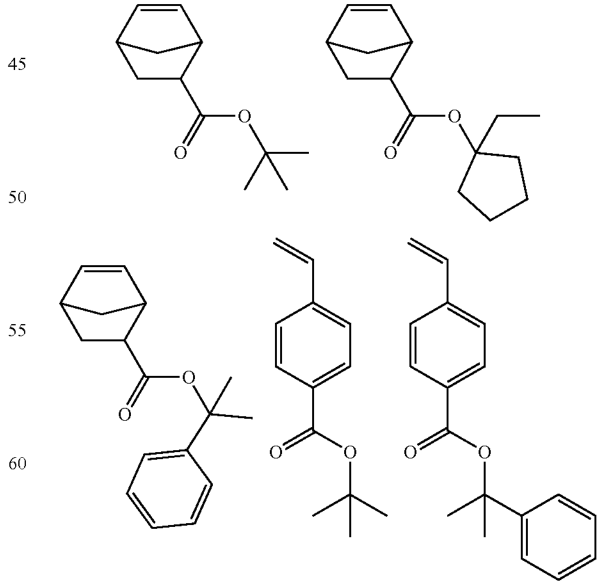

-continued
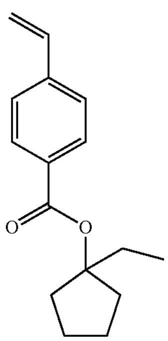
Exemplary monomers of formula (8) include one or more of the following:
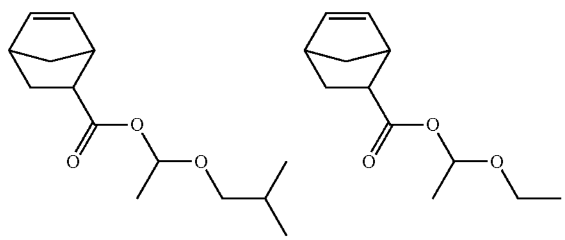
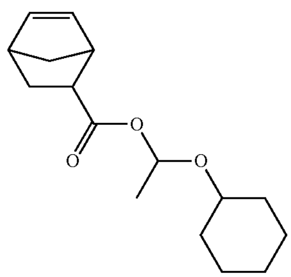
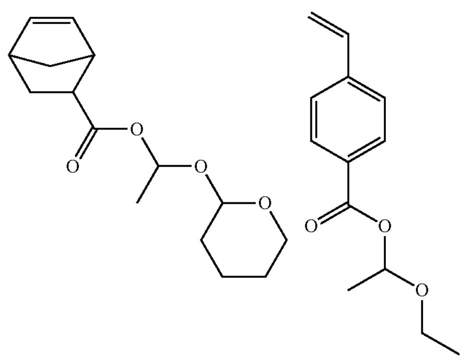
-continued
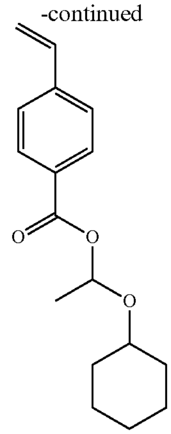
In some aspects, the polymer may have an acid-labile repeating unit that is derived from one or more monomers having a cyclic acetal or cyclic ketal group, for example, having one or more of the following structures:
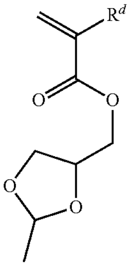
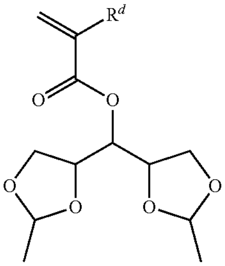
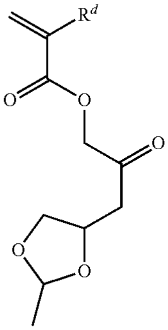
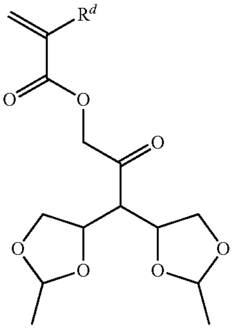
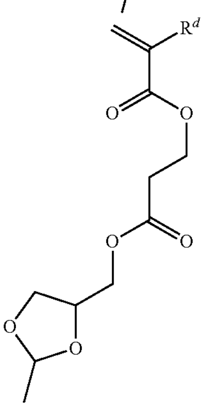
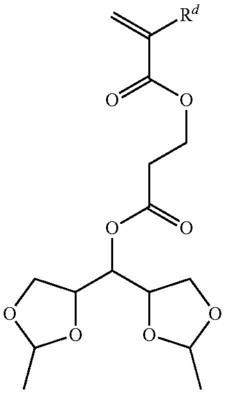
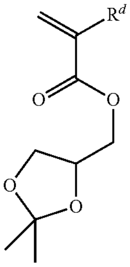

-continued

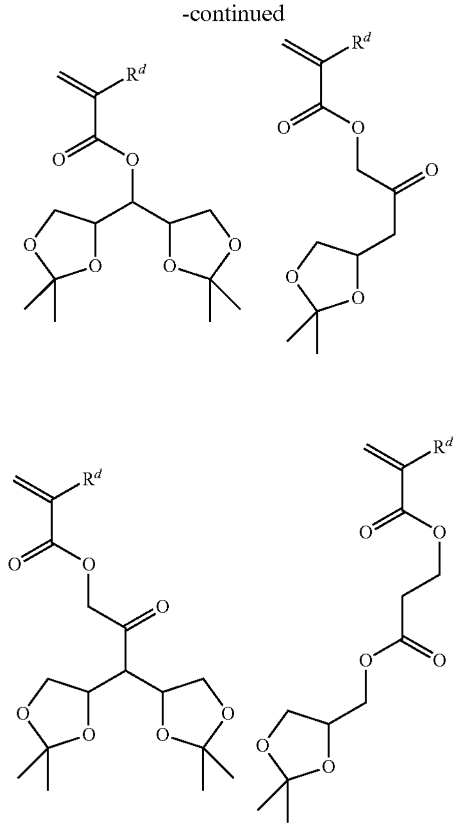

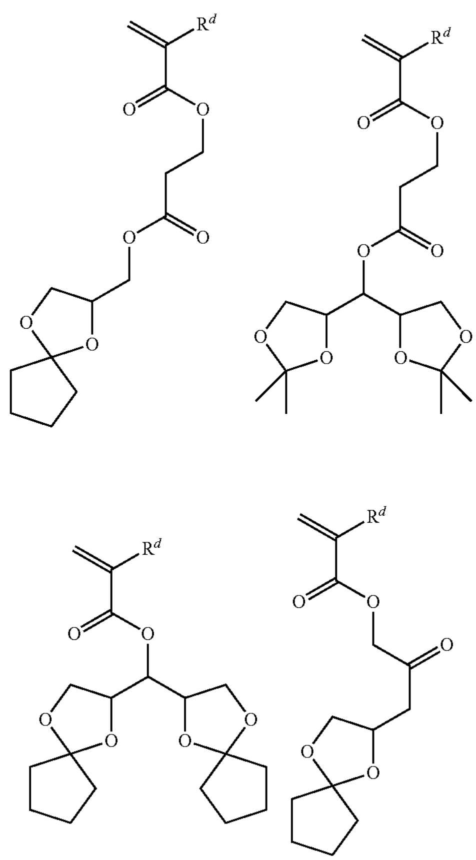

-continued

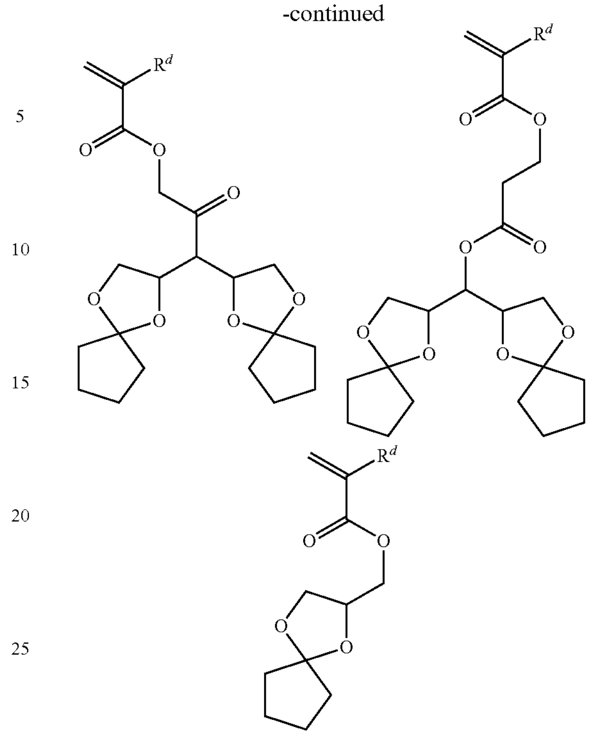

wherein $R^d$ is as defined above for $R^a$.

In some aspects, the polymer may have a repeating unit having an acid-labile group that comprises a tertiary alkoxy group, for example, one or more monomers of the following:

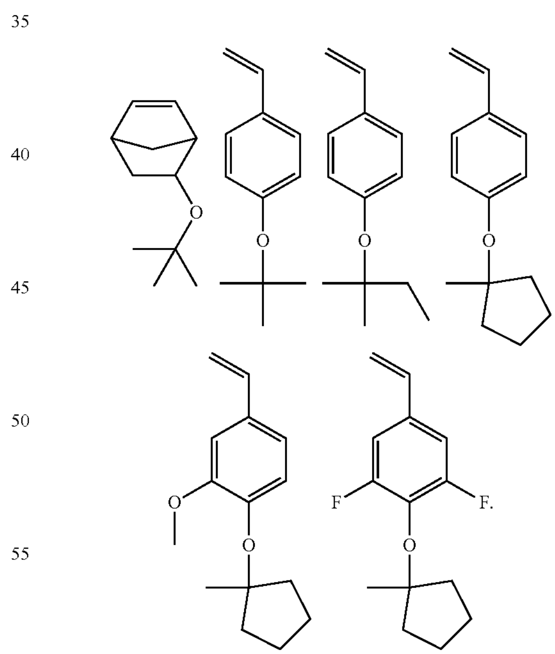

When present, the repeating unit including an acid-labile group is typically included in the polymer in an amount from 5 to 95 mol %, more typically from 20 to 80 mol %, still more typically from 30 to 50 mol %, based on total repeating units in the polymer.

In some aspects, the polymer may further include a repeating unit comprising a polar group, where the polar group is pendant to the backbone of the polymer. For example, the polar group can be a lactone group, a hydroxy aryl group, a fluoroalcohol group, or a combination thereof.

In one or more embodiments, the polymer may further include a third repeating unit derived from one or more lactone-containing monomers of formula (9):

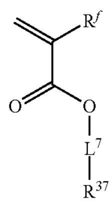

(9)

In formula (9), $R^f$ is hydrogen, fluorine, cyano, or substituted or unsubstituted $C_{1-10}$ alkyl.

In formula (9), $L^7$ is a single bond or a divalent linking group. Preferably, $L^7$ is a single bond or one or more groups selected from substituted or unsubstituted $C_{1-30}$ alkylene, substituted or unsubstituted $C_{1-30}$ heteroalkylene, substituted or unsubstituted $C_{3-30}$ cycloalkylene, substituted or unsubstituted $C_{3-30}$ heterocycloalkylene, substituted or unsubstituted $C_{6-30}$ arylene, substituted or unsubstituted $C_{3-30}$ heteroarylene, —O—, —C(O)—, —C(O)O—, —S—, —$S(O)_2$—, —N(R')—, or —C(O)N(R")—, wherein R' and R" may be each independently hydrogen, substituted or unsubstituted $C_{1-20}$ alkyl, substituted or unsubstituted $C_{3-20}$ cycloalkyl, or substituted or unsubstituted $C_{3-20}$ heterocycloalkyl. When $L^7$ is a single bond, the moiety —$R^{37}$ is directly connected to the oxygen atom adjacent to the carbonyl group (i.e., —C(O)O—$R^{37}$).

In formula (9), $R^{37}$ is a substituted or unsubstituted $C_{4-20}$ lactone-containing group or a substituted or unsubstituted $C_{4-20}$ sultone-containing group. The $C_{4-20}$ lactone-containing group and the $C_{4-20}$ sultone-containing group may be monocyclic, polycyclic, or fused polycyclic.

Exemplary monomers of formula (9) may include one or more of the following:

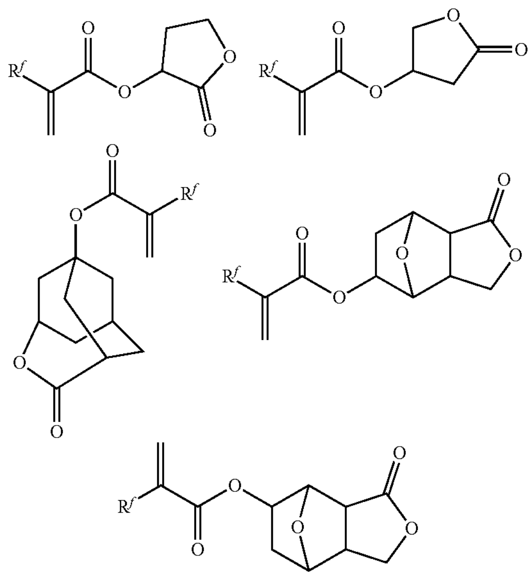

-continued

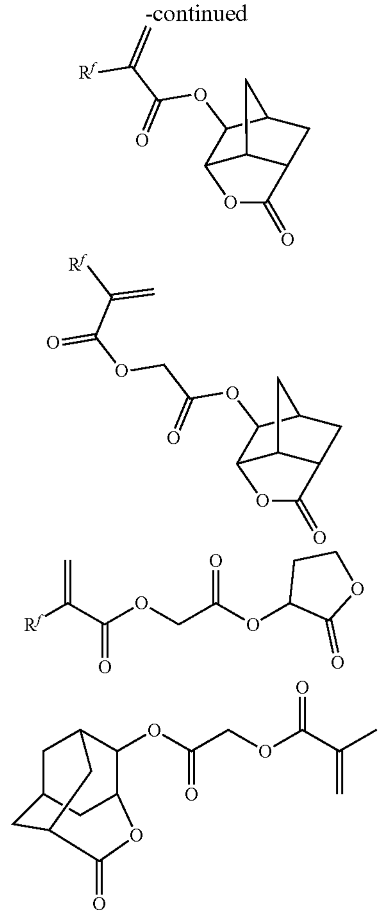

wherein $R^f$ is as defined for formula (9).

The polymer may include a repeating unit that is base-soluble and/or that has a pKa of less than or equal to 12. For example, the repeating unit including a polar group pendant to the backbone of the polymer may be derived from one or more monomers of formulae (10), (11), or (12):

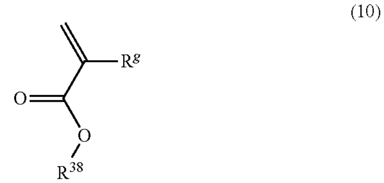

(10)

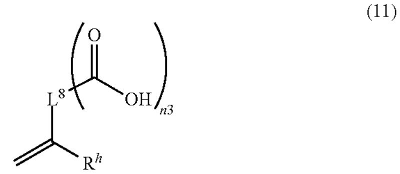

(11)

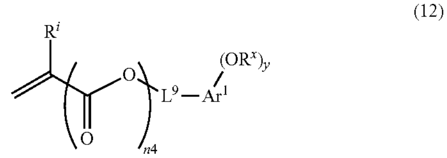

(12)

In formulae (10), (11), or (12), $R^g$ to $R^j$ may each independently be hydrogen, fluorine, cyano, or substituted or unsubstituted $C_{1-10}$ alkyl. Preferably, $R^g$ to $R^j$ may each independently be hydrogen, fluorine, or substituted or unsubstituted $C_{1-5}$ alkyl, typically methyl.

In formula (10), $R^{38}$ may be substituted or unsubstituted $C_{1-100}$ or $C_{1-20}$ alkyl, typically $C_{1-12}$ alkyl; substituted or unsubstituted $C_{3-30}$ or $C_{3-20}$ cycloalkyl; or substituted or unsubstituted poly($C_{1-3}$ alkylene oxide). Preferably, the substituted $C_{1-100}$ or $C_{1-20}$ alkyl, the substituted $C_{3-30}$ or $C_{3-20}$ cycloalkyl, and the substituted poly($C_{1-3}$ alkylene oxide) are substituted with one or more of halogen, a fluoroalkyl group such as a $C_{1-4}$ fluoroalkyl group, typically fluoromethyl, a sulfonamide group —NH—$S(O)_2$—$Y^1$ where $Y^1$ is F or $C_{1-4}$ perfluoroalkyl (e.g., —$NHSO_2CF_3$), or a fluoroalcohol group (e.g., —$C(CF_3)_2OH$).

In formula (11), $L^8$ represents a single bond or a multivalent linking group chosen, for example, from optionally substituted aliphatic, such as $C_{1-6}$ alkylene or $C_{3-20}$ cycloalkylene, and aromatic hydrocarbons, and combinations thereof, optionally with one or more linking moieties chosen from —O—, —C(O)—, —C(O)O—, —S—, —$S(O)_2$—, —$NR^{102}$—, or —C(O)N($R^{102}$)—, wherein $R^{102}$ is chosen from hydrogen and optionally substituted $C_{1-10}$ alkyl. For example, the polymer may further include a repeating unit derived from one or more monomers of formula (10) wherein $L^8$ is a single bond, or a multivalent linking group selected from substituted or unsubstituted $C_{1-20}$ alkylene, substituted or unsubstituted $C_{3-20}$ cycloalkylene, and substituted or unsubstituted $C_{6-24}$ arylene, typically substituted or unsubstituted $C_{1-6}$ alkylene, substituted or unsubstituted $C_{3-10}$ cycloalkylene, or substituted or unsubstituted $C_{6-24}$ arylene.

In formula (11), n3 is an integer from 1 to 5, typically 1. It is to be understood that when n3 is 1, the group $L^8$ is a divalent linking group. It is to be understood that when n3 is 2, the group $L^8$ is a trivalent linking group. Similarly, it is to be understood that when n3 is 3, the group $L^8$ is a tetravalent linking group; when n3 is 4, the group $L^8$ is a pentavalent linking group; and when n3 is 5, the group $L^8$ is a hexavalent linking group. Accordingly, in the context of formula (10), the term “multivalent linking group” refers to any of a divalent, trivalent, tetravalent, pentavalent, and/or hexavalent linking groups. In some aspects, when n is 2 or greater, the carboxylic acid groups (—C(O)OH) may be connected to the same atom of the linking group $L^8$. In other aspects, when n is 2 or greater, the carboxylic acid groups (—C(O)OH) may be connected to different atoms of the linking group $L^8$.

In formula (12), $L^9$ represents a single bond or a divalent linking group. Preferably, $L^9$ may be a single bond, substituted or unsubstituted $C_{6-30}$ arylene, or substituted or unsubstituted $C_{6-30}$ cycloalkylene.

In formula (12), n4 is 0 or 1. It is to be understood that when n4 is 0, the moiety represented by —OC(O)— is a single bond such that $L^9$ is directly connected to the alkenyl (vinylic) carbon atom.

In formula (12), $Ar^1$ is a substituted $C_{5-60}$ aromatic group that optionally includes one or more aromatic ring heteroatoms chosen from N, O, S, or a combination thereof, wherein the aromatic group may be monocyclic, non-fused polycyclic, or fused polycyclic. When the $C_{5-60}$ aromatic group is polycyclic, the ring or ring groups may be fused (such as naphthyl or the like), non-fused, or a combination thereof. When the polycyclic $C_{5-60}$ aromatic group is non-fused, the ring or ring groups may be directly linked (such as biaryls, biphenyl, or the like) or may be bridged by a heteroatom (such as triphenylamino or diphenylene ether). In some aspects, the polycyclic $C_{5-60}$ aromatic group may include a combination of fused rings and directly linked rings (such as binaphthyl or the like).

In formula (12), y may be an integer from 1 to 12, preferably from 1 to 6, and typically from 1 to 3. Each $R^x$ may independently be hydrogen or methyl.

Non-limiting examples of monomers of formulae (10), (11), or (12) include one or more of the following:

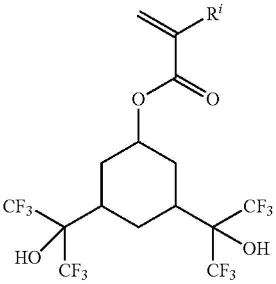
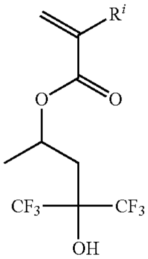

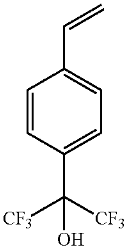
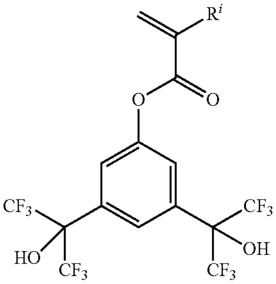
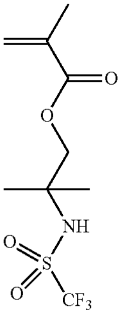

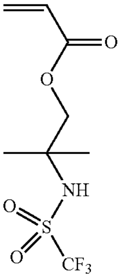
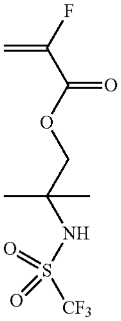
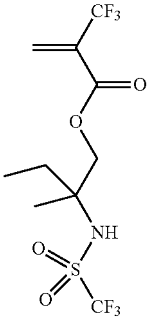
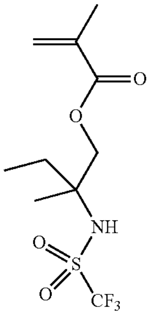

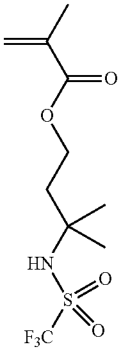
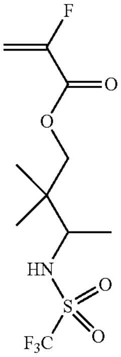
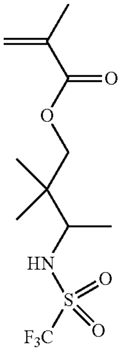
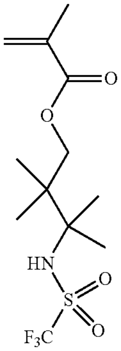

-continued

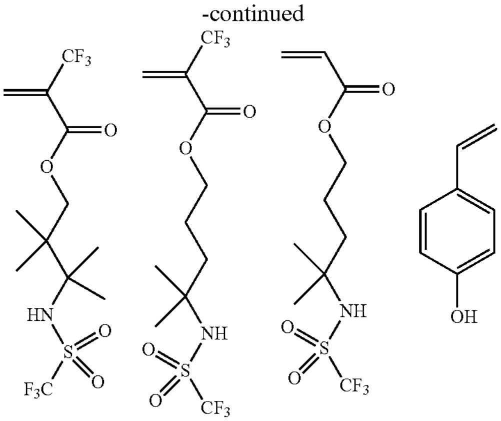
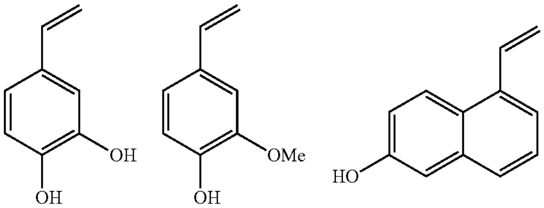
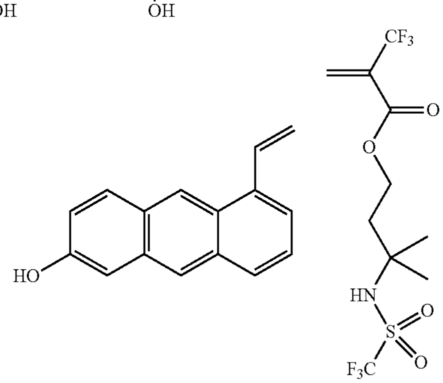
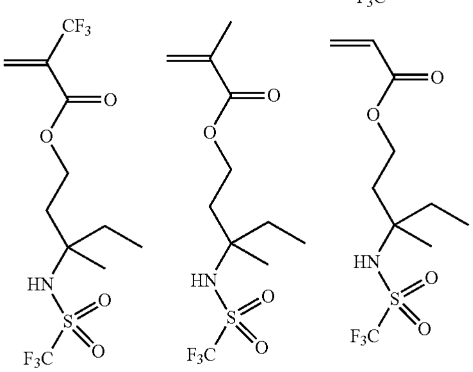
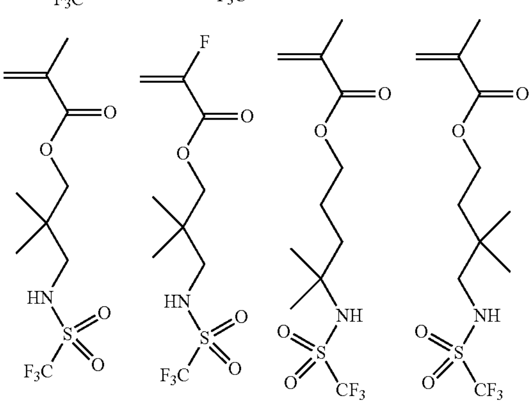

-continued

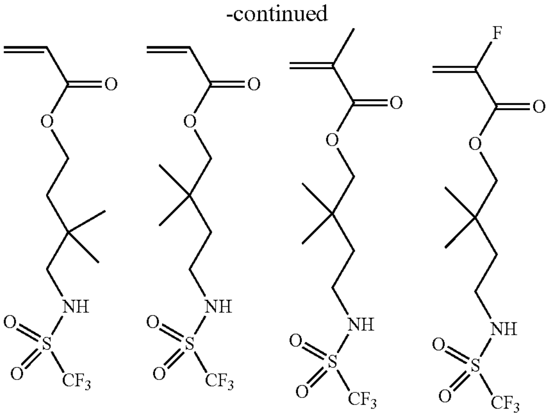
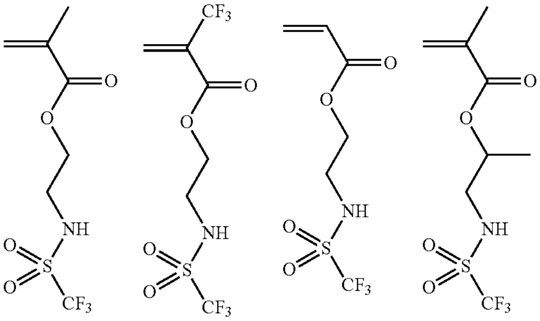
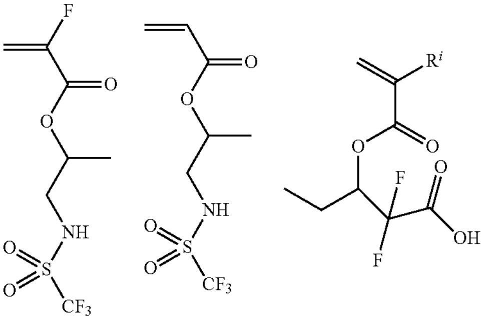
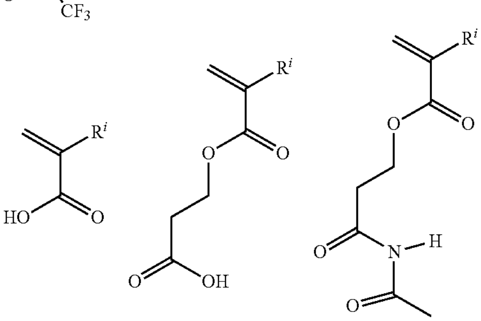

wherein $Y^1$ is as described above, and $R^1$ is as defined in formulae (10)-(12).

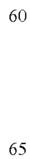

When present, the polymer typically comprises a repeating unit comprising a polar group (pendant to a backbone of the polymer) in an amount from 1 to 60 mol %, typically from 5 to 50 mol %, more typically from 5 to 40 mol %, based on total repeating units in the polymer.

Non-limiting exemplary polymers of the present invention include one or more of the following:

-continued
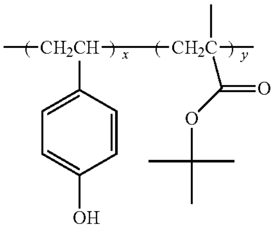
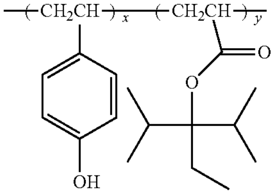
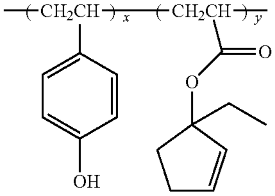
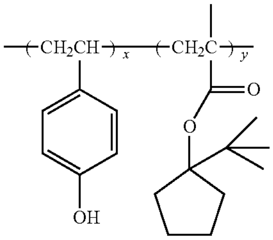
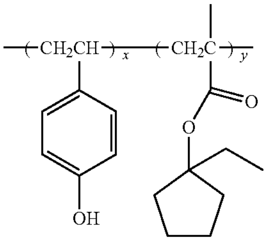
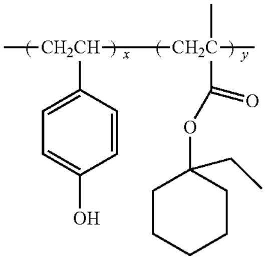
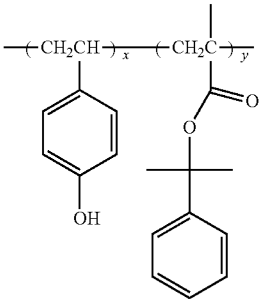
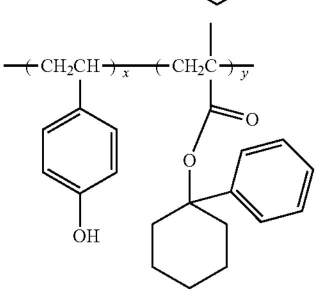
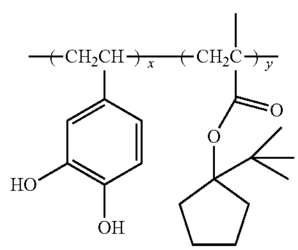
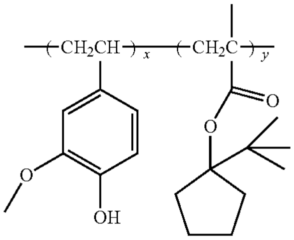
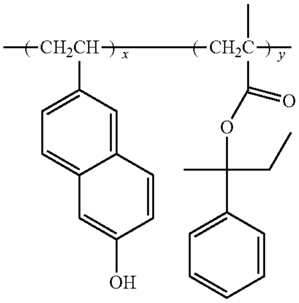
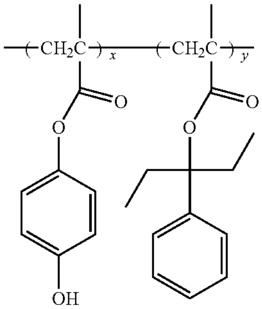
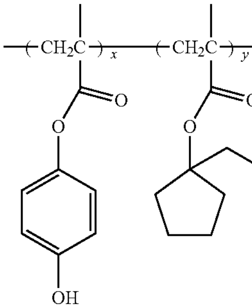
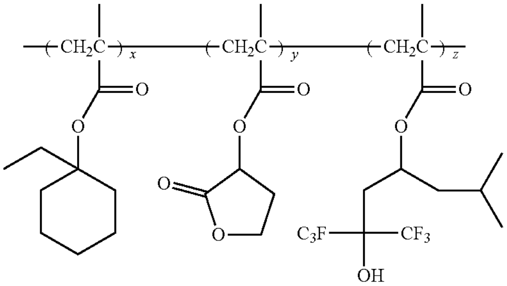
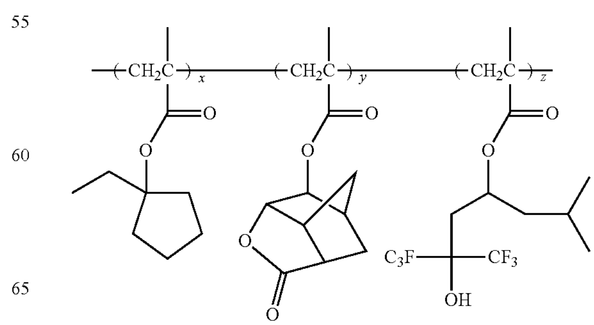

-continued
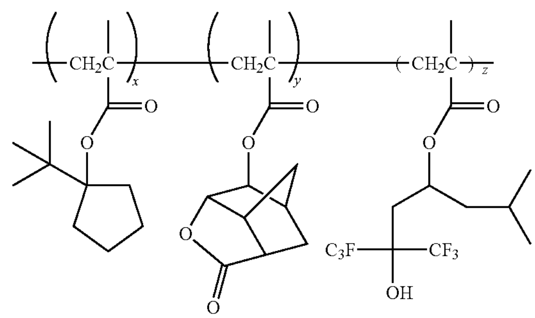
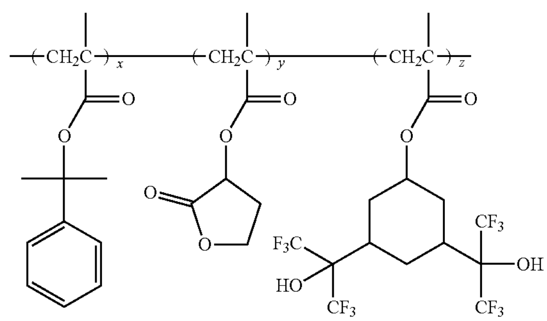
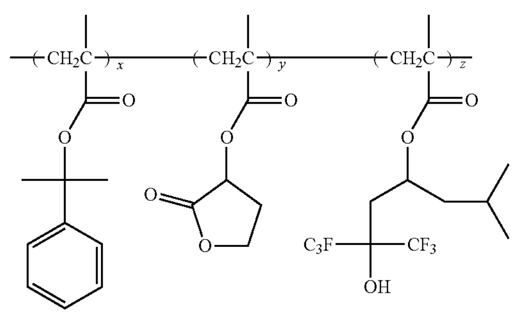
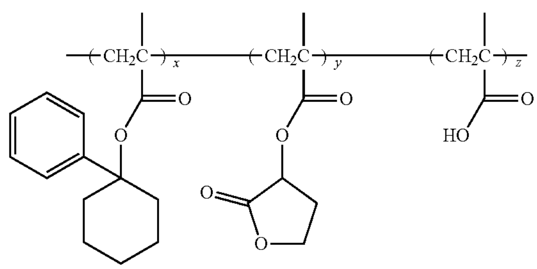
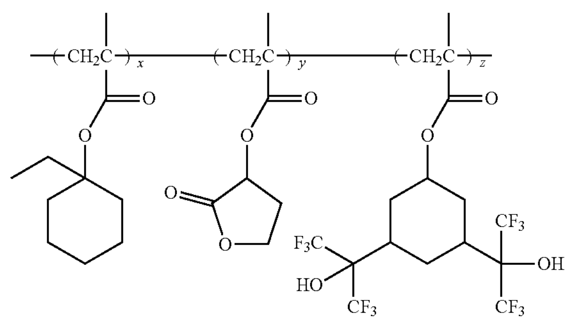
-continued
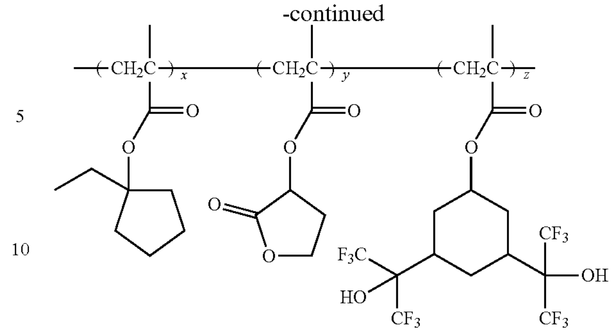
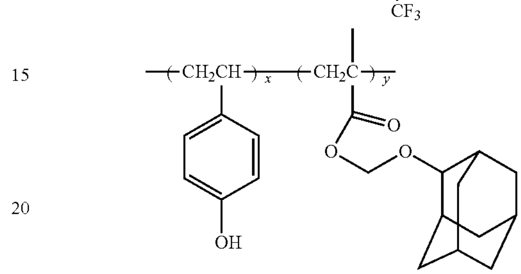
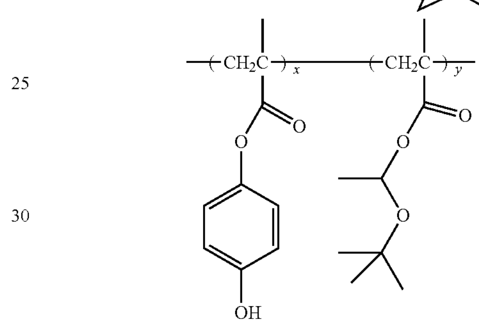
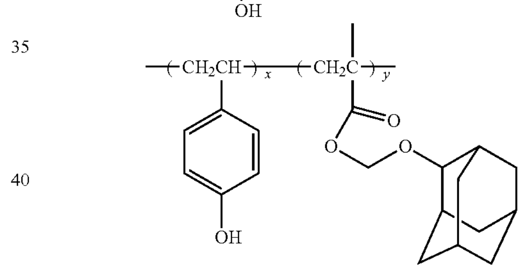
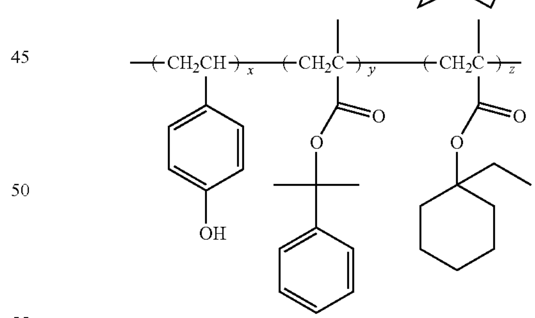
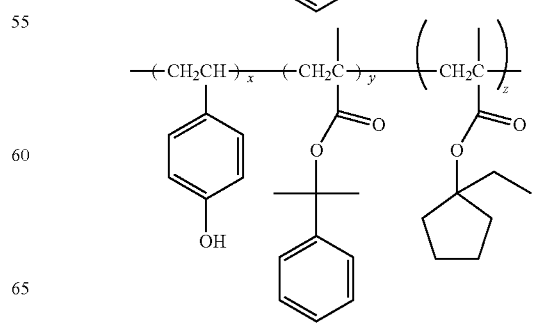

-continued

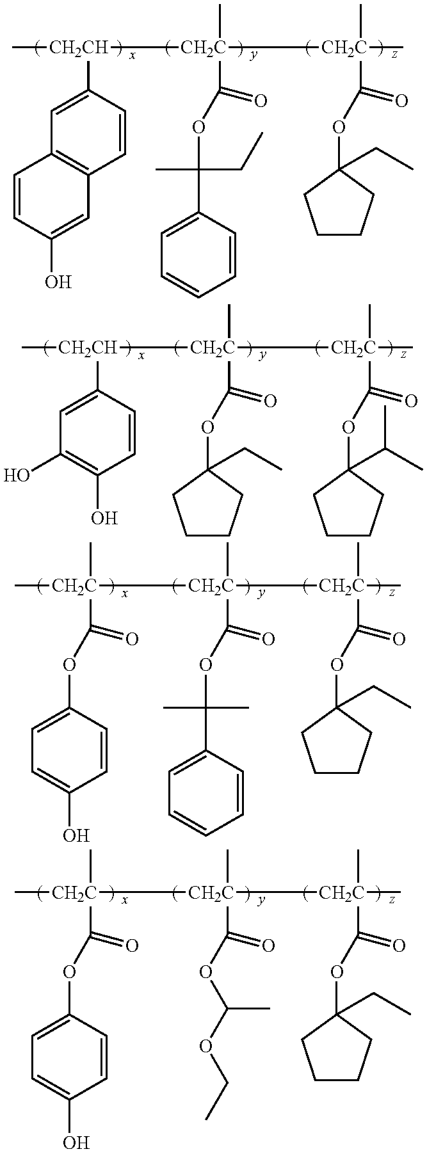

wherein each of x, y and z is a molar fraction of an associated repeating unit, wherein the sum of the molar fractions for each polymer adds up to 1.

The polymer may be prepared using any suitable method(s) in the art. For example, one or more monomers corresponding to the repeating units described herein may be combined, or fed separately, using suitable solvent(s) and initiator, and polymerized in a reactor. For example, the polymer may be obtained by polymerization of the respective monomers under any suitable conditions, such as by heating at an effective temperature, irradiation with actinic radiation at an effective wavelength, or a combination thereof.

The photoresist composition further comprises a photoacid generator (PAG). Suitable PAGs can generate an acid that, during post-exposure bake (PEB), causes cleavage of acid-labile groups present on a polymer of the photoresist composition. The PAG may be in non-polymeric form or in polymeric form, for example, present in a polymerized repeating unit of the polymer as described above, or as part of a different polymer. Suitable non-polymeric PAG compounds may have formula $G^+A^-$, wherein $G^+$ is an organic cation chosen from iodonium cations substituted with two alkyl groups, two aryl groups, or a combination of alkyl and aryl groups; and sulfonium cations substituted with three alkyl groups, three aryl groups, or a combination of alkyl and aryl groups, and $A^-$ is a non-polymerizable organic anion. In some embodiments, PAG may be included as a non-polymerized PAG compound, as a repeating unit of a polymer having a PAG moiety that is derived from a polymerizable PAG monomer, or as a combination thereof.

Particularly suitable non-polymeric organic anions include those, the conjugated acids of which have a pKa of from −15 to 1. Particularly preferred anions are fluorinated alkyl sulfonates and fluorinated sulfonimides.

Useful non-polymeric PAG compounds are known in the art of chemically amplified photoresists and include, for example: onium salts, for example, triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate; di-t-butyphenyliodonium perfluorobutanesulfonate, and di-t-butyphenyliodonium camphorsulfonate. Non-ionic sulfonates and sulfonyl compounds are also known to function as photoacid generators, e.g., nitrobenzyl derivatives, for example, 2-nitrobenzyl-p-toluenesulfonate, 2,6-dinitrobenzyl-p-toluenesulfonate, and 2,4-dinitrobenzyl-p-toluenesulfonate; sulfonic acid esters, for example, 1,2,3-tris(methanesulfonyloxy)benzene, 1,2,3-tris(trifluoromethanesulfonyloxy)benzene, and 1,2,3-tris(p-toluenesulfonyloxy)benzene; diazomethane derivatives, for example, bis(benzenesulfonyl)diazomethane, bis(p-toluenesulfonyl)diazomethane; glyoxime derivatives, for example, bis-O-(p-toluenesulfonyl)-α-dimethylglyoxime, and bis-O-(n-butanesulfonyl)-α-dimethylglyoxime; sulfonic acid ester derivatives of an N-hydroxyimide compound, for example, N-hydroxysuccinimide methanesulfonic acid ester, N-hydroxysuccinimide trifluoromethanesulfonic acid ester; and halogen-containing triazine compounds, for example, 2-(4-methoxyphenyl)-4,6-bis(trichloromethyl)-1,3,5-triazine, and 2-(4-methoxynaphthyl)-4,6-bis(trichloromethyl)-1,3,5-triazine. Suitable non-polymerized photoacid generators are further described in U.S. Pat. No. 8,431,325 to Hashimoto et al. in column 37, lines 11-47 and columns 41-91. Other suitable sulfonate PAGs include sulfonated esters and sulfonyloxy ketones, nitrobenzyl esters, s-triazine derivatives, benzoin tosylate, t-butylphenyl α-(p-toluenesulfonyloxy)acetate, and t-butyl α-(p-toluenesulfonyloxy)acetate; as described in U.S. Pat. Nos. 4,189,323 and 8,431,325.

Typically, when the photoresist composition includes a non-polymeric photoacid generator, it is present in the photoresist composition in an amount of from 1 to 65 wt %, more typically 2 to 20 wt %, based on total solids of the photoresist composition.

In some embodiments, $G^+$ may be a sulfonium cation or an iodonium cation. For example, $G^+$ may be a sulfonium cation as described herein for $M^+$, or $G^+$ may be an iodonium cation as described herein for $M^+$. When the photoresist composition further includes a PAG, the cation $G^+$ may be the same as $M^+$, or the cation $G^+$ may be different from $M^+$.

PAGs that are onium salts typically comprise an organic anion having a sulfonate group or a non-sulfonate-type group, such as sulfonamidate, sulfonimidate, methide, or borate.

Exemplary organic anions having a sulfonate group include the following:

-continued
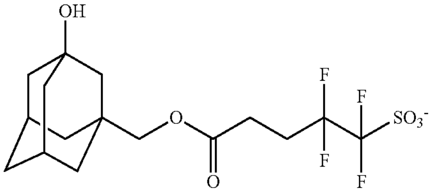
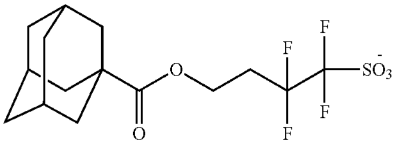
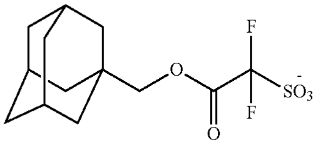
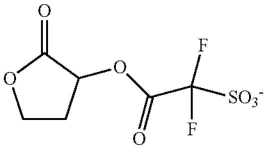
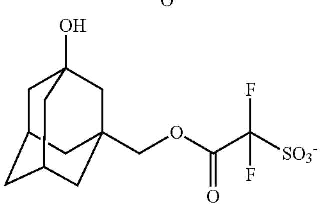
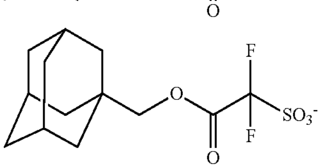
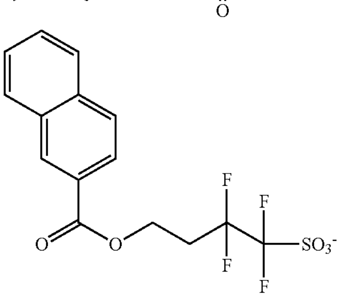
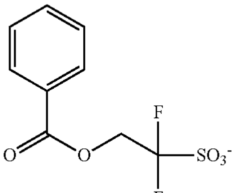
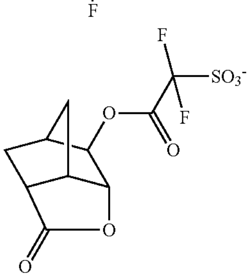
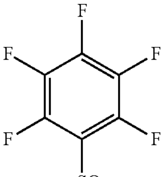
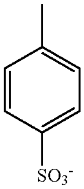
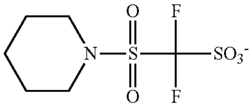
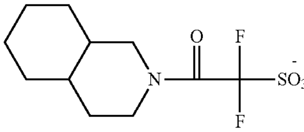
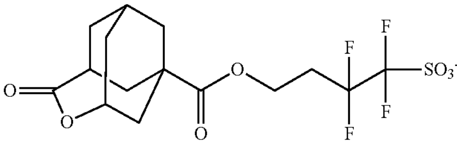
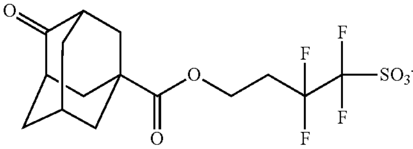
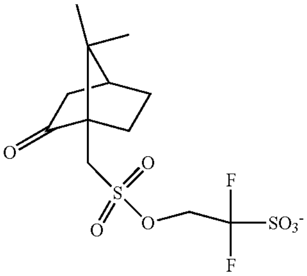
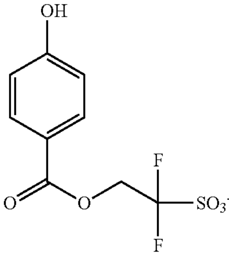
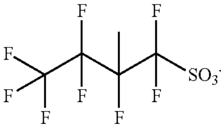
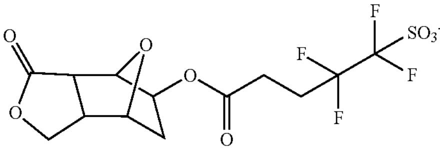
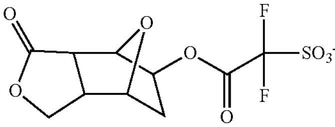
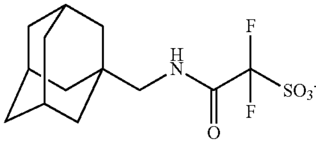
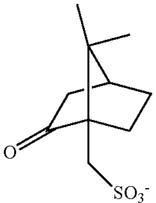
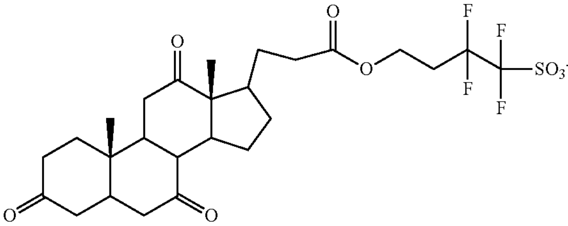

-continued

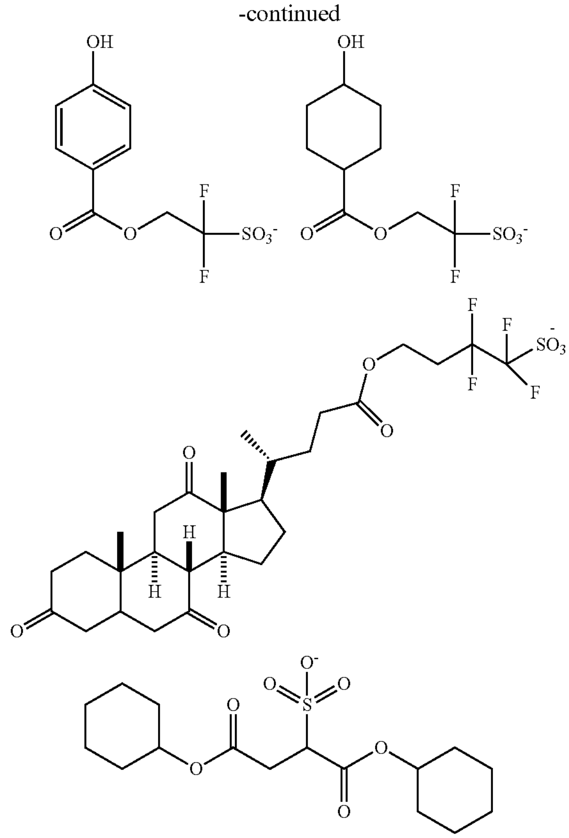

Exemplary non-sulfonated anions include the following:

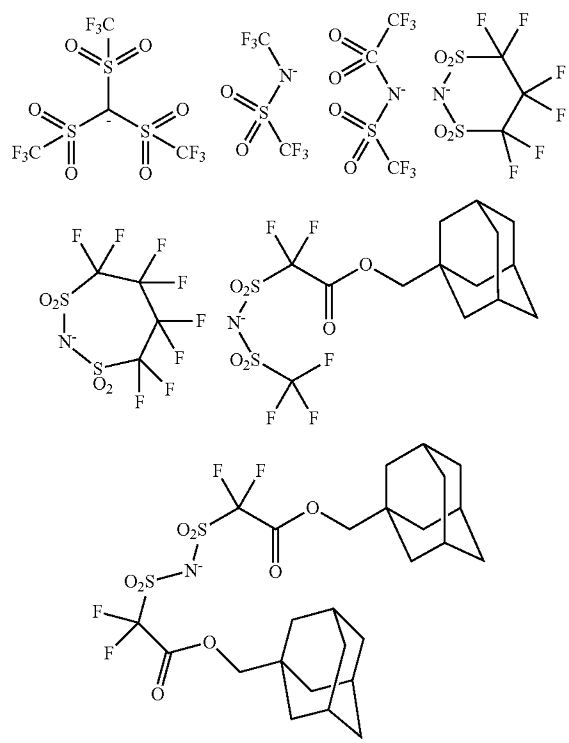

-continued

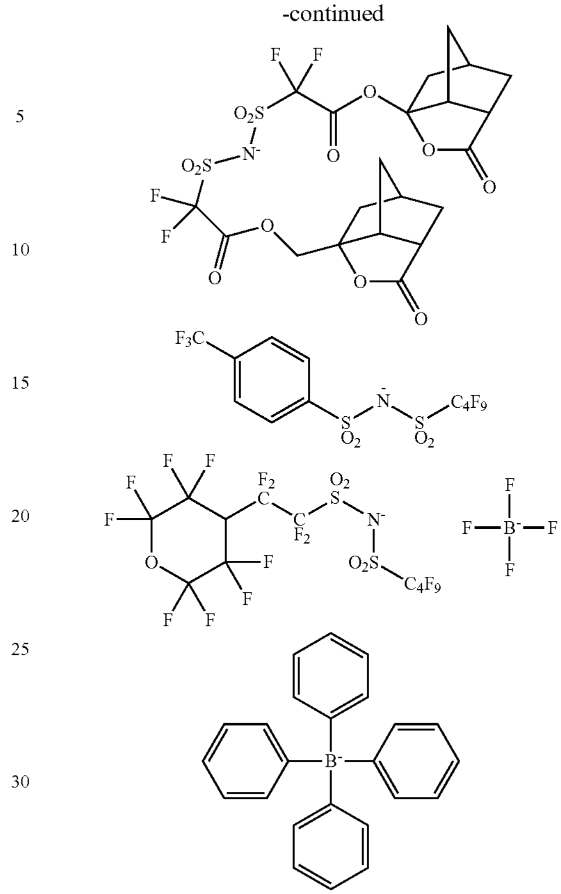

The photoresist composition may optionally comprise a plurality of PAGs. The plurality PAGs may be polymeric, non-polymeric, or may include both polymeric and non-polymeric PAGs. Preferably, each PAG of the plurality of PAGs is non-polymeric.

In one or more aspects, the photoresist composition may include a first photoacid generator that includes a sulfonate group on the anion, and the photoresist composition may include a second photoacid generator that is non-polymeric, wherein the second photoacid generator may include an anion that is free of sulfonate groups.

In some aspect, the polymer optionally may further comprise a repeating unit comprising a PAG-containing moiety. For example, a repeating unit derived from one or more monomers of formula (13):

(13)

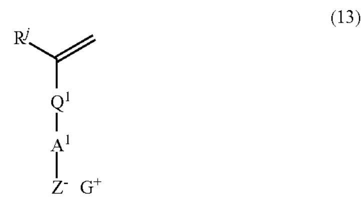

In formula (13), $R^j$ may be hydrogen, fluorine, cyano, or substituted or unsubstituted $C_{1-10}$ alkyl. Preferably, $R^j$ is hydrogen, fluorine, or substituted or unsubstituted $C_{1-5}$ alkyl, typically methyl. $Q^1$ may be a single bond or a divalent linking group. Preferably, $Q^1$ may include 1 to 10 carbon atoms and at least one heteroatom, more preferably —C(O)—O—.

In formula (13), $A^1$ may be one or more of substituted or unsubstituted $C_{1-30}$ alkylene, substituted or unsubstituted $C_{3-30}$ cycloalkylene, substituted or unsubstituted $C_{2-30}$ heterocycloalkylene, substituted or unsubstituted $C_{6-30}$ arylene, or substituted or unsubstituted $C_{3-30}$ heteroarylene. Preferably, $A^1$ may be a divalent $C_{1-30}$ perfluoroalkylene group that is optionally substituted.

In formula (13), $Z^-$ is an anionic moiety, the conjugated acid of which typically has a pKa from −15 to 1. $Z^-$ may be a sulfonate, a carboxylate, an anion of a sulfonamide, an anion of a sulfonimide, or a methide anion. Particularly preferred anion moieties are fluorinated alkyl sulfonates and fluorinated sulfonimides. $G^+$ is an organic cation as defined above. In some embodiments, $G^+$ is an iodonium cation substituted with two alkyl groups, two aryl groups, or a combination of alkyl and aryl groups; or a sulfonium cation substituted with three alkyl groups, three aryl groups, or a combination of alkyl and aryl groups.

Exemplary monomers of formula (13) may include the following:

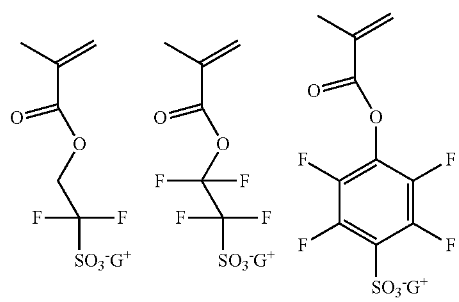

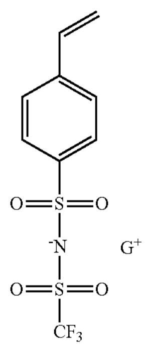

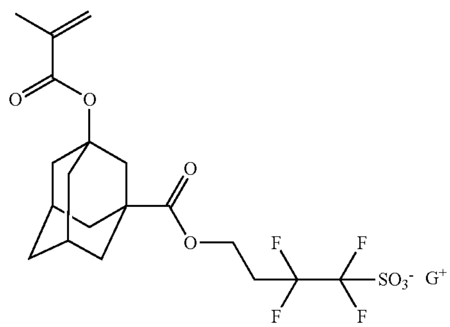

-continued

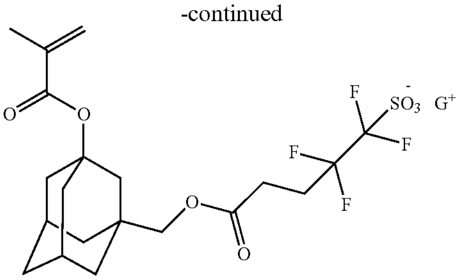

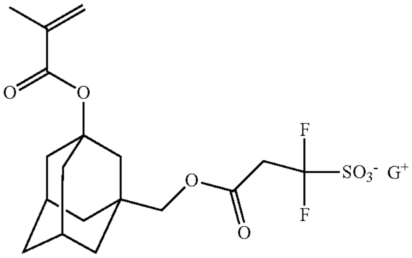

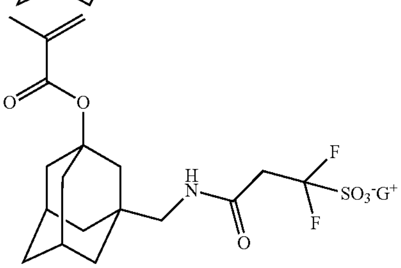

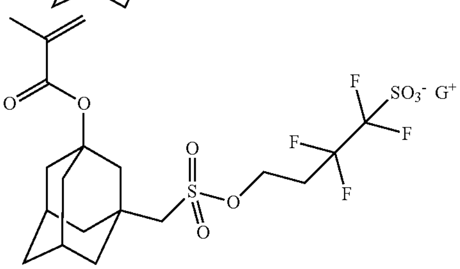

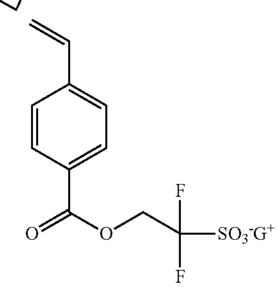

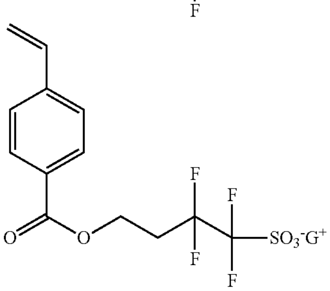

wherein $G^+$ is the organic cation.

When included, the polymer may include a repeating unit comprising a PAG moiety in an amount from 1 to 15 mol %, typically from 1 to 8 mol %, more typically from 2 to 6 mol %, based on total repeating units in the polymer.

The photoresist composition may include a molecular glass compound. Molecular glass compounds are tetrameric calix[4]arenes having free hydroxy groups modified using acetal chemistry to include base-stable but acid-cleavable aromatic protecting groups, as provided in U.S. Pat. No. 8,936,000 B2. The photoresist composition may include the molecular glass compound in an amount of 50 to 99 wt %, preferably 55 to 95 wt %, more preferably 60 to 90 wt %, and still more preferably 65 to 90 wt % based on the total weight of solids. It will be understood that "molecular glass compound" used in this context of a component in a photoresist may mean only the molecular glass compounds, or a combination of the molecular glass compound with another molecular glass compound or polymer useful in a photoresist.

The photoresist composition further includes a solvent for dissolving the components of the composition and facilitating its coating on a substrate. Preferably, the solvent is an organic solvent conventionally used in the manufacture of electronic devices. Suitable solvents include, for example: aliphatic hydrocarbons such as hexane and heptane; aromatic hydrocarbons such as toluene and xylene; halogenated hydrocarbons such as dichloromethane, 1,2-dichloroethane and 1-chlorohexane; alcohols such as methanol, ethanol, 1-propanol, iso-propanol, tert-butanol, 2-methyl-2-butanol, 4-methyl-2-pentanol, and diacetone alcohol (4-hydroxy-4-methyl-2-pentanone); propylene glycol monomethyl ether (PGME); ethers such as diethyl ether, tetrahydrofuran, 1,4-dioxane and anisole; ketones such as acetone, methyl ethyl ketone, methyl iso-butyl ketone, 2-heptanone and cyclohexanone (CHO); esters such as ethyl acetate, n-butyl acetate, propylene glycol monomethyl ether acetate (PGMEA), ethyl lactate (EL), hydroxyisobutyrate methyl ester (HBM) and ethyl acetoacetate; lactones such as gamma-butyrolactone (GBL) and epsilon-caprolactone; lactams such as N-methyl pyrrolidone; nitriles such as acetonitrile and propionitrile; cyclic or non-cyclic carbonate esters such as propylene carbonate, dimethyl carbonate, ethylene carbonate, propylene carbonate, diphenyl carbonate, and propylene carbonate; polar aprotic solvents such as dimethyl sulfoxide and dimethyl formamide; water; and combinations thereof. Of these, preferred solvents are PGME, PGMEA, EL, GBL, HBM, CHO, and combinations thereof.

The total solvent content (i.e., cumulative solvent content for all solvents) in the photoresist compositions is typically from 40 to 99 wt %, for example, from 70 to 99 wt %, or from 85 to 99 wt %, based on total solids of the photoresist composition. The desired solvent content will depend, for example, on the desired thickness of the coated photoresist layer and coating conditions.

The polymer typically may be present in the photoresist composition in an amount from 10 to 99.9 wt %, typically from 25 to 99 wt %, and more typically from 50 to 95 wt %, based on total solids of the photoresist composition. It will be understood that "total solids" includes the photoactive compound, polymers, PAGs, and other non-solvent components.

In some aspects, the photoresist composition may further include a material that comprises one or more base-labile groups (a "base-labile material"). As referred to herein, base-labile groups are functional groups that can undergo cleavage reaction to provide polar groups such as hydroxyl, carboxylic acid, sulfonic acid, and the like, in the presence of an aqueous alkaline developer after exposure and post-exposure baking steps. The base-labile group will not react significantly (e.g., will not undergo a bond-breaking reaction) prior to a development step of the photoresist composition that comprises the base-labile group. Thus, for instance, a base-labile group will be substantially inert during pre-exposure soft-bake, exposure, and post-exposure bake steps. By "substantially inert" it is meant that ≤5%, typically ≤1%, of the base-labile groups (or moieties) will decompose, cleave, or react during the pre-exposure soft-bake, exposure, and post-exposure bake steps. The base-labile group is reactive under typical photoresist development conditions using, for example, an aqueous alkaline photoresist developer such as a 0.26 normal (N) aqueous solution of tetramethylammonium hydroxide (TMAH). For example, a 0.26 N aqueous solution of TMAH may be used for single puddle development or dynamic development, e.g., where the 0.26 N TMAH developer is dispensed onto an imaged photoresist layer for a suitable time such as 10 to 120 seconds (s). An exemplary base-labile group is an ester group, typically a fluorinated ester group. Preferably, the base-labile material is substantially not miscible with and has a lower surface energy than the polymer and other solid components of the photoresist composition. When coated on a substrate, the base-labile material can thereby segregate from other solid components of the photoresist composition to a top surface of the formed photoresist layer.

In some aspects, the base-labile material may be a polymeric material, also referred to herein as a base-labile polymer, which may include one or more repeating units comprising one or more base-labile groups. For example, the base-labile polymer may comprise a repeating unit comprising 2 or more base-labile groups that are the same or different. A preferred base-labile polymer includes at least one repeating unit comprising 2 or more base-labile groups, for example a repeating unit comprising 2 or 3 base-labile groups.

The base-labile polymer may be a polymer comprising a repeating unit derived from one or more monomers of formula (14a):

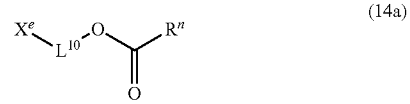

(14a)

wherein $X^c$ is a polymerizable group selected from substituted or unsubstituted $C_{2-20}$ alkenyl or substituted or unsubstituted (meth)acryloyl, $L^{10}$ is a divalent linking group that may include, for example, one or more of substituted or unsubstituted $C_{1-20}$ alkylene, substituted or unsubstituted $C_{3-20}$ cycloalkylene, —C(O)—, or —C(O)O—; and $R^n$ is substituted or unsubstituted $C_{1-20}$ fluoroalkyl, provided that the carbon atom bonded to the carbonyl (C═O) in formula (14a) is substituted with at least one fluorine atom.

Exemplary monomers of formula (14a) may include the following:

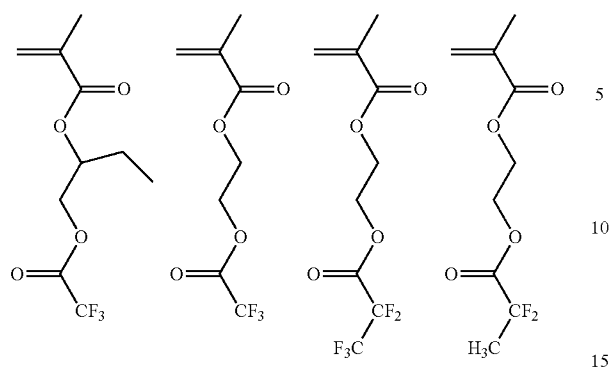

The base-labile polymer may include a repeating unit including two or more base-labile groups. For example, the base-labile polymer can include a repeating unit derived from one or more monomers of formula (14b):

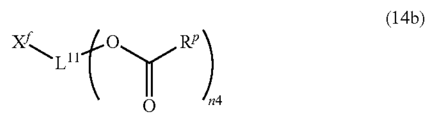

(14b)

wherein $X^f$ and $R^p$ are as defined in Formula (14a) for $X^e$ and $R''$, respectively; $L^{11}$ is a polyvalent linking group including one or more of substituted or unsubstituted $C_{1-20}$ alkylene, substituted or unsubstituted $C_{3-20}$ cycloalkylene, —C(O)—, or —C(O)O—; and n4 is an integer of 2 or greater, for example 2 or 3.

Exemplary monomers of Formula (14b) may include the following:

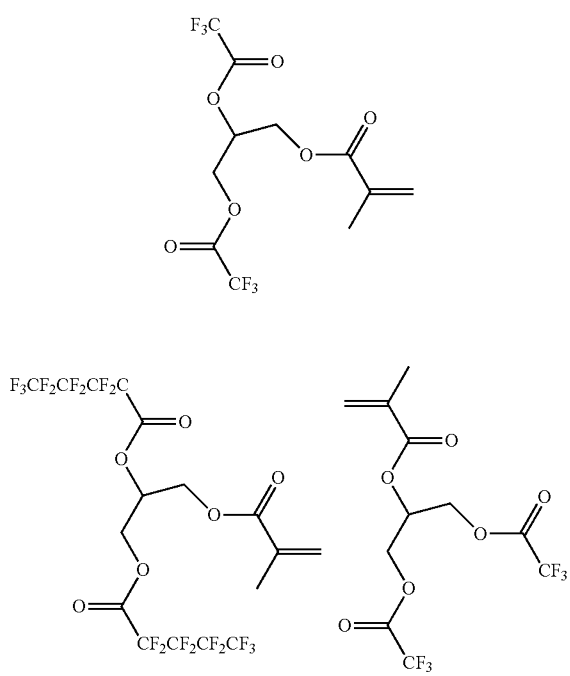

-continued

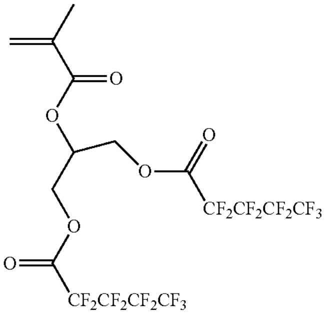

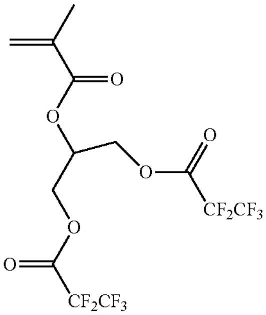

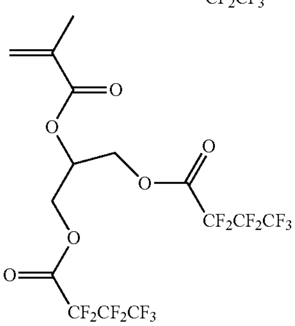

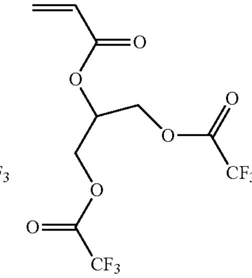

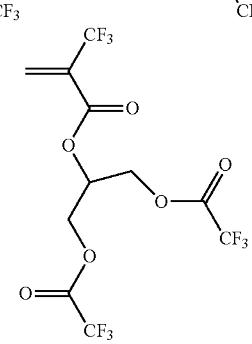

The base-labile polymer may include a repeating unit including one or more base-labile groups. For example, the base-labile polymer can include a repeating unit derived from one or more monomers of formula (14c):

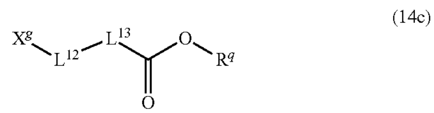

(14c)

wherein $X^g$ and $R^q$ are as defined in formula (14a) for $X^e$ and $R''$, respectively; $L^{12}$ is a divalent linking group; and $L^{13}$ is substituted or unsubstituted $C_{1-20}$ fluoroalkylene wherein the carbon atom bonded to the carbonyl (C═O) in formula (14c) is substituted with at least one fluorine atom.

Exemplary monomers of formula (14c) may include the following:

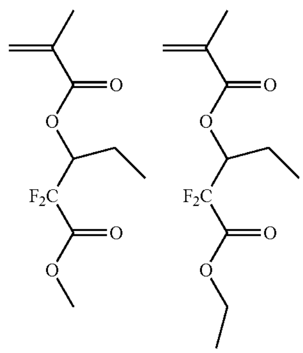

In a further preferred aspect of the invention, a base-labile polymer may comprise one or more base-labile groups and one or more acid-labile groups, such as one or more acid-labile ester moieties (e.g., t-butyl ester) or acid-labile acetal groups. For example, the base-labile polymer may comprise a repeating unit including a base-labile group and an acid-labile group, i.e., wherein both a base-labile group and an acid-labile group are present on the same repeating unit. In another example, the base-labile polymer may comprise a first repeating unit comprising a base-labile group and a second repeating unit comprising an acid-labile group. Preferred photoresists of the invention can exhibit reduced defects associated with a resist relief image formed from the photoresist composition.

The base-labile polymer may be prepared using any suitable methods in the art, including those described herein for the first and second polymers. For example, the base-labile polymer may be obtained by polymerization of the respective monomers under any suitable conditions, such as by heating at an effective temperature, irradiation with actinic radiation at an effective wavelength, or a combination thereof. Additionally, or alternatively, one or more base-labile groups may be grafted onto the backbone of a polymer using suitable methods.

In some aspects, the base-labile material is a single molecule comprising one more base-labile ester groups, preferably one or more fluorinated ester groups. The base-labile materials that are single molecules typically have a $M_W$ in the range from 50 to 1,500 Da. Exemplary base-labile materials include the following:

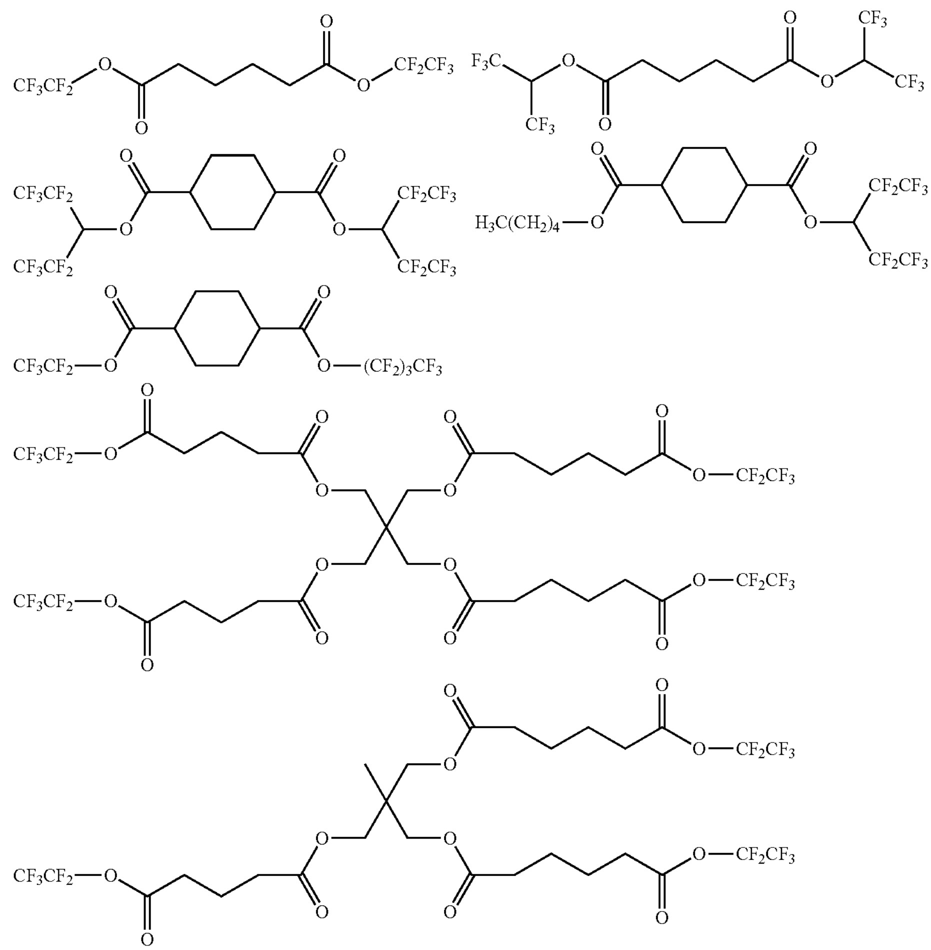

When present, the base-labile material is typically present in the photoresist compositions in an amount of from 0.01 to 10 wt %, or 1 to 5 wt %, based on total solids of the photoresist composition.

Additionally, or alternatively, to the base-labile polymer, the photoresist compositions may further include one or more polymers in addition to and different from the photoresist polymer described above. For example, the photoresist compositions may include an additional polymer as described above but different in composition, or a polymer that is similar to those described above but does not include each of the requisite repeating units. Additionally, or alternatively, the one or more additional polymers may include those well known in the photoresist art, for example, those chosen from polyacrylates, polyvinylethers, polyesters, polynorbornenes, polyacetals, polyethylene glycols, polyamides, polyacrylamides, polyphenols, novolacs, styrenic polymers, polyvinyl alcohols, or combinations thereof.

The photoresist composition may further include one or more additional, optional additives. For example, optional additives may include actinic and contrast dyes, anti-striation agents, plasticizers, speed enhancers, sensitizers, photo-decomposable quenchers (PDQ) (and, also known as photo-decomposable bases), basic quenchers, thermal acid generators, surfactants, and the like, or combinations thereof. If present, the optional additives are typically present in the photoresist compositions in an amount of from 0.01 to 10 wt %, based on total solids of the photoresist composition.

PDQs generate a weak acid upon irradiation. The acid generated from a photo-decomposable quencher is not strong enough to react rapidly with acid-labile groups that are present in the resist matrix. Exemplary photo-decomposable quenchers include, for example, photo-decomposable cations, and preferably those also useful for preparing strong acid generator compounds, paired with an anion of a weak acid (pKa>1) such as, for example, an anion of a $C_{1-20}$ carboxylic acid or $C_{1-20}$ sulfonic acid. Exemplary carboxylic acids include formic acid, acetic acid, propionic acid, tartaric acid, succinic acid, cyclohexanecarboxylic acid, benzoic acid, salicylic acid, and the like. Exemplary sulfonic acids include p-toluene sulfonic acid, camphor sulfonic acid and the like. In a preferred embodiment, the photo-decomposable quencher is a photo-decomposable organic zwitterion compound such as diphenyliodonium-2-carboxylate.

The photo-decomposable quencher may be in non-polymeric or polymer-bound form. When in polymeric form, the photo-decomposable quencher is present in polymerized units on the first polymer or second polymer. The polymerized units containing the photo-decomposable quencher are typically present in an amount from 0.1 to 30 mole %, preferably from 1 to 10 mole % and more preferably from 1 to 2 mole %, based on total repeating units of the polymer.

Exemplary basic quenchers include, for example: linear aliphatic amines such as tributylamine, trioctylamine, triisopropanolamine, tetrakis(2-hydroxypropyl)ethylenediamine: n-tert-butyldiethanolamine, tris(2-acetoxy-ethyl) amine, 2,2',2",2'"-(ethane-1,2-diylbis(azanetriyl))tetraethanol, 2-(dibutylamino)ethanol, and 2,2',2"-nitrilotriethanol; cyclic aliphatic amines such as 1-(tert-butoxycarbonyl)-4-hydroxypiperidine, tert-butyl 1-pyrrolidinecarboxylate, tert-butyl 2-ethyl-1H-imidazole-1-carboxylate, di-tert-butyl piperazine-1,4-dicarboxylate, and N-(2-acetoxy-ethyl) morpholine; aromatic amines such as pyridine, di-tert-butyl pyridine, and pyridinium; linear and cyclic amides and derivatives thereof such as N,N-bis(2-hydroxyethyl)pivalamide, N,N-diethylacetamide, $N^1,N^1,N^3,N^3$-tetrabutylmalonamide, 1-methylazepan-2-one, 1-allylazepan-2-one, and tert-butyl 1,3-dihydroxy-2-(hydroxymethyl)propan-2-ylcarbamate; ammonium salts such as quaternary ammonium salts of sulfonates, sulfamates, carboxylates, and phosphonates; imines such as primary and secondary aldimines and ketimines; diazines such as optionally substituted pyrazine, piperazine, and phenazine; diazoles such as optionally substituted pyrazole, thiadiazole, and imidazole; and optionally substituted pyrrolidones such as 2-pyrrolidone and cyclohexyl pyrrolidine.

The basic quenchers may be in non-polymeric or polymer-bound form. When in polymeric form, the quencher may be present in repeating units of the polymer. The repeating units containing the quencher are typically present in an amount of from 0.1 to 30 mole %, preferably from 1 to 10 mole % and more preferably from 1 to 2 mole %, based on total repeating units of the polymer.

Exemplary surfactants include fluorinated and non-fluorinated surfactants and can be ionic or non-ionic, with non-ionic surfactants being preferable. Exemplary fluorinated non-ionic surfactants include perfluoro $C_4$ surfactants such as FC-4430 and FC-4432 surfactants, available from 3M Corporation; and fluorodiols such as POLYFOX PF-636, PF-6320, PF-656, and PF-6520 fluorosurfactants from Omnova. In an aspect, the photoresist composition further includes a surfactant polymer including a fluorine-containing repeating unit.

Patterning methods using the photoresist compositions of the invention will now be described. Suitable substrates on which the photoresist compositions can be coated include electronic device substrates. A wide variety of electronic device substrates may be used in the present invention, such as: semiconductor wafers; polycrystalline silicon substrates; packaging substrates such as multichip modules; flat panel display substrates; substrates for light emitting diodes (LEDs) including organic light emitting diodes (OLEDs); and the like, with semiconductor wafers being typical. Such substrates are typically composed of one or more of silicon, polysilicon, silicon oxide, silicon nitride, silicon oxynitride, silicon germanium, gallium arsenide, aluminum, sapphire, tungsten, titanium, titanium-tungsten, nickel, copper, and gold. Suitable substrates may be in the form of wafers such as those used in the manufacture of integrated circuits, optical sensors, flat panel displays, integrated optical circuits, and LEDs. Such substrates may be any suitable size. Typical wafer substrate diameters are 200 to 300 millimeters (mm), although wafers having smaller and larger diameters may be suitably employed according to the present invention. The substrates may include one or more layers or structures which may optionally include active or operable portions of devices being formed.

Typically, one or more lithographic layers such as a hardmask layer, for example, a spin-on-carbon (SOC), amorphous carbon, or metal hardmask layer, a CVD layer such as a silicon nitride (SiN), a silicon oxide (SiO), or silicon oxynitride (SiON) layer, an organic or inorganic underlayer, or combinations thereof, are provided on an upper surface of the substrate prior to coating a photoresist composition of the present invention. Such layers, together with an overcoated photoresist layer, form a lithographic material stack.

Optionally, a layer of an adhesion promoter may be applied to the substrate surface prior to coating the photoresist compositions. If an adhesion promoter is desired, any suitable adhesion promoter for polymer films may be used, such as silanes, typically organosilanes such as trimethoxyvinylsilane, triethoxyvinylsilane, hexamethyldisilazane, or an aminosilane coupler such as gamma-aminopropyltriethoxysilane. Particularly suitable adhesion promoters include those sold under the AP 3000, AP 8000, and AP 9000S designations, available from DuPont Electronics & Imaging (Marlborough, Massachusetts).

The photoresist composition may be coated on the substrate by any suitable method, including spin coating, spray coating, dip coating, doctor blading, or the like. For example, applying the layer of photoresist may be accomplished by spin coating the photoresist in solvent using a coating track, in which the photoresist is dispensed on a spinning wafer. During dispensing, the wafer is typically spun at a speed of up to 4,000 rotations per minute (rpm), for example, from 200 to 3,000 rpm for a period from 15 to 120 seconds to obtain a layer of the photoresist composition on the substrate. It will be appreciated by those skilled in the art that the thickness of the coated layer may be adjusted by changing the spin speed and/or the total solids of the composition. A photoresist layer formed from the compositions of the invention typically has a dried layer thickness from 10 to 500 nanometers (n), preferably from 15 to 200 nm, and more preferably from 20 to 120 nm.

The photoresist composition is typically next soft-baked to minimize the solvent content in the layer, thereby forming a tack-free coating and improving adhesion of the layer to the substrate. The soft bake is performed, for example, on a hotplate or in an oven, with a hotplate being typical. The soft bake temperature and time will depend, for example, on the photoresist composition and thickness. The soft bake temperature is typically from 80 to 170° C., and more typically from 90 to 150° C. The soft bake time is typically from 10 seconds to 20 minutes, more typically from 1 minute to 10 minutes, and still more typically from 1 minute to 2 minutes. The heating time can be readily determined by one of ordinary skill in the art based on the ingredients of the composition.

The photoresist layer is next pattern-wise exposed to activating radiation to create a difference in solubility between exposed and unexposed regions. Reference herein to exposing a photoresist composition to radiation that is activating for the composition indicates that the radiation can form a latent image in the photoresist composition. The exposure is typically conducted through a patterned photomask that has optically transparent and optically opaque regions corresponding to regions of the resist layer to be exposed and unexposed, respectively. Such exposure may, alternatively, be conducted without a photomask in a direct writing method, typically used for e-beam lithography. The activating radiation typically has a wavelength of sub-400 nm, sub-300 nm or sub-200 nm, with 248 nm (KrF), 193 nm (ArF), 13.5 nm (EUV) wavelengths or e-beam lithography being preferred. Preferably, the activating radiation is 193 nm radiation or EUV radiation. The methods find use in immersion or dry (non-immersion) lithography techniques. The exposure energy is typically from 1 to 200 millijoules per square centimeter ($mJ/cm^2$), preferably from 10 to 100 $mJ/cm^2$ and more preferably from 20 to 50 $mJ/cm^2$, dependent upon the exposure tool and components of the photoresist composition.

Following exposure of the photoresist layer, a post-exposure bake (PEB) of the exposed photoresist layer is performed. The PEB can be conducted, for example, on a hotplate or in an oven, with a hotplate being typical. Conditions for the PEB will depend, for example, on the photoresist composition and layer thickness. The PEB is typically conducted at a temperature from 70 to 150° C., preferably from 75 to 120° C., and a time from 30 to 120 seconds. A latent image defined by the polarity-switched (exposed regions) and unswitched regions (unexposed regions) is formed in the photoresist.

The exposed photoresist layer is then developed with a suitable developer to selectively remove those regions of the layer that are soluble in the developer while the remaining insoluble regions form the resulting photoresist pattern relief image. In the case of a positive-tone development (PTD) process, the exposed regions of the photoresist layer are removed during development and unexposed regions remain. Conversely, in a negative-tone development (NTD) process, the exposed regions of the photoresist layer remain, and unexposed regions are removed during development. Application of the developer may be accomplished by any suitable method such as described above with respect to application of the photoresist composition, with spin coating being typical. The development time is for a period effective to remove the soluble regions of the photoresist, with a time of from 5 to 60 seconds being typical. Development is typically conducted at room temperature.

Suitable developers for a PTD process include aqueous base developers, for example, quaternary ammonium hydroxide solutions such as tetramethylammonium hydroxide (TMAH), preferably 0.26 normal (N) TMAH, tetraethylammonium hydroxide, tetrabutylammonium hydroxide, sodium hydroxide, potassium hydroxide, sodium carbonate, potassium carbonate, and the like. Suitable developers for an NTD process are organic solvent-based, meaning the cumulative content of organic solvents in the developer is 50 wt % or more, typically 95 wt % or more, 98 wt % or more, or 100 wt %, based on total weight of the developer. Suitable organic solvents for the NTD developer include, for example, those chosen from ketones, esters, ethers, hydrocarbons, and mixtures thereof. The NTD developer is typically 2-heptanone or n-butyl acetate.

A coated substrate may be formed from the photoresist compositions of the invention. Such a coated substrate includes: (a) a substrate having one or more layers to be patterned on a surface thereof; and (b) a layer of the photoresist composition over the one or more layers to be patterned.

The photoresist pattern may be used, for example, as an etch mask, thereby allowing the pattern to be transferred to one or more sequentially underlying layers by known etching techniques, typically by dry-etching such as reactive ion etching. The photoresist pattern may, for example, be used for pattern transfer to an underlying hardmask layer which, in turn, is used as an etch mask for pattern transfer to one or more layers below the hardmask layer. If the photoresist pattern is not consumed during pattern transfer, it may be removed from the substrate by known techniques, for example, oxygen plasma ashing. The photoresist compositions may, when used in one or more such patterning processes, be used to fabricate semiconductor devices such as memory devices, processor chips (CPUs), graphics chips, optoelectronic chips, LEDs, OLEDs, as well as other electronic devices.

The invention is further illustrated by the following examples.

EXAMPLES

Synthesis Examples. The synthetic reactions were performed under normal atmospheric conditions. All chemicals were used as received from commercial suppliers and used without further purification.

Synthesis of Triphenylsulfonium α-Cyanocinnamate (PAC)

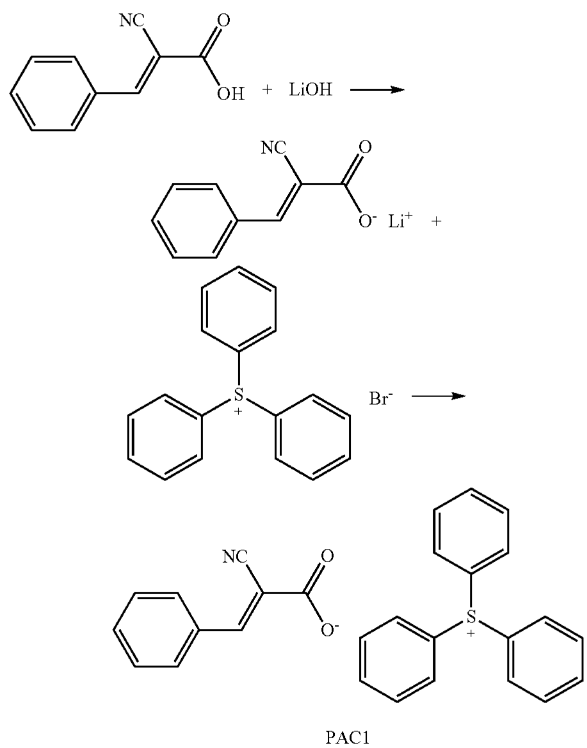

PAC1

5 grams (g) of α-cyanocinnamic acid (28.87 millimoles (mmol)) and tetrahydrofuran (75 mL, THF) were combined to prepare a solution, 1 g of LiOH in 15 milliliters (mL) of deionized (DI) water was added to the solution, and the resulting mixture was stirred at room temperature (ca. 25° C.) for 1 hour. The THF was then removed under a reduced pressure to produce a lithium α-cyanocinnamate salt. To the lithium α-cyanocinnamate salt was added 50 mL of DI water, 75 mL of dichloromethane (DCM), and 9.9 g of triphenylsulfonium bromide (28.87 mmol), and the mixture was stirred at room temperature (ca. 25° C.) for 4 hours. The organic phase was then washed with DI water (5×50 mL). The organic phase was separated from the aqueous phase, and the solvent was removed under a reduced pressure to produce the crude photoactive compound PAC1. The crude product was dissolved in 20 mL of acetone and this solution was poured into 150 mL of heptane to produce PAC1 as a colorless precipitate, which was isolated by filtration and dried to provide a colorless solid. The yield of PAC1 was 3.4 g (35%). Proton Nuclear Magnetic Resonance Spectroscopy ($^1$H-NMR) (in acetone-$d_6$), chemical shift (6, parts per million (ppm)): 8.10 (m, 7H), 7.80 (m, 11H, ArH), 7.40 (m, 3H). Ultraperformance Liquid Chromatography (UPLC) purity was 99.21% as detected by ultraviolet (UV) light absorbance at 210 nm.

Synthesis of bis(4-(tert-butyl)phenyl)iodonium α-cyanocinnamate (PAC2)

10.0 g of α-cyanocinnamic acid (57.74 mmol) and 150 mL of THF were combined to prepare a solution, 2 g of LiOH in 25 mL of DI water was added to the solution, and the resulting mixture was stirred at room temperature (ca. 25° C.) for 1 hour. The THF was then removed under a reduced pressure to produce a lithium α-cyanocinnamate salt. To the lithium α-cyanocinnamate salt was added 100 mL of DI water, 150 mL of DCM, and 24.8 g of bis(4-(tert-butyl)phenyl)iodonium acetate (54.82 mmol), and the mixture was stirred at room temperature (ca. 25° C.) for 4 hours. The organic phase was then washed with DI water (5×100 mL). The organic phase was separated from the aqueous phase, and the solvent was removed under a reduced pressure to produce the crude photoactive compound PAC2. The crude product was dissolved in 40 mL of acetone and this solution was poured into 300 mL of heptane to produce PAC2 as a colorless precipitate, which was isolated by filtration and dried to provide a colorless solid. The yield of PAC2 was 21.7 g (66.5%). $^1$H NMR (in acetone-d6), δ (ppm): 7.89 (m, 4H, ArH), 7.78 (m, 3H, ArH), 7.38 (m, 7H), 1.21 (s, 18H, 6($CH_3$)). UPLC purity was 99.30% as detected by UV light absorbance at 210 nm.

Synthesis of bis(4-(tert-butyl)phenyl)iodonium 4-trifluoromethylcinnamate (PAC3)

5.0 g of 4-trifluoromethylcinnamic acid (23.13 mmol) and 150 mL of THF were combined to prepare a solution, 0.8 g of LiOH in 25 mL of DI water was added to the solution, and the resulting mixture was stirred at room temperature (ca. 25° C.) for 1 hour. The THF was then removed under a reduced pressure to produce a lithium 4-trifluoromethylcinnamate salt. To the lithium 4-trifluoromethylcinnamate salt was added 100 mL of DI water, 150 mL of DCM, and 10.4 g of bis(4-(tert-butyl)phenyl)iodonium acetate (23.0 mmol), and the mixture was stirred at room temperature (ca. 25° C.) for 4 hours. The organic phase was then washed with DI water (5×50 mL). The organic phase was separated from the aqueous phase, and the solvent was removed under a reduced pressure to produce the crude photoactive compound PAC3. The crude product was dissolved in 20 mL of acetone and this solution was poured into 150 mL of heptane to produce PAC3 as a colorless precipitate, which was isolated by filtration and dried to provide a colorless solid. The yield of PAC3 was 8.9 g (63.5%). $^1$H NMR (in acetone-d6), δ (ppm): 7.90 (d, 4H, ArH), 7.53 (d, 2H, ArH), 7.49 (d, 2H, ArH), 7.38 (d, 4H, ArH), 7.22 (d, 1H, CH═CH), 6.42 (d, 1H, CH═CH), 1.19 (s, 18H, 6($CH_3$)). UPLC purity was 99.30% as detected by UV light absorbance at 210 nm.

Synthesis of bis(4-(tert-butyl)phenyl)iodonium (Z)-3-fluoro-3-phenylacrylate (PAC4)

1.0 g of α-fluorocinnamic acid (6.0 mmol) and 10 mL of THF were combined to prepare a solution, 0.2 g of LiOH in 5 mL of DI water was added to the solution, and the resulting mixture was stirred at room temperature (ca. 25° C.) for 1 hour. The THF was then removed under a reduced pressure to produce a lithium α-fluorocinnamate salt. To the lithium α-fluorocinnamate salt was added 10 mL of DI water, 10 mL of DCM, and 2.0 g of bis(4-(tert-butyl)phenyl)iodonium acetate (4.42 mmol), and the mixture was stirred at room temperature (ca. 25° C.) for 4 hours. The organic phase was then washed with DI water (5×15 mL). The organic phase was separated from the aqueous phase, and the solvent was removed under a reduced pressure to produce the crude photoactive compound PAC4 as a white solid. The crude product was suspended in 25 mL of heptane, and the product was isolated by filtration and dried to provide a white solid.

The yield of PAC4 was 2.2 g (65.5%). $^1$H NMR (in acetone-d6), δ (ppm): 8.12 (d, 4H, ArH), 7.50 (m, 6H, ArH), 7.33-7.26 (m, 3H, ArH), 6.50 (d, 1H, CH═CF), 1.20 (s, 18H, 6($CH_3$)). UPLC purity was 99.92% as detected by UV light absorbance at 210 nm.

Synthesis of bis(4-(tert-butyl)phenyl)iodonium (E)-3-cyclohexylacrylate (PAC5)

1.0 g of (E)-3-cyclohexylacrylic acid (6.48 mmol) and 10 mL of THF were combined to prepare a solution, 0.15 g of LiOH in 5 mL of DI water was added to the solution, and the resulting mixture was stirred at room temperature (ca. 25° C.) for 1 hour. The THF was then removed under a reduced pressure to produce a lithium 3-cyclohexylacrylate salt. To the lithium 3-cyclohexylacrylate salt was added 10 mL of DI water, 10 mL of DCM, and 2.0 g of bis(4-(tert-butyl)phenyl) iodonium acetate (4.42 mmol), and the mixture was stirred at room temperature (ca. 25° C.) for 4 hours. The organic phase was then washed with DI water (5×15 mL). The organic phase was separated from the aqueous phase, and the solvent was removed under a reduced pressure to produce the crude photoactive compound PAC5 as a white solid. The crude product was suspended in 25 mL of heptane, and the product was isolated by filtration and dried to provide a white solid. The yield of PAC5 was 1.7 g (47.9%). $^1$H NMR (in acetone-d6), δ (ppm): 7.83 (d, 4H, ArH), 7.39 (d, 4H, ArH), 6.51 (2H, CH═CH), 5.75 (d, 1H, CH═CH), 2-1.75 (6H, aliphatic-H), 1.19 (s, 18H, 6($CH_3$)), 1.18-1.08 (m. 5H aliphatic-H). UPLC purity was 99.66% as detected by UV light absorbance at 210 nm.

Synthesis of bis(4-(tert-butyl)phenyl)iodonium (E)-3-(4-iodophenyl)acrylate (PAC6)

1.0 g of (E)-3-(4-iodophenyl)acrylic acid (3.65 mmol) and 10 mL of THF were combined to prepare a solution, 0.15 g of LiOH in 5 mL of DI water was added to the solution, and the resulting mixture was stirred at room temperature (ca. 25° C.) for 1 hour. The THF was then removed under a reduced pressure to produce a lithium 3-cyclohexylacrylate salt. To the lithium 3-cyclohexylacrylate salt was added 10 mL of DI water, 10 mL of DCM, and 1.5 g of bis(4-(tert-butyl)phenyl)iodonium acetate (3.32 mmol), and the mixture was stirred at room temperature (ca. 25° C.) for 4 hours. The organic phase was then washed with DI water (5×15 mL). The organic phase was separated from the aqueous phase, and the solvent was removed under a reduced pressure to produce the crude photoactive compound PAC5 as a white solid. The crude product was suspended in 25 mL of heptane, and the product was isolated by filtration and dried to provide a white solid. The yield of PAC6 was 1.7 g (70.8%). $^1$H NMR (in acetone-d6), δ (ppm): 8.06 (d, 4H, ArH), 7.67 (d, 2H, ArH) 7.46 (d, 4H, ArH), 7.26 (d, 2H, ArH), 6.93 (2H, CH═CH), 6.33 (d, 1H, CH═CH), 1.21 (s, 18H, 6($CH_3$)). UPLC purity was 99.88% as detected by UV light absorbance at 210 n.

Synthesis of Triphenylsulfonium Cinnamate (PAC7)

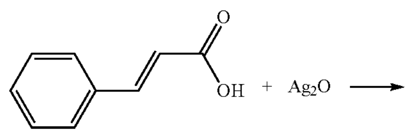

-continued

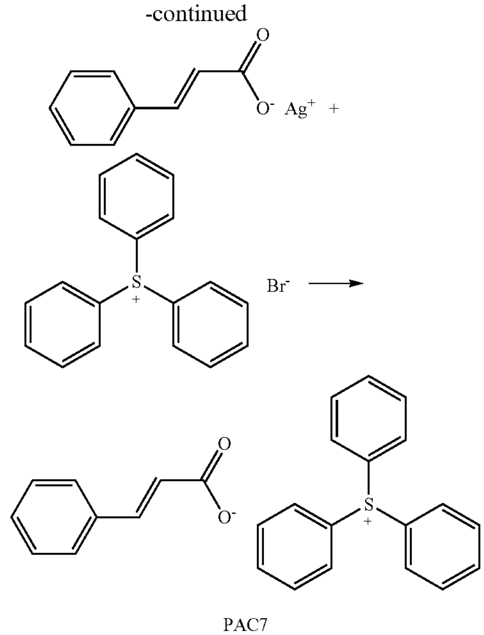

PAC7

10.0 g of cinnamic acid (67.49 mmol), 200 mL of acetone, and 200 mL of DI water were combined to prepare a solution, and then 7.0 g (30.2 mmol) of silver oxide was added in small portions to the solution. The resulting mixture was stirred at room temperature (ca. 25° C.) for 48 hours. The precipitate was isolated by filtration, washed with acetone, and dried under a reduced pressure. The yield of the cinnamate silver salt was 13.5 g.

5.0 g of the cinnamate silver salt (5.0 g, 19.6 mmol) were dissolved in 150 mL of methanol and 30 mL DI water to form a solution, and then 6.0 g of triphenylsulfonium bromide (17.47 mmol) was added to the solution. The reaction mixture was stirred at room temperature (ca. 25° C.) for 12 hours. $^1$H NMR of the reaction mixture showed the expected product with cation to anion ratio of 1:1. The mixture was filtered to remove undissolved salts and the solvent was removed under a reduced pressure. The resulting residue was dissolved in acetone and filtered through a plug of diatomaceous earth. The solvent was removed under reduced pressure from the filtrate to produce PAC7 as a colorless oil. The yield of PAC7 was 1.7 g (70.8%). $^1$H-NMR (in acetone-d6), δ (ppm): 8.08 (m, 6H, ArH), 7.88-7.78 (m, 9H, ArH), 7.41 (m, 2H), 7.27 (m, 2H, ArH), 7.20 (m, 2H, ArH), 6.50 (d, 1H, CH═CH). UPLC purity was 99.75% as detected by UV light absorbance at 210 n.

Synthesis of Triphenylsulfonium Benzoate (CPAC8)

5.0 g of benzoic acid (18.42 mmol), 100 mL of acetone, and 100 mL of DI water were combined to prepare a solution, and then 4.27 g (18.42 mmol) of silver oxide was added in small portions to the solution. The resulting mixture was stirred at room temperature (ca. 25° C.) for 48 hours. The precipitate was isolated by filtration, washed with acetone, and dried under a reduced pressure. The yield of the benzoate silver salt was 7.3 g.

2.5 g of the benzoate silver salt (10.9 mmol) were dissolved in 100 mL of methanol and 20 mL DI water to form a solution, and then 2.5 g of triphenylsulfonium bromide (7.28 mmol) was added to the solution. The reaction mixture was stirred at room temperature (ca. 25° C.) for 12 hours. $^1$H-NMR of the reaction mixture showed the expected product with cation to anion ratio of 1:1. The mixture was filtered to remove undissolved salts and the solvent was removed under a reduced pressure. The resulting residue was dissolved in acetone and filtered through a plug of diatomaceous earth. The solvent was removed under reduced pressure from the filtrate to produce CPAC8 as a colorless oil. UPLC purity was 99.63% as detected by UV light absorbance at 210 nm.

Synthesis of triphenylsulfonium (E)-3-(thiophen-3-yl)acrylate (CPAC9)

2.55 g of (E)-3-(thiophen-3-yl)acrylic acid (16.2 mmol), 50 mL of acetone, and 50 mL of DI water were combined to prepare a solution, and then 1.80 g (7.76 mmol) of silver oxide was added in small portions to the solution. The resulting mixture was stirred at room temperature (ca. 25° C.) for 48 hours. The precipitate was isolated by filtration, washed with acetone, and then dried under a reduced pressure. The yield of the (E)-3-(thiophen-3-yl)acrylate silver salt was 3.30 g.

3.30 g of the (E)-3-(thiophen-3-yl)acrylate silver salt (10.9 mmol) was dissolved in 100 mL of methanol and 20 mL DI water to form a solution, and then 3.48 g of triphenylsulfonium bromide (10.0 mmol) was added to the solution. The reaction mixture was stirred at room temperature (ca. 25° C.) for 12 hours. $^1$H-NMR analysis of the reaction mixture showed the expected product with cation to anion ratio of 1:1. The mixture was filtered to remove undissolved salts and then the solvent was removed under a reduced pressure. The resulting residue was dissolved in acetone and filtered through a plug of diatomaceous earth. The solvent was removed under a reduced pressure from the filtrate to produce CPAC9 as a colorless oil. UPLC purity was 99.64% as detected by UV light absorbance at 210 nm.

PAC1

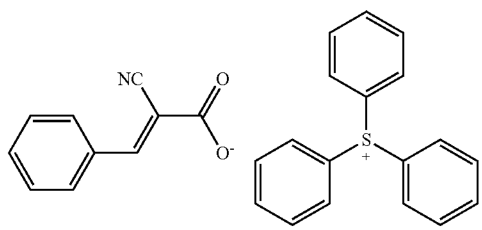

PAC2

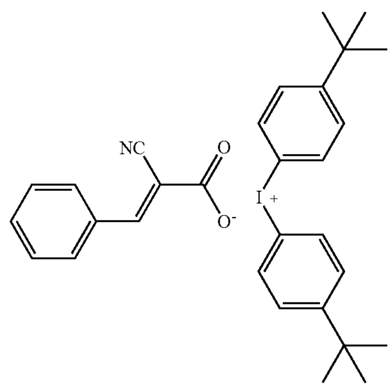

-continued

PAC3

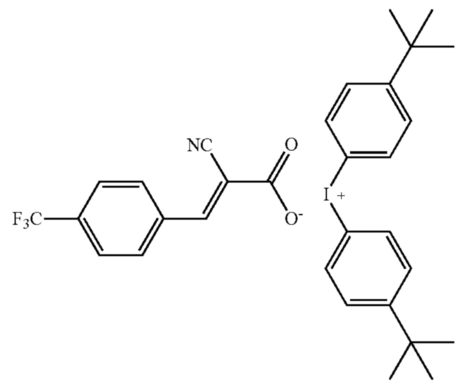

PAC4

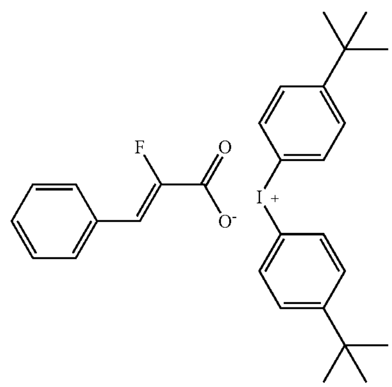

PAC5

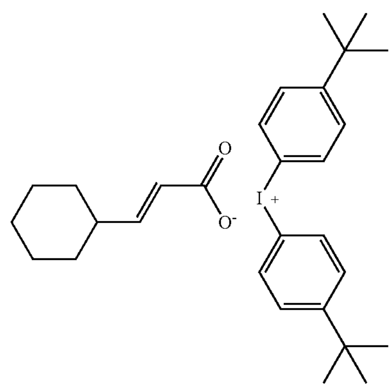

PAC6

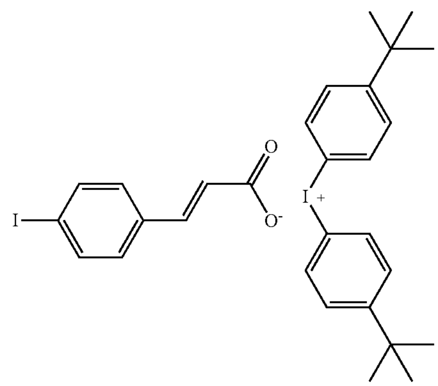

-continued

PAC7

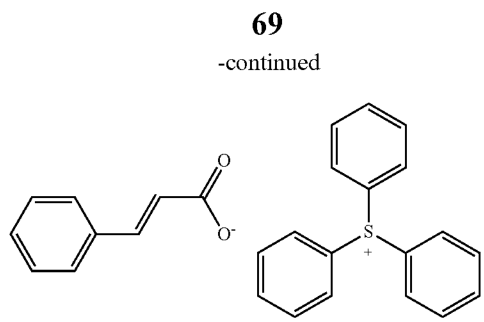

CPAC8

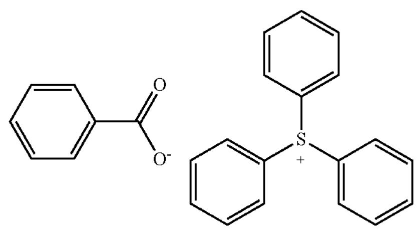

CPAC9

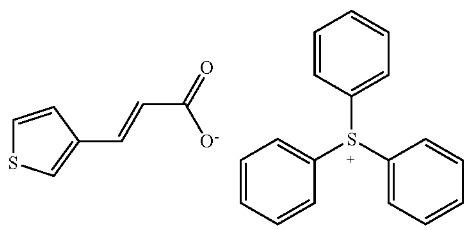

P1

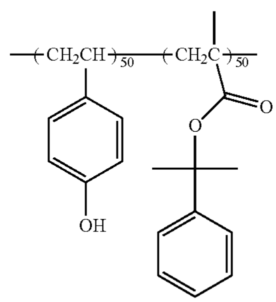

P2

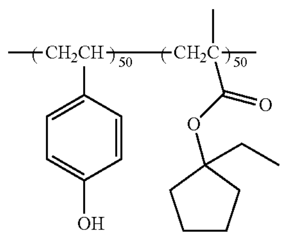

PAG-1

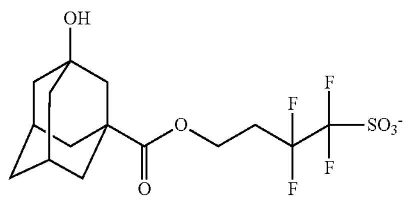

-continued

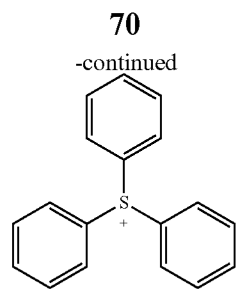

Q1

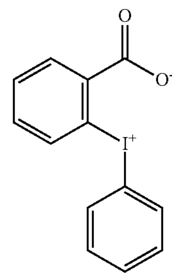

Photoresist Formulations 1. Photoresist compositions were prepared by dissolving the solid components in solvents using the materials and amounts set forth in Table 1, to a total solids content of 2.6 wt %. Each mixture was shaken using a mechanical shaker filtered through a PTFE disk-shaped filter having a pore size of 0.2 m. The amounts of the polymer, PAG, and photoactive compound are reported as wt % based on the total solids of the photoresist composition. The solvent system contained propylene glycol monomethyl ether acetate (PGMEA) (50 wt %) and methyl 2-hydroxyisobutyrate (50 wt %).

Lithographic Evaluation 1. Lithography was performed using a CLEAN TRACK ACT8 (TEL, Tokyo Electron Co.) wafer track. 200 nm wafers for photolithographic testing were coated with an AR™ 3 BARC (DuPont Electronics & Industrial) and softbaked at 205° C. for 60 seconds to give a 60 nm film. A coating of AR™ 40 BARC (DuPont Electronics & Industrial) was then disposed on the AR™ 3 layer and softbaked at 205° C. for 60 seconds to form a second BARC layer having a thickness of 80 nm. A photoresist composition was then coated onto the dual BARC stack and soft-baked at 110° C. for 60 seconds to give a photoresist film layer having a thickness of 70 nm. The wafers were exposed to 248 nm radiation on a Canon FPA-5000 ES4 scanner (NA=0.8, outer sigma=0.85, inner sigma=0.57) using a mask having a 1:1 line-space (L/S) pattern (120 nm linewidth). The exposed wafers were subjected to a post-exposure bake at 100° C. for 60 seconds, developed with a 0.26 N TMAH solution for 60 seconds, and then rinsed with DI water and spun dried to form photoresist patterns. Critical dimension (CD) linewidth measurements of the formed patterns were made using a HITACHI S-9380 CD-SEM. Line width roughness (LWR) was determined from the deviation in the width of a line measured over a given length and was evaluated using a 3-sigma (36) deviation of the width from the distribution of a total of 100 arbitrary points of linewidth measurements. The LWR data is shown in Table 1.

TABLE 1

| Example | Polymer | PAG | Photoactive compound | LWR (nm) |
|---|---|---|---|---|
| 1 | P1 (79.18) | PAG 1 (16.56) | PAC1 (4.26) | 7.75 |
| 2 | P1 (78.19) | PAG 1 (16.35) | PAC2 (5.46) | 6.82 |
| 3 | P1 (77.87) | PAG 1 (16.28) | PAC3 (5.85) | 7.93 |
| 4* | P1 (80.05) | PAG 1 (16.75) | Q1 (3.20) | 8.22 |

*Denotes a comparative example.

Photoresist Formulations 2. Photoresist compositions were prepared by dissolving the solid components in solvents using the materials and amounts set forth in Table 2, to a total solids content of 4.2 wt %. Each mixture was shaken using a mechanical shaker and then filtered through a PTFE disk-shaped filter having a pore size of 0.2 m. The amounts of the polymer, PAG, and photoactive compound are reported as wt % based on the total solids of the photoresist composition. The solvent system contained PGMEA (50 wt %) and methyl 2-hydroxyisobutyrate (50 wt %).

Lithographic Evaluation 2. Lithography was performed using a CLEAN TRAC ACT8 (TEL, Tokyo Electron Co.) wafer track. 200 nm wafers for photolithographic testing were coated with an AR™ 3 BARC (DuPont Electronics & Industrial) and softbaked at 205° C. for 60 seconds to give a 60 nm film. A coating of AR™ 40A BARC (DuPont Electronics & Industrial) was then disposed on the AR™ 3 layer and softbaked at 2050° C. for 60 seconds to form a second BARC layer having a thickness of 80 nm. A photoresist composition was then coated onto the dual BARC stack and soft-baked at 110° C. for 60 seconds to give a photoresist film layer having a thickness of 120 nm.

The wafers were exposed to 248 nm radiation using a CANON FPA-5000 ES4 scanner (NA=0.8, outer sigma=0.85, inner sigma=0.57) with a mask having a 1:1 L/S pattern (120 nm linewidth). The exposed wafers were subjected to a post-exposure bake at 100° C. for 60 seconds, developed with a 0.26 N TMAH solution for 60 seconds, and then rinsed with DI water and spun dried to form photoresist patterns. CD linewidth measurements of the formed patterns were made using a HITACHI S-9380 CD-SEM. LWR was determined from the deviation in the width of a line measured over a given length and was evaluated using a 36 deviation of the width from the distribution of a total of 100 arbitrary points of linewidth measurements. The LWR data is shown in Table 2.

TABLE 2

| Photoresist Composition | Polymer | Photoacid generator | Photoactive compound | LWR (nm) |
|---|---|---|---|---|
| 5 | P2 (77.47) | PAG 1 (19.37) | PAC1 (3.16) | 6.98 |
| 6 | P2 (76.75) | PAG 1 (19.19) | PAC2 (4.06) | 6.47 |
| 7 | P2 (76.89) | PAG 1 (19.22%) | PAC3 (3.89) | 7.20 |
| 8 | P2 (76.78) | PAG 1 (19.20) | PAC4 (4.02) | 6.70 |
| 9 | P2 (76.85) | PAG 1 (19.21) | PAC5 (3.94) | 7.03 |
| 10 | P2 (76.19) | PAG 1 (19.05) | PAC6 (4.76) | 7.35 |
| 11 | P2 (77.61) | PAG 1 (19.40) | PAC7 (2.99) | 7.33 |

TABLE 2-continued

| Photoresist Composition | Polymer | Photoacid generator | Photoactive compound | LWR (nm) |
|---|---|---|---|---|
| 12* | P2 (77.76) | PAG1 (19.44) | CPAC8 (2.89) | 8.09 |

*Denotes comparative example.

Photoresist Formulations 3. Photoresist compositions were prepared by dissolving the solid components in solvents using the materials and amounts set forth in Table 3, to a total solids content of 1.55 wt %. Each mixture was shaken using a mechanical shaker filtered through a PTFE disk-shaped filter having a pore size of 0.2 m. The amounts of the polymer, PAG, and photoactive compound are reported as wt % based on the total solids of the photoresist composition. The solvent system contained PGMEA (50 wt %) and methyl 2-hydroxyisobutyrate (50 wt %).

Lithographic Evaluation 3. Lithography was performed using a CLEAN TRAC ACT8 (TEL, Tokyo Electron Co.) wafer track. 300 nm wafers for photolithographic testing were coated with an organic BARC film layer to give a 60 nm film and then a silicon-containing antireflective coating (SiARC) film layer was disposed on the organic BARC film layer to form a second layer having a thickness of 20 nm. A photoresist composition was then spin-coated onto the bilayer stack of BARC/SiARC and soft-baked at 110° C. for 60 seconds to give a photoresist film layer having a thickness of 40 n.

The wafers were exposed to 13.5 nm radiation using a ASML NXE3400B scanner with a mask having a CD of 20.25 nm and trench patterns having 36 pitch. The exposed wafers were subjected to a post-exposure bake at 100° C. for 60 seconds, developed with a 0.26 N TMAH solution for 60 seconds, rinsed with DI water, and spun dried to form resist trench patterns. CD linewidth measurements of the formed trench patterns were made using a HITACHI CG5000 CD-SEM.

Table 3 shows the EUV sizing energy ($E_{size}$) determined for the examples, which was the irradiation energy where the trench pattern was resolved to 18 nm and is reported in millijoules per square centimeter ($mJ/cm^2$). Table 3 also shows the depth-of-focus (DOF) for the examples, which is the total distance range of focus that keeps the printed feature without any printing failure.

TABLE 3

| Example | Polymer | PAG | Photoactive compound | $E_{size}$ ($mJ/cm^2$) | DOF (nm) |
|---|---|---|---|---|---|
| 13 | P2 (75.87) | PAG 1 (18.97) | PAC1 (5.16) | 36 | 60 |
| 14 | P2 (74.72) | PAG 1 (18.68) | PAC2 (6.60) | 33.8 | >80 |
| 15 | P2 (74.95) | PAG 1 (18.74) | PAC3 (6.31) | 28.2 | >80 |
| 16 | P2 (74.78) | PAG 1 (18.70) | PAC4 (6.52) | 31.0 | 80 |
| 17 | P2 (74.88) | PAG 1 (18.72) | PAC5 (6.40) | 28.0 | >100 |
| 18 | P2 (73.85) | PAG 1 (18.46) | PAC6 (7.69) | 30.8 | >100 |
| 19* | P2 (76.04) | PAG1 (19.01) | CPAC8 (4.95) | 30.8 | 40 |
| 20* | P2 (76.33) | PAG1 (19.08) | CPAC8 (4.59) | 25.4 | 40 |

*Denotes comparative example.

As demonstrated by comparing the results in Tables 1, 2, and 3, the inventive photoactive compounds afforded photoresist compositions having unexpected lithographic performance, and up to a 20% reduction to LWR was achieved. The improvements to LWR were observed without impact on photospeed and with improvements to DOF.

While this disclosure has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A photoactive compound of formula (3a):

(3a)

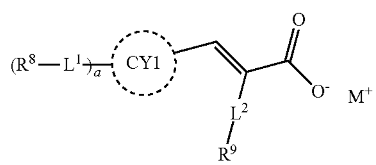

wherein, ring CY1 is a $C_{3-30}$ carbocyclic group or a $C_{3-30}$ heterocyclic group, wherein the $C_{3-30}$ heterocyclic group comprises;

each $L^1$ independently is a single bond or a divalent linking group;

each $R^8$ independently is hydroxyl, —F, —I, —$CF_3$, substituted or unsubstituted $C_{1-10}$ alkyl, substituted or unsubstituted $C_{3-20}$ cycloalkyl, substituted or unsubstituted $C_{3-20}$ heterocycloalkyl, substituted or unsubstituted $C_{6-10}$ aryl, or substituted or unsubstituted $C_{3-10}$ heteroaryl;

a is an integer from 0 to 10;

$L^2$ is a single bond, —C(O)—, or —C(O)O;

$R^9$ is hydrogen, cyano, hydroxyl, —F, —I, —$CF_3$, substituted or unsubstituted $C_{1-10}$ alkyl, substituted or unsubstituted $C_{3-20}$ cycloalkyl, substituted or unsubstituted $C_{3-20}$ heterocycloalkyl, substituted or unsubstituted $C_{6-10}$ aryl, or substituted or unsubstituted $C_{3-10}$ heteroaryl; and $M^+$ is a sulfonium cation or an iodonium cation, provided that $R^9$ is not cyano when $R^8$ is hydroxyl.

2. The photoactive compound of claim 1, wherein ring CY1 is $C_{3-8}$ cycloalkyl, $C_{6-14}$ aryl, or $C_{3-12}$ heteroaryl comprising nitrogen.

3. The photoactive compound of claim 1, wherein a is an integer from 0 to 5.

4. A photoactive compound of formula (3a):

(3a)

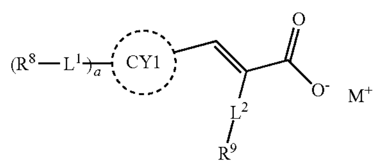

wherein, ring CY1 is a $C_{3-30}$ carbocyclic group or a $C_{3-30}$ heterocyclic group, wherein the $C_{3-30}$ heterocyclic group comprises a heteroatom selected from nitrogen, oxygen, or a combination thereof;

each $L^1$ independently is a single bond or a divalent linking group;

each $R^8$ independently is hydroxyl, —F, —I, —$CF_3$, substituted or unsubstituted $C_{1-10}$ alkyl, substituted or unsubstituted $C_{3-20}$ cycloalkyl, substituted or unsubstituted $C_{3-20}$ heterocycloalkyl, substituted or unsubstituted $C_{6-10}$ aryl, or substituted or unsubstituted $C_{3-10}$ heteroaryl;

a is an integer from 0 to 10;

L2 is a single bond, —C(O)—, —C(O)O—, or —C(O)N($R^{5a}$)—, wherein $R^{5a}$ is hydrogen, substituted or unsubstituted $C_{1-10}$ alkyl, substituted or unsubstituted $C_{1-10}$ heteroalkyl, substituted or unsubstituted $C_{6-10}$ aryl, or substituted or unsubstituted $C_{3-10}$ heteroaryl;

$R^9$ is substituted $C_{1-10}$ alkyl, substituted $C_{3-20}$ cycloalkyl, substituted $C_{3-20}$ heterocycloalkyl, substituted $C_{6-10}$ aryl, or substituted $C_{3-10}$ heteroaryl, and at least one substituent of the substituted $R^9$ group is hydroxy, —I, or a combination thereof; and $M^+$ is a sulfonium cation or an iodonium cation.

5. A photoresist composition, comprising:

the photoactive compound of claim 1; and a solvent.

6. The photoresist composition of claim 5, further comprising a material that switches solubility in a base or in an organic solvent under action of acid, wherein the material is different from the photoactive compound.

7. The photoresist composition of claim 6, further comprising a photoacid generator that is different from the photoactive compound.

8. A method for forming a pattern, the method comprising:

(a) forming a photoresist layer from a photoresist composition of claim 5 on a substrate;

(b) pattern-wise exposing the photoresist layer to activating radiation; and (c) developing the exposed photoresist layer to provide a resist relief image.

9. The method of claim 8, wherein a is an integer from 0 to 5.

10. The method of claim 8, wherein ring CY1 is a $C_{3-30}$ carbocyclic group.

11. The photoresist composition of claim 5, wherein ring CY1 is $C^{3-8}$ cycloalkyl, $C_{6-14}$ aryl, or $C_{3-12}$ heteroaryl comprising nitrogen.

12. The photoresist composition of claim 5, wherein a is an integer from 0 to 5.

13. A photoresist composition, comprising:

a photoactive compound; and a solvent, wherein photoactive compound is of formula (3a):

(3a)

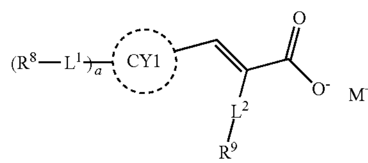

wherein, ring CY1 is a $C_{3-30}$ carbocyclic group or a $C_{3-30}$heterocyclic group, wherein the $C_{3-30}$ heterocyclic group comprises a heteroatom selected from nitrogen, oxygen, or a combination thereof;

each $L^1$ independently is a single bond or a divalent linking group;

each $R^8$ independently is hydroxyl, —F, —I, —$CF_3$, substituted or unsubstituted $C_{1-10}$ alkyl, substituted or unsubstituted $C_{3-20}$ cycloalkyl, substituted or unsubstituted $C_{3-20}$ heterocycloalkyl, substituted or unsubstituted $C_{6-10}$ aryl, or substituted or unsubstituted $C_{3-10}$ heteroaryl;

a is an integer from 0 to 10;

$L^2$ is a single bond, —C(O)—, —C(O)O—, or —C(O)N($R^{5a}$)—, wherein $R^{5a}$ is hydrogen, substituted or unsubstituted $C_{1-10}$ alkyl, substituted or unsubstituted $C_{1-10}$ heteroalkyl, substituted or unsubstituted $C_{6-10}$ aryl, or substituted or unsubstituted $C_{3-10}$ heteroaryl;

$R^9$ is substituted $C_{1-10}$ alkyl, substituted $C^{3-20}$ cycloalkyl, substituted $C^{3-20}$ heterocycloalkyl, substituted $C^{6-10}$ aryl, or substituted $C^{3-10}$ heteroaryl, and at least one substituent of the substituted $R^9$ group is hydroxy, —I, or a combination thereof; and $M^+$ is a sulfonium cation or an iodonium cation.

14. The photoresist composition of claim 5, wherein ring CY1 is a $C_{3-30}$ carbocyclic group.

15. The photoactive compound of claim 1, wherein ring CY1 is a $C_{3-30}$ carbocyclic group.

* * * * *